US008642570B2

(12) United States Patent
Schambach et al.

(10) Patent No.: US 8,642,570 B2
(45) Date of Patent: Feb. 4, 2014

(54) ASLV VECTOR SYSTEM

(75) Inventors: Axel Schambach, Seevetal (DE);
Christopher Baum, Hamburg (DE);
Julia Suerth, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 13/320,179

(22) PCT Filed: May 17, 2010

(86) PCT No.: PCT/EP2010/056757
§ 371 (c)(1),
(2), (4) Date: Feb. 9, 2012

(87) PCT Pub. No.: WO2010/130844
PCT Pub. Date: Nov. 18, 2010

(65) Prior Publication Data
US 2012/0172418 A1    Jul. 5, 2012

(30) Foreign Application Priority Data

May 15, 2009    (DE) .................. 10 2009 021 592

(51) Int. Cl.
*A61K 48/00* (2006.01)
*C07H 21/02* (2006.01)
*C07H 21/04* (2006.01)
*C12N 15/63* (2006.01)
*C12N 7/04* (2006.01)

(52) U.S. Cl.
USPC ... 514/44 R; 435/235.1; 435/236; 435/320.1; 536/23.1; 536/24.1

(58) Field of Classification Search
None
See application file for complete search history.

(56) References Cited

U.S. PATENT DOCUMENTS 7,070,992 B2 * 7/2006 Baum et al. .................. 435/325
2008/0064862 A1 * 3/2008 Harvey et al. ................. 536/22.1

FOREIGN PATENT DOCUMENTS

| EP | 1757702 | 2/2007 |
| EP | 1757703 | 2/2007 |

OTHER PUBLICATIONS

Aubert, D., et. al. "Inhibition of Proliferation of Primary Avian Fibroblasts through Expression of Histone H5 Depends on the Degree of Phosphorylation of the Protein", *The Journal of Cell Biology*, vol. 113, No. 3, May 1991, pp. 497-506.
Bailey, Susannah, et. al., "Novel Gammaretroviral Vectors for Gene Therapy of SCID-X1", *Molecular Therapy*, vol. 13, Supp. 1, May 2006, pp. S256-S257.
Baum, Christopher, et. al., "Retrovirus Vectors: Toward the Plentivirus?", *Molecular Therapy*, vol. 13, No. 6, Jun. 2006, pp. 1050-1063.
Chen-Wichmann, Linping, et.al., "SIN gammaretroviral vectors for the gene therapy of x-CGD", *Blood Cells, Molecules and Diseases*,40, (2008), p. 260.
Cullen, Bryan, et. al., "Functional Analysis of the Transcription Control Region Located Within the Avian Retroviral Long Terminal Repeat", *Molecular and Cellular Biology*, vol. 5, No. 3, Mar. 1985, pp. 438-447.
Flamant, Frederic, et. al., "Importance of 3' non-coding sequence for efficient retrovirus-mediated gene transfer in avian cells revealed by self-inactivating vectors", *Journal of General Virology*,(1993), 74, pp. 39-46.
Galla, Melanie, et.al., "Reverse Transcriptase Deficient Retroviral Vectors for Transient Cell Modification", *Molecular Therapy*, ,vol. 13, Supp. 1, May 2006, p. S177.
Hu, Jingquiong et. al., "Reduced Genotoxicity of Avian Sarcoma Leukosis Virus Vectors in Rhesus Long-term Repopulating Cells Compared to Standard Murine Retrovirus Vectors", *Molecular Therapy*, vol. 16 No. 9, Sep. 2008, pp. 1617-1623.
Hu, Jingquiong et. al., "Transduction of Rhesus Macaque Hematopoietic Stem and Progenitor Cells with Avian Sarcoma and Leukosis Viral Vectors", *Human Gene Therapy*, 18, Aug. 2007, pp. 691-700.
Hughes, Stephen H., "The RCAS Vector System", *Folia Biologica (Praha)*,50, 2004, pp. 107-119.
Mitchell, Rick S., et. al., "Retroviral DNA Integration: ASLV, HIV and MLV Show Distinct Target Site Prefernces", *PLoS Biology*, Aug. 2011, vol. 2, Issue 8. www.plosbiology.org, pp. 1127-1137.
Modlich, et. al., "Cell-culture assays reveal the importance of retroviral vector design for insertational genotoxicity", *Blood*, vol. 108, No. 8, Oct. 15, 2006, pp. 2545-2553.
Schambach, Axel, et. al., "Design of Safe and Efficient Vector for Bone Marrow Chemoprotection by $O^5$-Methyl-Guanine-DNA-MethylTransferase", *Molecular Therapy*, vol. 11, Supp. 1, May 2005, pp. S322-S323.
Schambach, Axel, et. al., "Vector design for expression of $O^6$-methylguanine-DNA-methyltransferase in hematopoietic cells", *DNA Repair*, 6 (2007), pp. 1187-1196.

(Continued)

Primary Examiner — Doug Schultz
(74) Attorney, Agent, or Firm — Greer, Burns & Crain Ltd.

(57) ABSTRACT

The invention provides a viral self-inactivating (SIN) vector on the basis of the avian sarcoma leukosis virus (ASLV) as well as a split-packaging system comprising in addition to the SIN vector a first helper plasmid serving for the expression of the viral fusion protein gag-pol and a second helper plasmid serving for the expression of the retroviral envelope protein (env). The first and second helper plasmid, for example contained in a packaging cell line or transiently transfected, serve for the generation of non-replicating (RCR-incompetent) viral particles containing RNA having a SIN LTR according to the invention at the 3' terminus, wherein the RNA can have a therapeutically effective section which e.g. is denoted a transgene. This 3' SIN LTR contains an extensive deletion of the U3 region which in the course of the reverse transcription is copied into the 5' LTR. In addition, in the SIN vector all coding regions of ASLV as well as the retroviral splice donor site are removed.

27 Claims, 10 Drawing Sheets

(56) References Cited

OTHER PUBLICATIONS

Figure 1:
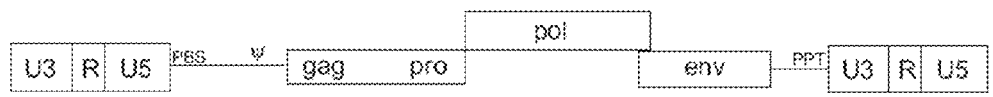

Schambach, Axel, et. al., "Equal Potency of Gammaretroviral and Lentiviral SIN Vectors for Expression of $O^6$-methylguanine-DNA-methyltransferase in hematopoietic cells", *Molecular Therapy*, Bol. 13, No. 2. Feb. 2006, pp. 391-400.

Schambach, Axel, et. al., "Improving Transcriptional Termination of Self-inactivating Gamma-retroviral and Lentiviral Vectors", *Molecular Therapy*, vol. 15, No. 6, Jun. 2007, pp. 1167-1173.

Kraunus, J, et al., "Self-inactivating retroviral vectors with improved RNA processing", *Gene Therapy*, (2004) 11, pp. 1568-1578.

Schambach, Axel, et. al., "Overcoming promoter competition in packaging cells improves production of self-inactivating retroviral vectors", *Gene Therapy*, (2006) 13, pp. 1524-1533.

Zaiss, Anne Katherin, et al., "RNA 3' Readthrough of Oncoretrovirus and Lentivirus: Implications for Vector Safety and Efficacy", *J. Virol.*, vol. 76, No. 14, Jul. 2002, pp. 7209-7219.

\* cited by examiner

Eco/ampho MLV env
Rd114
GALV
VSVg

Fig. 5

```
              AATGTAGTCTTATGCAATACTCTTGTA----------------------------------
              |         |         |         |         |         |         |
              10        20        30        40        50        60        70
ASLV dU3 noTATA  AATGTAGTCTTATGCAATACTCTTGTA----------------------------------     28
ASLV dU3         AATGTAGTCTTATGCAATACTCTTGTA----------------------------------     28
ASLV U3          AATGTAGTCTTATGCAATACTCTTGTAGTCTTAACATGGTAGCATGAGTTGGTAACATGCCTTACAA  70

|         |         |         |         |         |         |
              80        90        100       110       120       130       140
ASLV dU3 noTATA  ----------------------------------------------------------------     28
ASLV dU3         ----------------------------------------------------------------     28
ASLV U3          GTAGCAAAAGTACCTGTGTCCGATTGTCAAGTAAGTCGTACAGTTGCCTTATTAGTAAGCC         140

■■                        ■
                                                  CGTAGAGATATGTATTTAAGCC
              |         |         |         |         |         |         |
              150       160       170       180       190       200       210
ASLV dU3 noTATA  ------------------------------------------------CGTA--------GCGC    35
ASLV dU3         ------------------------------------------------CGTAGAGATATGTATTTAAGCC 51
ASLV U3          AACAGACGTTCTGACATCGATGGACGAATTACTGAATTCTCATGCAAGATATTGTATTTAAGCC      210

CTAGTCTGATACAATAAAC
              |
              220
ASLV dU3 noTATA  CTAGTCTGATACAATAAAC                                               54
ASLV dU3         CTAGTCTGATACAATAAAC                                               70
ASLV U3          CTAGTCTGATACAATAAAC                                               229
``` wherein
ASLV U3 = SEQ ID NO: 1
ASLV dU3 = SEQ ID NO: 2
ASLV dU3 noTATA = SEQ ID NO: 4

SEQ ID NO: 5

SEQ ID NO: 9

SEQ ID NO: 7

SEQ ID NO: 11

SEQ ID NO: 14

ASLV VECTOR SYSTEM

The present invention relates to a viral self-inactivating (SIN) vector on the basis of the avian sarcoma leukosis virus (ASLV), to viral particles containing the vector according to the invention, to a split-packaging system comprising or consisting of the SIN vector, a first helper plasmid serving for the expression of the viral fusion protein gag-pol and a second helper plasmid serving for the expression of the retroviral envelope protein (env), as well as to a method for the production of the viral particle by means of the split-packaging system, especially by expression in cultured human cells. Furthermore, the invention relates to the viral particle for use as medicament, especially for transfer of a transgene into cells, as well as to the use of the viral particle for the production of the medicament. The first and second helper plasmid, for example contained in a packaging cell line or transiently transfected, serve for the generation of nonreplicating (RCR-incompetent) viral particles containing RNA having a SIN LTR according to the invention at the 3' terminus, wherein the RNA can have a therapeutically effective section which e.g. is denoted a transgene. This 3' SIN LTR comprises an extensive deletion of the U3 region which in the course of the reverse transcription is copied into the 5' LTR.

For the expression of a transgene, which e.g. for use for the gene therapy can be a human or heterologous gene, the viral SIN vector preferably contains an expression cassette arranged in 5' to the 3' SIN LTR.

The vector according to the invention also in human packaging cells allows the generation of viral particles at a high titre and is characterized in that during the transduction of target cells, especially of human cells, by contacting the cells extracorporeally, i.e. in vitro, or by means of administration of a particle adapted to this purpose to a patient cells transduced in vivo are generated expressing the transgene in a stable way and with low reduction, respectively, over a long period of time, wherein the frequency of the transformation of target cells by oncogene activation is low. The expression cassette has a promoter in 5' to the nucleic acid sequence encoding the transgene and a post-transcriptional regulatory element (PRE), especially a WPRE (PRE of the woodchuck hepatitis virus (WHV)), preferably in 3' to the sequence encoding the transgene.

STATE OF THE ART

Hughes (Folia Biologika 50, 107-119 (2004)) describes a series of viral vectors on the basis of the avian leukosis virus (ALV) which for better production of replication-competent retroviruses (RCR) have a functioning LTR. (RCAS: Replication-Competent ASLV LTR with a Splice Acceptor). In this system all components for the virus production lie on one plasmid (as in the full-length virus), and a possible transgene is inserted into the 3' untranslated region (UTR).

Hu et al. (Molecular Therapy, 1617-1623 (2008)) show that ASLV is not prone to preferably insert inside or in the proximity of proto-oncogenes and that the LTRs of ALSV do not tend to activate adjacent genes and therefore conclude that ALSV should form a suitable basis for viral vectors. It is indicated that a deletion of the enhancer region (enhancer) in the LTR or the inhibition of through-transcribing over a termination signal could be achieved by an improved polyadenylation.

Hu et al. (Human Gene Therapy 691-700 (2007)) and Mitchell at al. (Plos Biology, e234, 2004) show that ALSV is not prone to preferably insert inside or in the proximity of proto-oncogenes, especially without a clear preference for regions close to the promoter. Accordingly, the danger of insertional mutagenesis in comparison to the clinically used vector systems from murine leukemic virus (MLV) and human immunodeficiency virus (HIV) is estimated as lower. It is indicated that a deletion of the enhancer region (enhancer) in the LTR or the prevention of through-transcribing over a termination signal would be desirable. Due to the vector architecture (1 plasmid, replicating) this system is usually not suitable for clinical applications.

Hu et al. show that viral vectors derived from ASLV having intact LTRs do not replicate in mammalian cells. The exact reason for this is unclear.

Due to the retroviral architecture of 2 LTRs retroviruses have intrinsically weak polyA signals. For lentiviral vectors it is known that the through-transcribing from the 3' terminus of the inserted viral vector can lead to undesired gene activation according to for example Zaiss et al. (Journal of Virology 7209-7219 (2002)) and Schambach, Baum et al. (Molecular Therapy 2007, 15(6): 1167-73). This is also important in that the U3 region aside from promoter elements and enhancer elements also contains polyadenylation enhancers and therefore any deletions have to be validated anew for each virus family with regard to residual enhancer activity and efficiency of the polyadenylation.

For gammaretroviral vectors Kraunus et al. (Gene Therapy 568-1578 (2004)) propose to delete the complete region of the enhancer element and the promoter of the 3' U3 region and to leave only the first 22 bp upstream of the enhancer and the last downstream 14 bp. With ASLV and rous sarkoma virus (RSV) the LTR region is complicated by a very short R region such that the polyA signal (AATAAA) comes to lie in the U3 region. This is very unusual for retroviruses (otherwise located in the R region) and makes the construction of a SIN vector more difficult.

Aubert et al. (The J. of Cell Biology 113, 497-506 (1991) and Flamant et al. (Journal of General Virology 74, 39-46 (1993)) describe deletions of the U3 region of ALV from −149 to −15 relative to the R region, and from −149 to −15, and −98 to −59, respectively, again relative to the R region. In all these U3 regions remaining enhancer elements are still contained (Cullen et al., MCB 1985, 438-47) which is problematic for possible clinical applications. This is because these enhancer elements might dysregulate adjacent genes (e.g. oncogenes) by insertional mutagenesis.

OBJECT OF THE INVENTION

It is therefore the object of the invention to provide a clinically suitable split-packaging system having a viral vector and helper plasmids for the production in mammalian cells (e.g. human cells, for example HEK293T) by which the viral vector can be produced packaged as a viral particle, in which the risk of the recombination to a replication-competent retrovirus (RCR) is minimized, and also the risk is minimized that the insertion of the viral vector leads to the activation of adjacent genes of the target cell (insertional mutagenesis). Preferably, the viral vector and the system having helper plasmids, respectively, shall furthermore allow the generation of viral particles at a high titre, wherein the viral vector shall be able to contain an expression cassette from which a transgene and gene regulatory sequences (e.g. shRNA, miRNA etc.) are efficiently transcribed and/or translated. Preferably, these vectors are pseudotyped with clinically suitable envelope proteins (e.g. RD114/TR, MLV amphotropic env, glycoprotein of the vesicular stomatitis virus (VSVg)). All these criteria are aspired in combination, since they are essential for possible clinical applications.

GENERAL DESCRIPTION OF THE INVENTION

The invention achieves this object by the features of the claims, and especially by a vector having the aspired properties. A viral RNA can be transcribed from a plasmid according to the claims providing a viral vector on the basis of ASLV, the 3' U3 region of which produces or is, respectively, a self-inactivating 3' LTR (SIN LTR), as well as providing the viral particle containing a nucleic acid sequence encoding the viral vector, especially RNA. Furthermore, the invention provides a system having a first helper plasmid encoding in an expression cassette the coding sequence for the gag-pro-pol fusion protein of ASLV, and having a second helper plasmid encoding in an expression cassette an envelope protein (env), e.g. env of ASLV, RD114/TR, MLV Amphotrop, VSVg or MLV Ecotrop.

Upon presence of the first and of the second helper plasmids in a eukaryotic cell, in the following also denoted as packaging cell, viral particles are produced at high titre the viral RNA of which itself is self-inactivating (SIN) due to the deletions in the 5' U3 region originating in a target cell from the 3' U3 region during the reverse transcription to the viral DNA, but allow a high transcription rate and efficient translation of the transgene which is arranged in an expression cassette in 5' before the 3' SIN LTR. In this configuration the activation of adjacent genomic sequences by the insertion of the viral vector is significantly reduced. The reduction of the activation of adjacent sequences has been shown for γ-retroviral vectors by Zychlinski et al. (Mol. Ther. 16: 718-725 (2008)).

Mutations which are known for viral SIN vectors on the basis of other retroviruses, for example lentiviruses, which combine the properties of the high titre in packaging cells on the one hand, no promoter activity in the LTR, as well as an efficient transcription of a transgene from a vector-internal expression cassette without through-transcription into genomic sequences at the place of insertion, cannot be transferred to the construction of SIN LTR vectors on the basis of ASLV. This is because the arrangement of functional elements in the individual viruses and their interaction with cellular host factors are not identical to each other and the effect of the change of sequences to the titre, to the prevention or the activation of adjacent genomic sequences at the place of insertion, and to a transcription of the transgene from an internal expression cassette cannot be predicted.

The viral vector according to the invention in the place of the wild-type LTR contains a 3' LTR the U3 region of which is deleted over a large section such that the transcriptional activity of the promoter and enhancer regions of the U3 region is essentially, preferably completely, turned off and eliminated, respectively. The elimination of the promoter and enhancer regions of the U3 region, e.g. by deletion or replacement of nucleotides of this region, is determined by means of an activity test when the promoter activity of the deleted or substituted U3 region is on the level of the background activity of a promoterless reporter gene, as e.g. for a completely deleted U3 region for a reporter gene subsequently arranged functionally in 3'. In particular, according to the invention the U3 region of ASLV only has nucleotides 1-27 and nucleotides 187-229, preferably only nucleotides 1-27 and 207-229 of the 229 nucleotides of the wild-type U3 region (SEQ ID NO: 1). This altered 3' U3 region of the viral vector according to the invention, in which at the wild-type U3 region nucleotides 28-186 are deleted, and preferably in addition nucleotides 187-202 are deleted, after reverse transcription and integration into the genome of a target cell essentially has no promoter activity and/or enhancer activity. The packageable viral RNA is driven by a strong promoter arranged in 5' which is lost in the course of the reverse transcription and is not contained in the viral RNA produced by transcription, respectively. This allows the generation of a transcript which in combination with a first and a second helper plasmid is suitable for the generation of viral particles having a high titre which contain the viral RNA.

The deletion of promoter regions and of enhancer regions optionally can be substituted by an insertion with a nucleotide sequence having no promoter activity or enhancer activity.

The 3' SIN LTR of the vector according to the invention can consist of the aforementioned sections of the deleted wild-type U3 region, a wild-type R region and a wild-type U5 region. The U3 region having deletions according to the invention optionally can contain additional nucleotide sequences without promoter activity between the remaining sections of the wild-type U3 region, which for example are selected from the group comprising miRNA, shRNA, polyadenylation enhancers (USE), recombinase recognition sequences (e.g. LoxP, Rox, FRT) and insulator elements (e.g. cHS4).

For insertion of nucleotide sequences having no promoter activity into the U3 region according to the invention this region preferably has an unique cutting site for a restrictase, especially preferred in that the nucleotides 187-190 in the numbering of the wild-type U3 region through mutation produce the base sequence CGTA, whereby a secondary cutting site for SnaBI having the recognition sequence TACGTA is generated.

As an alternative to the deletion of the nucleotides 187-202, also the nucleotides 200-206 (TATTTAA) can be mutated, for example into the sequence TGTCTAA. It is assumed that the nucleotides 200-206 form the TATA box of the wild-type U3 region, so that a mutation which changes this TATA box reduces or abolishes this portion of the promoter activity of the U3 region.

The deleted U3 region according to the invention further has an integrase attachment site (integrase attachment), especially in nucleotides 1-25, as well as a polyA signal, e.g. at nucleotides 223-228, each in the numbering of the nucleotides of the wild-type U3 region. It is assumed that the maintenance of the integrase attachment site and of the polyA signal is important for the viral infection. Surprisingly, the vector according to the invention on the one hand allows a production of viral particles at a high titre in a packaging cell or packaging cell line, and on the other hand allows an efficient transcription of a transgene from an expression cassette from an internal strong promoter following reverse transcription and integration into the genome of a target cell, without a through-transcription over the 3' SIN LTR occurring into adjacent regions of the integration site or activation of adjacent genomic sequences.

Viral particles produced in packaging cells which contained viral RNA having a 3' SIN LTR according to the invention or a 3' U3 region according to the invention, without concentration had a titre of approximately $1 \times 10^6$ infectious particles/mL. Therein the titre was influenced by the gene encoding the gag-pro-pol fusion protein and the envelope protein, respectively, of the first and the second helper plasmid, respectively, and was not significantly influenced by the nature or extent of the deletion in the U3 region.

Surprisingly, the expression of a transgene from an expression cassette in viral vectors according to the invention having a SIN deletion was higher by approximately a factor of 3 than in a comparative vector, in which the 3' LTR had a U3 region of wild-type sequence. According to the invention it is further preferred that the coding sequences of the first and/or of the second helper plasmid are codon-optimized such that the viral codons are substituted by codons of the target cell, especially are substituted by human codons, e.g. in methods for the production of viral particles and of viral vectors according to the invention which e.g. find a use as medicament or in the production of pharmaceutical compositions. A preferred helper plasmid according to the invention contains a sequence encoding the gag-pro-pol fusion protein in which viral codons are adapted to the human codon usage.

In the use as a medicament the viral particle containing the viral vector can be prepared for administration e.g. to a patient/human or to a non-human animal. Alternatively, the viral particle and the viral vector, respectively, can be contacted with cells originating from such a patient, i.e. for in vitro transduction of cells which subsequently, optionally with the step of cultivation and/or selection, are prepared and provided, respectively, as transduced cells for transfer into a patient, wherein preferably the patient is the same from which the cells originate.

According to the invention in the codon-optimized coding sequence for the gag-pro-pol fusion protein the initial shift of the reading frame by −1 and the transition from pro to pol from the wild-type ASLV has been maintained.

It has been found that the adaptation of the codon usage of ASLV to the codon usage of the target cell, especially to the human codon usage, for the coding regions of the helper plasmids results in a significant increase of the titre of viral particles, wherein e.g. the adaptation of the codon usage of the fusion protein gag-pro-pol to the human codon usage by itself leads to a titre of viral particles in human packaging cells which is higher by a factor of about 50.

The adaptation of the codon usage to the human codon usage preferably occurs by exploiting the optimal non-limited tRNA pools of homo sapiens: e.g. the glycin codon GGT was preferably adapted to GGC. Furthermore, negative RNA instability motives as well as cryptic polyadenylation sites as well as RNA secondary structures were removed, such that a more stable mRNA having better translatability in human cells was generated. Furthermore, in the coding sequence the natural splice donor site, the splice acceptor site and further cryptic splice signals were deactivated. Accordingly, a preferred helper plasmid has an inactive splice donor site in the gag-pol gene, e.g. corresponding to nucleotides 1501 to 1502 in SEQ ID NO: 14. Preferably, gag is encoded by nucleotides 1475 to 3436 of SEQ ID NO: 14 and pol is encoded by nucleotides 3738 to 6291 of SEQ ID NO: 14, since in these sections cryptic RNA instability motives and polyadenylation sites as well as RNA secondary structures have essentially been removed, such that a high titre of viral particles having a high transduction efficiency can be produced.

Finally, it is preferred in the invention that the viral vector, preferably in addition the first helper plasmid and further preferred in addition the second helper plasmid, have no sequence homologies to the target cell, and further preferred in particular have no sequence overlap, e.g. no sequence sections of more than 5 nucleotides homologous to each other, preferably no sequence sections of more than 10 to 20 nucleotides homologous to each other. In this way the probability of a recombination in packaging cells and/or in the target cells is minimized and thereby the probability of generation of RCR is minimized, too.

Accordingly, the invention provides a viral RNA which from 5' to 3' has or consists of a 5' R region and a 5' U5 region, a primer binding site (PBS), a packaging signal (Ψ) which in contrast to the state of the art of gammaretroviral or lentiviral vectors suffices without a retroviral splice donor, an expression cassette for a transgene or comprising a transgene, respectively, and a shortened 3' U3 region (marked as Δ or d) according to the invention, a 3' R region and an appending polyA section (polyA tail), as well as a vector for transcription of the viral RNA which in addition to a nucleic acid sequence encoding the viral RNA in 5' to its 5' R region has a eukaryotic or viral promoter, respectively, and in which vector the nucleic acid sequence encoding the viral RNA is present in the form of DNA which in the 3' SIN LTR has a polyA section.

Furthermore, the invention provides the use of the viral RNA and of a viral particle containing the viral RNA as a medicament and for the production of a pharmaceutical composition for use for the transduction of target cells, e.g. of somatic cells of a human, as well as pharmaceutical compositions comprising the viral RNA or viral particles containing the viral RNA, and the use of such pharmaceutical compositions as a medicament for the transfer of the transgene into cells, especially for gene therapy.

Furthermore, the invention relates to cells having an integrated or non-integrated nucleic acid sequence which are produced by contacting with viral particles according to the invention and which contain a U3 region according to the invention, e.g. a DNA section resulting from reverse transcription from a viral RNA according to the invention. These can be extracorporeal animal cells or intracorporeal animal cells, with the exception of human gametes.

The expression cassette has a promoter and at least one transcribable and/or translatable sequence of a transgene, which can be a gene homologous or heterologous to the target cell, and preferably upstream of the transcribable sequence of the transgene a PRE or other posttranscriptional regulatory nucleic acid sections or nucleic acid modules. The transcribable sequence can also have internal ribosome entry sites (IRES) in combination with protein encoding sequences arranged downstream to these, as well as other functional nucleic acid sections or enzyme encoding nucleic acid sections (e.g. bidirectional promoters, coding sequences for 2A protease cutting sites or 2A protease genes). Further optionally, an insulator sequence can be inserted into the deleted 3' U3 region. e.g. into the restriction site contained therein, which weakens an interaction of the transgene with adjacent genomic sequences, or a recombinase recognition sequence can be inserted, e.g. a recognition sequence from the group comprising rox, loxP, FRT. After reverse transcription and copying into the 5' LTR has occurred, the recombinase recognition sequence can be activated by addition and expression of recombinase in target cells, respectively, and e.g. a nucleic acid section in the integrated DNA (e.g. a portion of the expression cassette) arranged between recombinase recognition sequences can be turned around or removed. Other sequences which can be inserted into the 3' U3 region for example comprise micro-RNA target sequences, small hairpin RNAs or sequence sections which make the detection of the insertion by PCR easier.

The deleted U3 region contained in the 3' SIN LTR according to the invention in spite of the deletion of the enhancer and promoter elements from the wild-type U3 region allows the generation of viral particles having titres which are achieved comparatively to the titres for vectors having wild-type LTR in packaging cells, so that the drastic reductions of the viral titre frequently observed upon deletions of U3 regions are avoided.

The transcription of transgenes which are arranged in the expression cassette is controlled by the promoter of the expression cassette which is also termed an internal promoter. Presently it is assumed that the deleted U3 regions according to the invention have a polyA signal which avoids a through-transcription beyond the vector sequence and uses the correct polyA signal. This assumption is supported by the 3-fold improved expression of a transgene of the expression cassette of a vector according to the invention in comparison to the expression of the transgene from a vector having a 3' LTR of the wild-type.

Particularly preferred, the nucleic acid sequence of the viral vector according to the invention has a complete deletion of the sequences encoding viral structural proteins including the splice donor site (SD), e.g. a complete deletion of the sequences gag, env, pol and src. It has been found that with ASLV vectors having a deletion of the sequences encoding the viral structural proteins also the splice donor site is deleted. Surprisingly, it has been found that such a vector on the basis of ASLV allows the packaging of the viral RNA in packaging cells by means of the split-packaging system. This is unexpected insofar as in known retroviral vectors portions of the coding viral sequences are required for the packaging, since in the region of the sequences encoding the viral structural proteins signals are contained for the RNA export, for the interaction with the viral nucleocapsid and for the reverse transcription, as e.g. in HIV. Therefore, the vector according to the invention can contain the packaging signal (Ψ) which is comprised in SEQ ID No: 5 by the nucleotides 1042-1292 without sections of sequences encoding viral structural proteins.

According to the invention the preferred embodiment in which the nucleic acid sequence of the viral vector has no viral splice donor is an important difference to known lentiviral or γ-retroviral vectors which have the natural viral splice donor upstream of the primer binding site. These known vectors require the splice donor for the generation of high titres of viral particles. Surprisingly, it has been found that the vector according to the invention results in high titres in packaging cells even without its natural or another splice donor. Since the natural splice donor of ASLV is located in the gag gene, its complete deletion consequently leads to the removal of the splice donor. Further preferred according to the invention also the viral splice acceptor is not contained in the vector. The splice acceptor of ASLV is located in the pol gene, so that its complete deletion also leads to the removal of the splice acceptor.

For the vector according to the invention the deletion of splice donor and splice acceptor leads to the optimisation of the production of viral particles in packaging cells and in addition gives a better biological safety to the vector, since the recombination to replication-competent retroviruses is made more difficult. Also a possible interference with cellular splice signals is less probable in intragenic insertions of the vector.

Particularly preferred, the vector in the 5' region has an R region, a U5 region and the packaging signal in a nucleic acid sequence which does not encode viral structural proteins and to which in 3' the expression cassette of the transgene adjoins e.g. directly, especially following the leader region. It has been found that the viral vector at its 5' terminus can have an R region, a U5 region and a packaging signal which is comprised or consists of nucleotides No. 1042 to 1292 of SEQ ID NO: 5, wherein preferably in 3' adjacent to this sequence the expression cassette having the transgene is arranged.

For the purposes of the invention the arrangements of genetic elements are given in 5' to 3', as long as not described differently; nucleotide sequences are given from 5' to 3'.

DETAILED DESCRIPTION OF THE INVENTION

Figure 2:
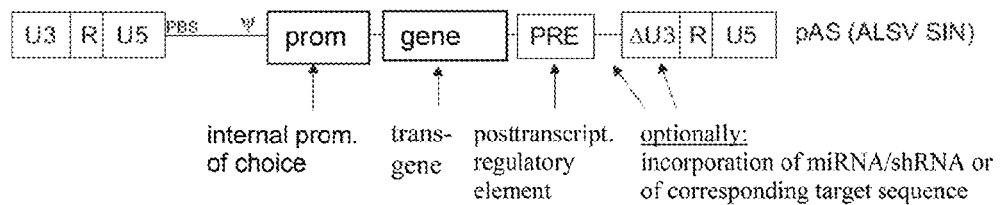
Figure 3:
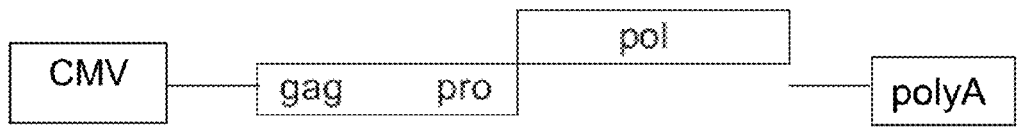
Figure 4:
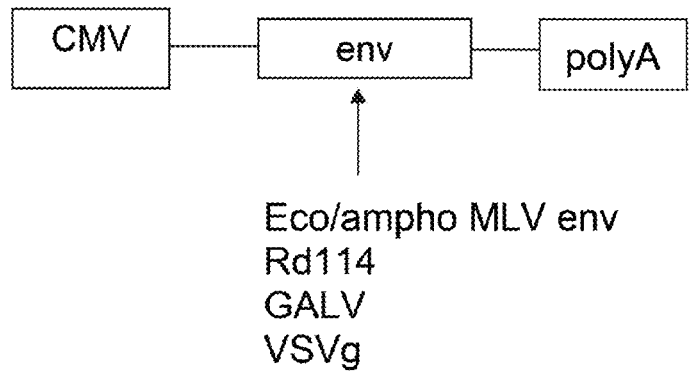
Figure 6:
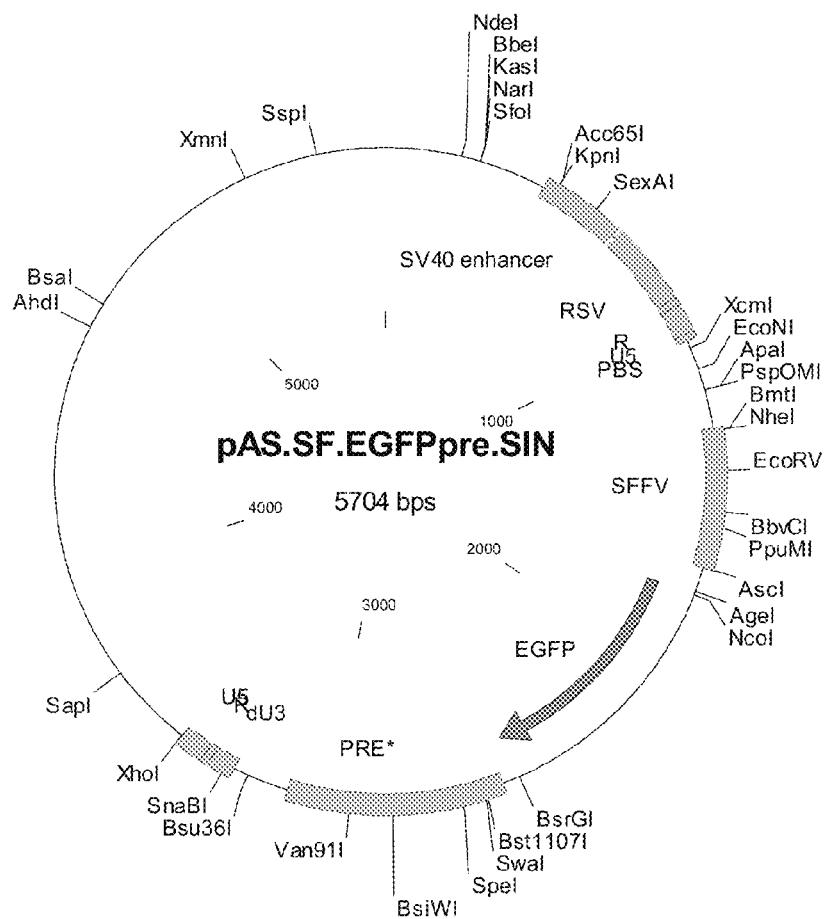
Figure 7:
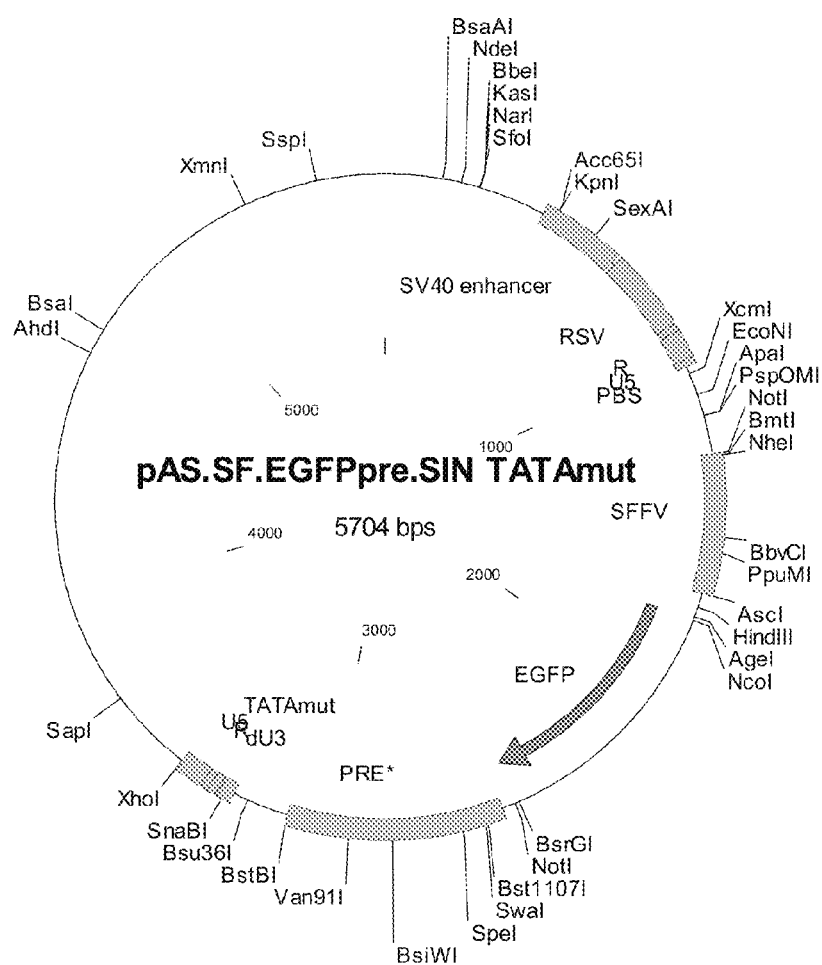
Figure 8:
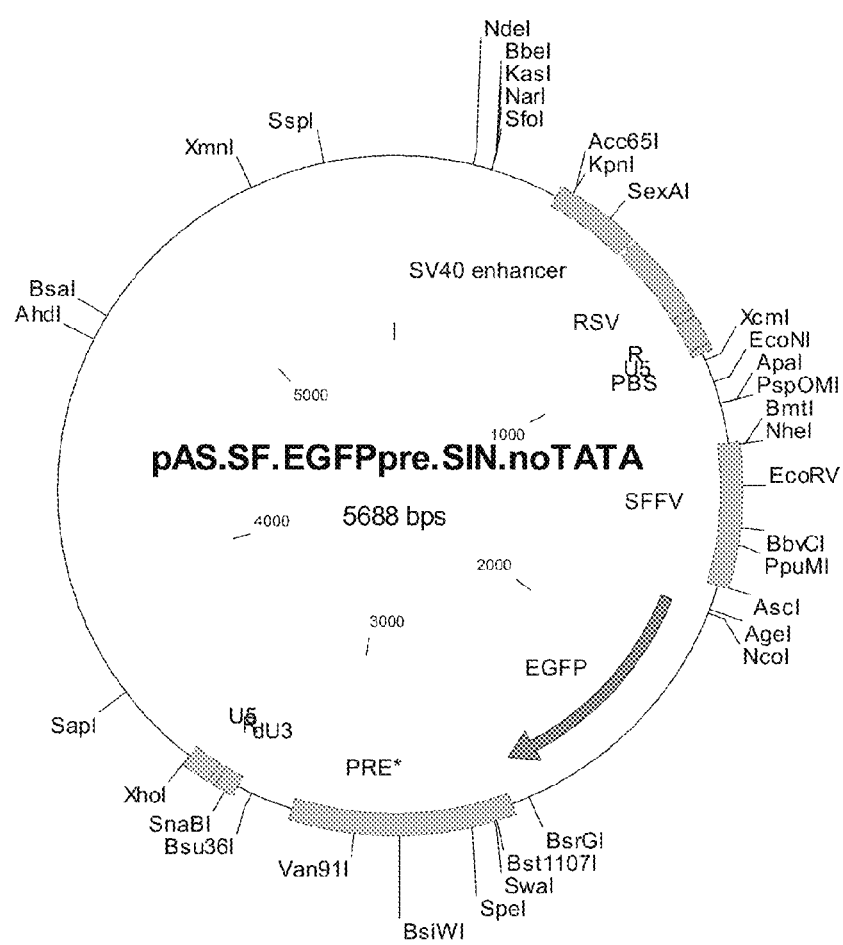
Figure 9:
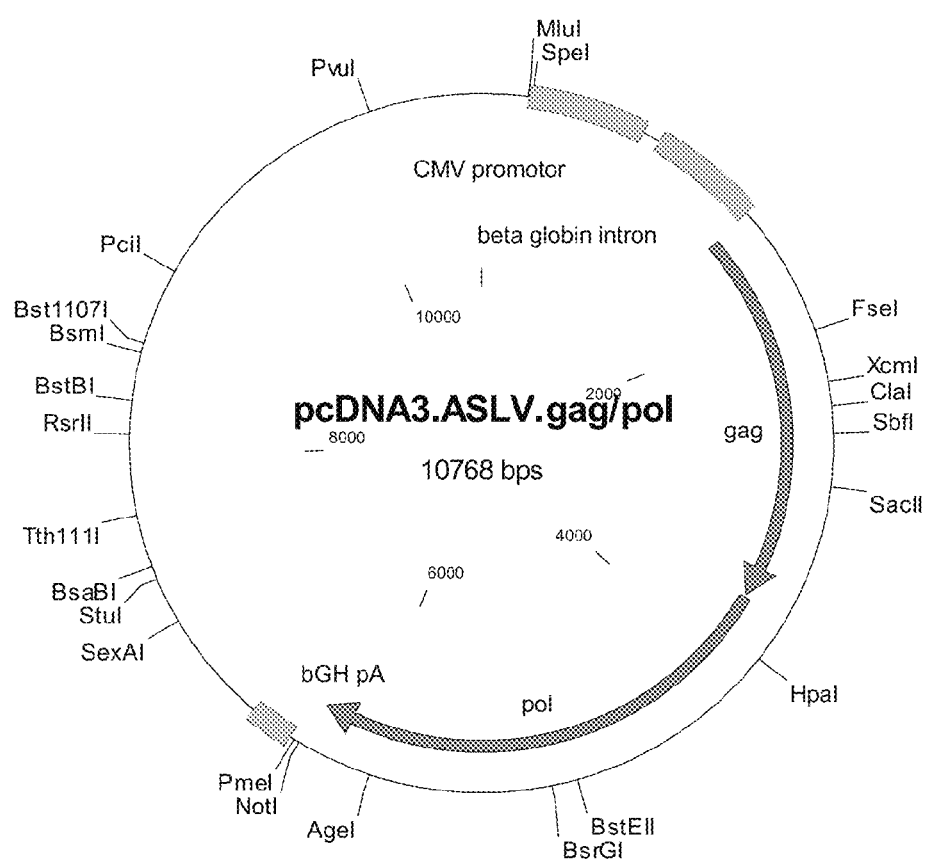
Figure 10:
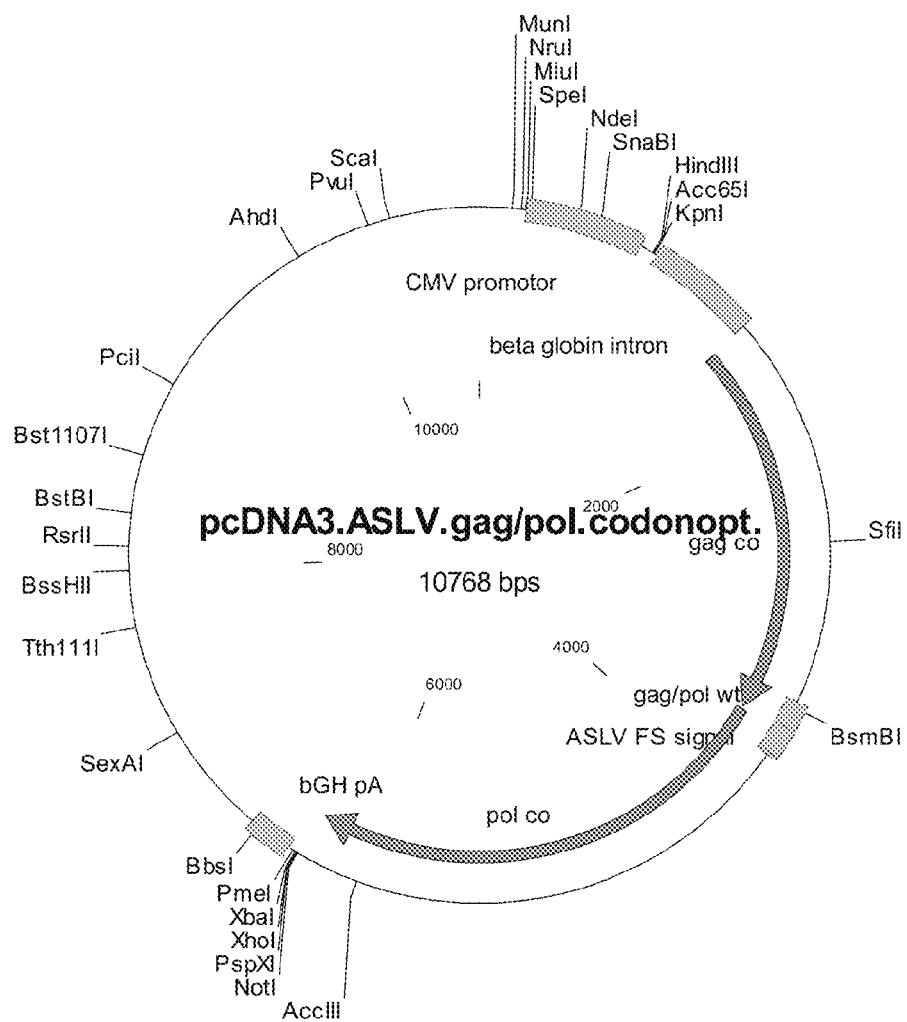
Figure 11:
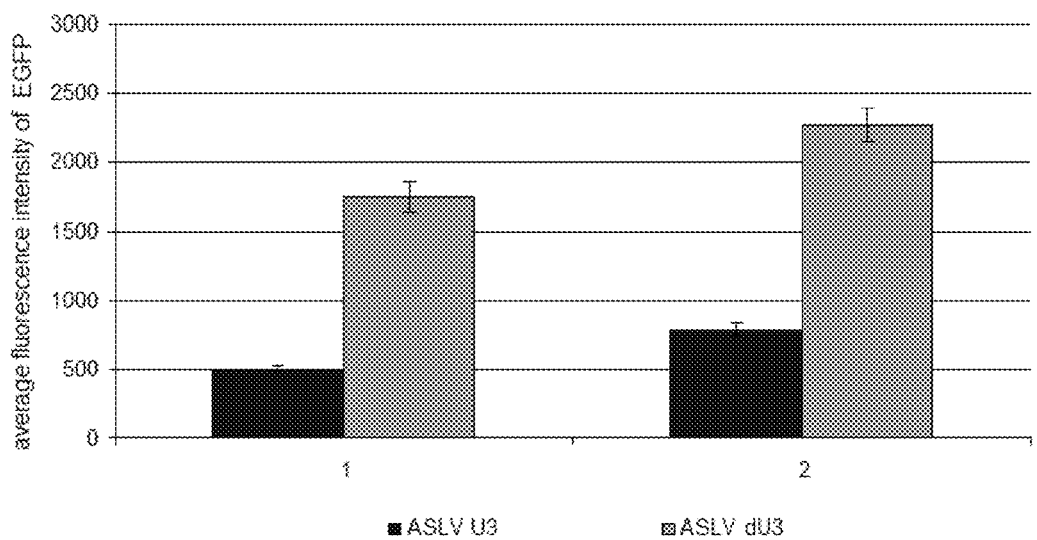
Figure 12:
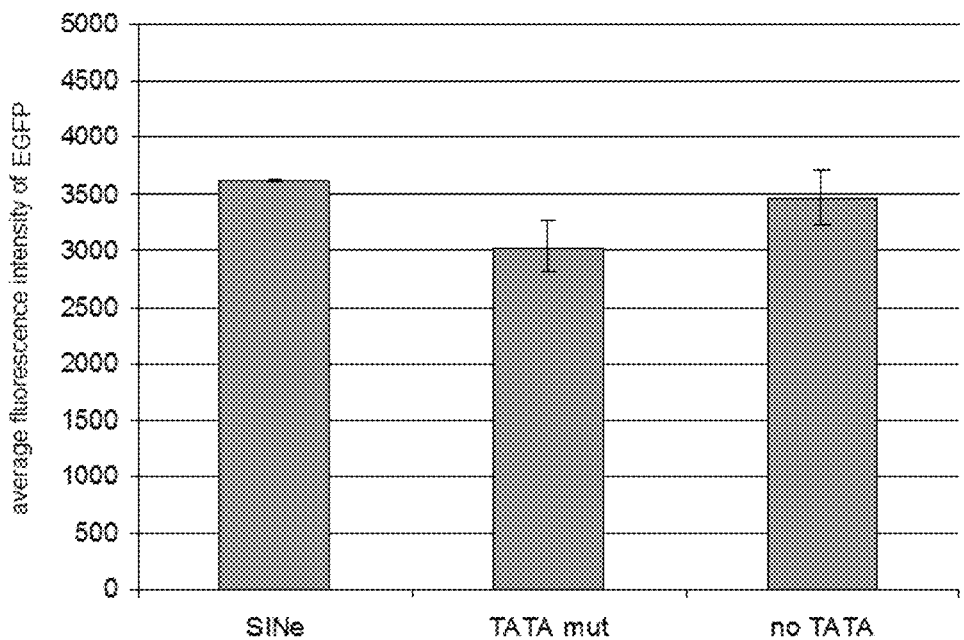
Figure 13:
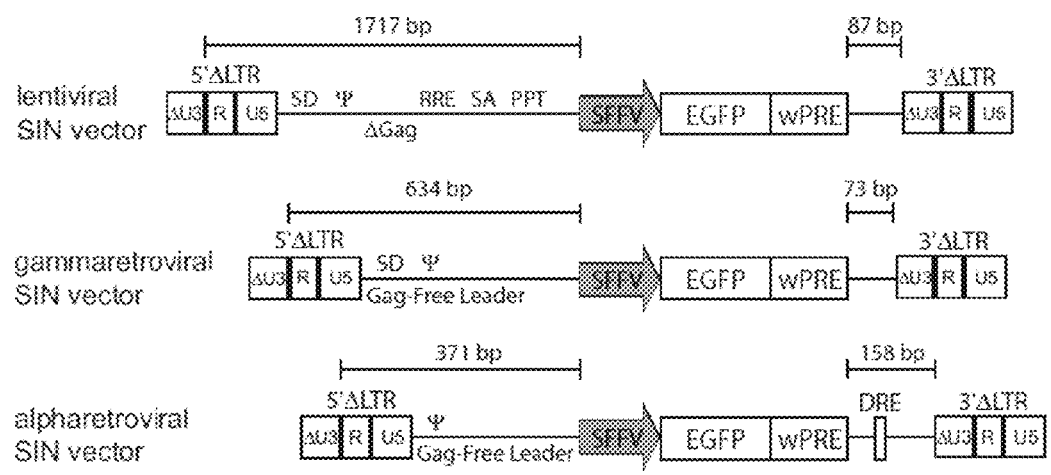
Figure 14:
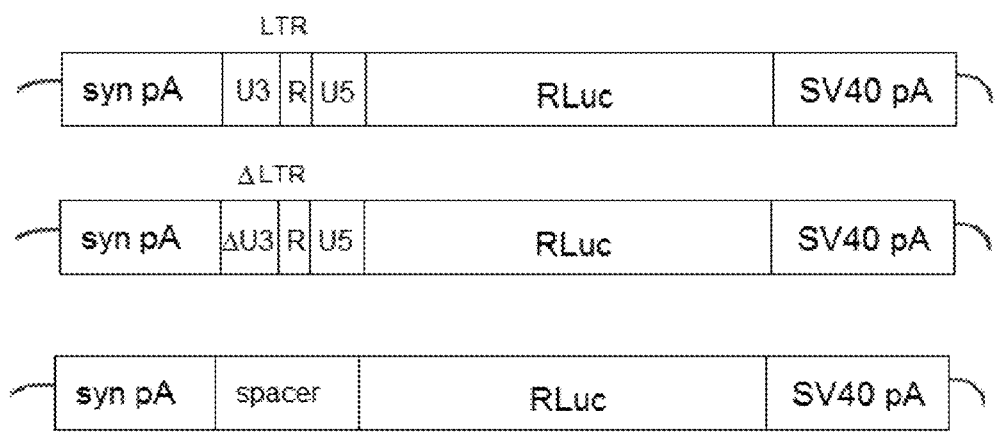
Figure 15:
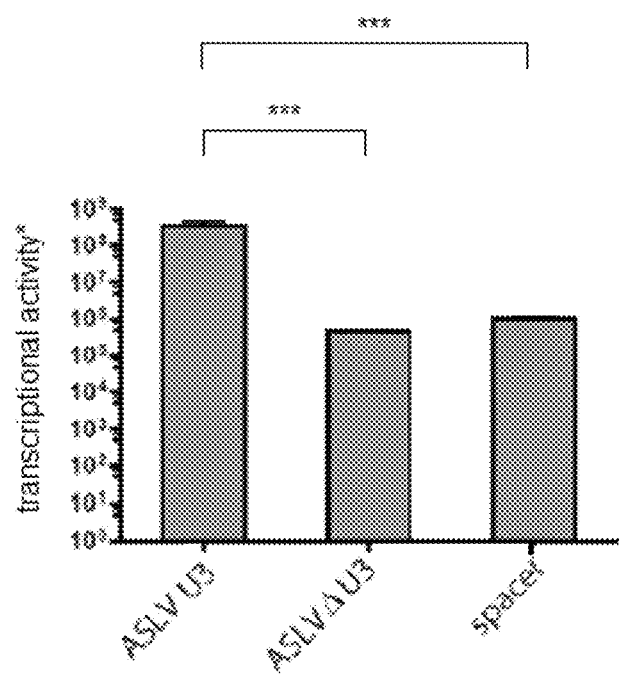

The invention is now described in greater detail by way of Examples with reference to the Figures in which FIG. 1 shows the schematic structure of the ASLV wild-type, FIG. 2 shows the schematic structure of a SIN vector according to the invention and of a plasmid containing the vector, FIG. 3 shows the schematic structure of a first helper plasmid, FIG. 4 shows the schematic structure of a second helper plasmid, FIG. 5 shows a comparison of the wild-type U3 region (U3, SEQ ID NO: 1) to the deleted U3 region (dU3, SEQ ID NO: 2) according to the invention, to the deleted U3 region according to the invention without TATA box (dU3 noTATA, SEQ ID NO: 4) and to the deleted U3 region according to the invention having a mutated TATA box (dU3 TATAmut, SEQ ID NO: 3), FIG. 6 shows a plasmid map of a vector (SEQ ID NO: 5) according to the invention in which the expression cassette encodes EGFP (SEQ ID NO: 6) as an example for a transgene, FIG. 7 shows a plasmid map comprising the vector (SEQ ID NO: 9) according to the invention in which the TATA box of the U3 region is mutated, FIG. 8 shows a plasmid map comprising the vector (SEQ ID NO: 7) according to the invention in the U3 region of which additionally the TATA box is deleted, FIG. 9 shows a plasmid map for a first helper plasmid (SEQ ID NO: 11) for translation of the gag-pol fusion protein, FIG. 10 shows a plasmid map for a first helper plasmid (SEQ ID NO: 14) in which the sequence encoding the gag-pol fusion protein is codon-optimized for a human packaging cell and/or target cell, FIG. 11 graphically shows the level of the expression of a transgene (EGFP) from the vector according to the invention in comparison to the expression from a viral vector having a wild-type 3' LTR, FIG. 12 graphically shows the level of expression of a transgene (EGFP) from SIN vectors according to the invention, FIG. 13 shows a depiction of the integrated structure of a vector according to the invention in comparison to the structure of a lentiviral and γ-retroviral SIN vector, respectively, FIG. 14 schematically shows DNA nucleic acid constructs for the transcription of viral RNA having expression cassettes which functionally contains the nucleic acid sequence to be tested for promoter activity and enhancer activity in 5' to a reporter gene, and FIG. 15 shows the level of expression of the reporter gene in cells which are transfected with viral RNA of FIG. 14 and measures the promoter activity/enhancer activity.

In the description of the SIN U3 according to the invention the numbering of the nucleotides is carried out with reference to the nucleotide sequence of the wild-type U3 of ASLV and correspondingly, deletions and sections of the SIN U3 region, respectively, are denoted according to the numbering of the nucleotides of the wild-type U3.

FIG. 1 shows the schematic structure of the ASLV of the wild-type in which the LTRs contain an U3 region, an R region and a U5 region adjacent to each other. The LTRs are identical each time, since in the viral replication the U3 region of the 3' LTR is copied to the 5' terminus and the regions R and U5 of 5' LTR are copied into the 3' LTR. The transcription start +1 defines the 5' terminus of the 5' R region.

FIG. 2 shows the vector according to the invention at plasmid level at the 5' terminus of which a promoter is arranged ahead of the R region in order to enable the transcription starting from the 5' R region. This 5' promoter of the 5' LTR due to the transcription start at +1 as first nucleotide of the 5' R region is not contained in the viral RNA; the viral RNA which is produced consists of the regions between the nucleotide +1 of the 5' R region and the 3' terminus of the 3' R region plus polyA tail. Correspondingly, viral particles contain a viral RNA which is generated from that section of the vector which comprises the 5' R region (including nucleotide +1) up to the 3' terminus of the 3' R region with an appending polyA tail. The promoter of the viral vector upstream of the 5' R region shown in FIG. 2 which preferably consists of an SV40 enhancer and of a U3 region of the wild-type of the RSV (Rous Sarcoma Virus) does not become a component of the viral RNA, but controls the efficient transcription of the viral RNA of a DNA sequence corresponding to FIG. 2. In the present case the vector is shown at the plasmid level as a DNA sequence encoding the viral RNA which can be a component of a plasmid from which the viral RNA is transcribed.

As indicated in FIG. 2, the viral vector between the LTRs and correspondingly after the leader region contains an expression cassette which comprises at least one internal promoter, for example the promoter of SFFV and EFS (elongation factor, 1α) having a nucleotide sequence encoding a transgene (gene), preferably having a PRE arranged in 3'.

The PRE which preferably is WPRE of the expression cassette preferably has an X-ORF deletion and/or ATG mutations.

The vector according to the invention and the viral RNA according to the invention at least in the 3' LTR have a U3 region having deletions which deactivate any promoter activity of the LTR. In 5' to the 3' SIN LTR and/or within the 3' U3 region the viral vector according to the invention can contain homologous and/or heterologous genetic elements, for example sequences which comprise miRNA, shRNA, polyadenylation enhancers, recombinase recognition sequences, USE and/or insulators.

Between the elements of the 5' LTR and the 3' LTR, preferably between the regions of the 5' LTR and the expression cassette, the vector according to the invention preferably has a primer binding site and a packaging signal (Ψ).

In contrast to replication competent retroviruses the viral vector according to the invention has no sequences coding for gag-pol and/or envelope proteins.

The viral proteins which are necessary for the generation of a viral particle of the viral RNA are encoded by separate helper plasmids, preferably by a first helper plasmid which has a coding sequence for the gag-pro-pol fusion protein in an expression cassette between a promoter and a polyadenylation sequence, as depicted in FIG. 3, and by a second helper plasmid containing a sequence encoding the envelope protein (env) in an expression cassette, for example as depicted in FIG. 4 between a promoter of CMV (cytomegalovirus) and a polyadenylation sequence. For pseudotypification the sequence encoding the envelope protein can consist of a sequence encoding the envelope protein of MLV Ecotrop/Amphotrop, VSVg, RD114, GALV or chimaera of these, e.g. RD114/TR.

The first helper plasmid in its coding sequence preferably comprises the reading frame shift of −1 between the 3' terminus of the sequence encoding gag-pro and the 5' terminus of the sequence encoding pol, which is shown in FIG. 3 for gag-pro and pol, respectively, by the staggered boxes.

Particularly preferred, the coding sequences of the helper plasmids are adapted to the codon usage of the target cell, i.e. codon-optimized, since it has been found for the invention that this codon-optimization for the gag-pro-pol fusion protein, preferably also for the envelope protein env, results in an increase of the titre in helper cells approximately by the factor of 50. Therefore, the invention enables a production method in titres and amounts of viral particles, respectively, as they are required for clinical applications, by production of viral particles containing the viral RNA according to the invention, by a first helper plasmid and a second helper plasmid, e.g. by culturing of a packaging cell.

FIG. 5 shows an overview of the preferred sequences of the 3' U3 region of the viral vector according to the invention in comparison to the sequence of the wild-type U3 (SEQ ID NO: 1) of ASLV. The U3 regions according to the invention preferably have a deletion of the nucleotides 28-186 of the wild-type U3. The embodiment SEQ ID NO: 2, denoted as Delta (d) U3, preferably consists of the nucleotides 1-27 and of the nucleotides 187-229 of the wild-type U3, wherein the nucleotides 187 and 189 are further mutated to C and T, respectively, such that a restriction site for SnaBI (TACGTA) results there. This deleted U3 region, also denoted as SIN U3, still has the initial TATA box which was identified as nucleotides 200-206 of the wild-type U3.

In a preferred embodiment the TATA box of the SIN U3 is mutated, too, such that the function of a TATA box is annulled. A preferred embodiment of a mutated TATA box is shown in SEQ ID NO:3 (TdU3 TATAmut) in which the nucleotides 201-203 are mutated, such that the function of the TATA box is destroyed.

In a preferred embodiment the deletion with respect to the wild-type U3 region comprises the nucleotides 28-205 (dU3 noTATA; SEQ ID NO: 4), wherein the nucleotides 203-204 are mutated in order to avoid the generation of a TATA box by the adjoining sections and/or in order to generate a cutting site at the adjoining nucleotides 26-27 and 203-206, for example by mutation of the nucleotides 203-205 to CGT in order to generate a singular cutting site for the restriction enzyme SnaBI (TACGTA).

Viral vectors according to the invention therefore also comprise variants in which in the region of the deletion of nucleotides 28-222, preferably in the region of the nucleotides 28-190 and 28-206 in SEQ ID NO: 1, respectively, heterologous or homologous, e.g. genetic elements heterologous or homologous with respect to the target cell, can be inserted, preferably by means of a restriction site in the aforementioned sections.

Example 1

Production of Viral Particles Having an ASLV SIN Vector According to the Invention As examples for vectors according to the invention coding for a viral RNA according to the invention plasmids were constructed which under the control of a promoter of an enhancer element of SV40 (SV40 enhancer) and the RSV promoter (RSV) directly adjacent to the promoter had the R region, the U5 region, an expression cassette for a transgene and a 3' SIN LTR from a SIN U3 region according to the invention, an R region and a U5 region. The expression cassette comprised the U3 promoter of the spleen focus-forming virus (SFFV), a sequence coding for EGFP as an example for a transgene, and a WPRE (PRE).

For the vector shown in FIG. 6, the SIN U3 region corresponded to the SEQ ID NO: 2, alternatively to the SEQ ID No: 3 for the vector shown in FIG. 7, and corresponded to the SEQ ID NO: 4 for the vector shown in FIG. 8, respectively.

The sequence of the vector of FIG. 6 is contained as SEQ ID NO: 5. Correspondingly, a vector according to the invention and a plasmid encoding an RNA according to the invention, respectively, contains a 3' SIN LTR having a sequence corresponding to nucleotides 3282-3452 of SEQ ID NO: 5. The viral RNA transcribed therefrom contains the 3' U3 region according to the invention contained therein.

The sequence of the vector of FIG. 7 is contained as SEQ ID NO: 9. Correspondingly, a vector according to the invention from which a viral RNA according to the invention is transcribed contains a 3' SIN LTR having a sequence corresponding to the nucleotides 3282-3452 of SEQ ID NO: 9. The viral RNA contains the 3' U3 region and R region according to the invention at the 3' SIN LTR, but not the U5 region.

The sequence of the vector of FIG. 8 is contained as SEQ ID NO: 7. Correspondingly, a vector according to the invention from which a viral RNA according to the invention is transcribed contains a 3' SIN LTR having a sequence corresponding to the nucleotides 3282-3436 of SEQ ID NO: 7.

Further preferred, a viral vector and a viral RNA, respectively, in the form in which the nucleotide sequence for the viral RNA is contained on a plasmid, contain a wild-type R region and a wild-type U5 region as the 5' LTR and directly adjacent thereto in 5' a eukaryotic or viral promoter, preferably the enhancer sequence from SV40 in combination with the promoter from RSV, corresponding to nucleotides 452-921 of SEQ ID NO: 9.

The sequence of SEQ ID NO: 5 coding for eGFP is given as amino acid sequence SEQ ID NO: 6, eGFP of SEQ ID NO: 7 as SEQ ID NO: 8, and eGFP of SEQ ID NO: 9 as SEQ ID NO: 10.

For generation of viral particles the plasmids according to FIGS. 6 to 8 were introduced into HEK293T cells which also contained a first helper plasmid for expression of the gag-pol fusion protein of ASLV by means of transient transfection or stable integration. A schematic plasmid map is shown in FIG. 9, the sequence is contained as SEQ ID NO: 11 and contains the gag-pol fusion protein at nucleotides 1475-6291 as coding sequence. The amino acid sequence of gag encoded by SEQ ID NO: 11 corresponds to SEQ ID NO: 12, the one of poi encoded by SEQ ID NO: 11 corresponds to SEQ ID NO: 13.

Particularly preferred, the first helper plasmid was provided with a coding sequence for the gag-pol fusion protein the codons of which were adapted to the codon usage of the packaging cell, especially of mammalian cells, as e.g. human cells. Such a plasmid is schematically shown in FIG. 10; the nucleic acid sequence is contained as SEQ ID NO: 14. Correspondingly, a preferred first helper plasmid and a human packaging cell, respectively, in integrated form contain the coding sequence for the codon-optimized gag protein corresponding to nucleotides 1475-3436 of SEQ ID NO: 14, the amino acid sequence of which corresponds to SEQ ID NO: 15, and/or the coding sequence for the codon-optimized pol protein corresponding to nucleotides 3738-6291 of SEQ ID NO: 14, the amino acid sequence of which corresponds to SEQ ID NO: 16, preferably the coding sequence for the codon-optimized gag-pol fusion protein corresponding to nucleotides 1475-6291 of SEQ ID NO: 14.

Under usual cultivation conditions of the packaging cell the same titres were obtained each time for the viral particles according to the invention having one of the SIN U3 regions shown of the vectors of SEQ ID NO: 7, 9 or 11, as for a comparative construct (not shown) in which the 3' U3 region corresponded to the wild-type of ASLV, namely approximately $1 \times 10^6$/mL.

It is therefore preferred for the method for production of viral particles according to the invention that the packaging cells are cultured human cells having a nucleic acid sequence encoding the viral structural genes, e.g. gag-pol, having human codon usage, wherein these structural genes preferably have no active splice donor site and/or splice acceptor site, in order to avoid a splicing within the coding sequences and to thereby achieve a high expression in the packaging cells.

For control of the transfection of target cells with viral RNA human HT1080 fibroblasts were infected. Subsequent to the cultivation after the transfection the expression of the transgene (EGFP) was determined by FACS. In the comparison to viral particles the 3' LTR of which was of wild-type ASLV, an expression of the transgene higher by the factor of 3 could be shown for the viral vectors having 3' SIN LTR according to the invention.

FIG. 11 shows the expression of the exemplary transgene EGFP by an expression cassette according to FIG. 7 in target cells which were transduced with viral vector. Viral particles were obtained from the supernatant of packaging cells (pseudotyped with VSVg) which contained a plasmid encoding viral RNA according to SEQ ID NO: 5 according to the invention (ASLV dU3, bright right bars), and a viral RNA having a 3' U3 of the wild-type (ASLV U3, dark left bars; wild-type U3 see SEQ ID NO:1). For transduction viral particles were titrated onto HT1080E cells, cultivated for 6 days and analysed flow-cytometrically subsequently. In Experiment 1 the gag-pol fusion protein was of the wild-type (nucleotides No. 1475 to 6291 in SEQ ID NO: 11), in Experiment 2 it was codon-optimized (nucleotides No. 1475 to 6291 in SEQ ID NO: 14). The result was that the viral particle according to the invention having a 3' U3 region according to the invention in comparison to the viral particle having a U3 region of the wild-type resulted in a 3-fold higher expression of the transgene in target cells. This applies both to the use of the wild-type gag/pol (Experiment 1) and to the codon-optimized gag/pol helper plasmid (Experiment 2). In both cases an approximately 3-fold increase of the expression of the transgene in target cells results for viral particles according to the invention (dU3) in comparison to the wild-type comparative particles (U3).

|  | average fluorescence intensity | |
| --- | --- | --- |
| experiment | ASLV U3 | ASLV dU3 |
| 1 (wild-type gag-pol) | 503.8 +/− 15.1 | 1748.2 +/− 112.6 |
| 2 (codon-optimized gag-pol) | 791.3 +/− 48.7 | 2275.6 +/− 120.6 |

FIG. 12 shows the values of the expression of the exemplary transgene EGFP by an expression cassette in target cells transduced with viral vector which contained viral RNA transcribed from a plasmid according to SEQ ID NO: 5 (SIN, according to the invention), SEQ ID NO: 9 (TATAmut), and SEQ ID NO: 7 (noTATA), respectively. As described above, viral particles were generated in packaging cells which translated codon-optimized gag-pol fusion protein and VSVg envelope protein. HT1080 cells were transduced with viral particles, cultivated for 6 days, and then analysed by FACS. The values shown make it clear that the 3' U3 region according to the invention in all viral RNAs and viral particles according to the invention, respectively, results in a high expression efficiency of the transgene in target cells. The results are also presented in the following table:

| | average fluorescence intensity |
|---|---|
| ASLV dU3 | 3616.9 +/− 15.8 |
| ASLV dU3 TATAmut | 3020.4 +/− 227.8 |
| ASLV dU3 noTATA | 3463.2 +/− 252.8 |

The preferred embodiment of the vector according to the invention, e.g. its viral RNA, optionally contained in viral particles, has no coding viral sequences, e.g. no sequences completely or partially comprising one of the structural genes gag, env, src or pol. Therefore it is preferred that the viral RNA of the vector and the transcribed nucleic acid sequence of a plasmid encoding the viral RNA of the vector, respectively, the 5' R region, the 5' U5 region and the region comprising the packaging signal and extending adjacent to the expression cassette of the transgene consist of these regions and e.g. do not contain a splice donor site. A preferred sequence for the 5' R region, the 5' U5 region and the region comprising the packaging signal and extending up to adjacent to the expression cassette of the transgene comprises the nucleotides No. 922 to 1292 of SEQ ID NO:5 or consists of this nucleotide sequence. This nucleotide sequence optionally can be shortened in 3', e.g. by 140 nt, preferably by 10 to 56 nt.

In this embodiment in which the region of the viral RNA at its 5' terminus and therefore in 5' directly adjacent to the expression cassette of the transgene, consists of non-translated sequences, especially of an R region, a U5 region and the packaging signal, therefore no sections of gag, env, src or pol are contained.

This embodiment is schematically shown in FIG. 13, making it clear that this 5' section of the vector which is also denoted as leader, is significantly shorter than the 5' region of lentiviral or γ-retroviral SIN vectors. Whereas in lentiviral and many versions of γ-retroviral SIN vectors the packaging signal Ψ overlaps with viral structural genes, in the alpharetroviral vector according to the invention, surprisingly, the packaging signal can be contained without coding viral sequence sections. Therefore, the vector according to the invention (alpharetroviral SIN vector) is denoted as a gag-free leader. Furthermore, in the vector according to the invention the viral splice donor site can be removed and made functionless by mutation, respectively. E.g. in lentiviral or γ-retroviral vectors this is possible only under reduction of the titre due to overlap with packaging functions. Furthermore, the complete removal of coding viral sequence sections allows the shortness of that section of the vector sequence which is arranged in 5' prior to the expression cassette of the transgene, e.g. of 371 nt (nucleotides, bp). Therefore, in comparison to lentiviral and γ-retroviral vectors particularly much room is generated for the intake of transgene sequences. The expression cassette in these examples consists of the strong internal promoter of SFFV, the coding sequence for green fluorescent protein (EGFP) as a reporter gene and the WPRE each time.

Example 2

Long Term Expression of the Transgene in Eukaryotic Target Cells

As an example for the use of the viral vector as a medicament, e.g. for gene therapy, blood stem cells were transduced with viral particles according to the invention. Isolated bone marrow cells from mice (strain C57BL6) were transduced with viral particles according to the invention, and for comparison with lentiviral particles. As a transgene EGFP was contained each time in the same expression cassette under the control of the SFFV promoter. Under conditions of same efficiency the cells were transfected by the lentiviral vector to 39% and therein by the factor of 1.6 more than by the vector according to the invention (24%). This can be attributed to the fact that lentiviral particles can also transduce resting, divisionally inactive cells, while the α-retroviral particles according to the invention preferably can transduce cells during the division.

The transduced blood stem cells were transplanted into 8 lethally irradiated mice of the same strain. Transduced cells were identified from peripheral blood by FACS. After 31 weeks the proportion of transduced EGFP-positive leukocytes for lentiviral vectors was increased at 32.9+/−8.9% to approximately double the value of the vectors according to the invention (16.1+/−12%).

From both groups bone marrow was taken from the animals having the highest titres of EGFP-positive cells and transplanted into 5 lethally irradiated animals of a second group each. 6 weeks after this transplantation the proportion of EGFP-positive leukocytes for the lentivirally transduced stem cells at 40.6+/−5.9 still was approximately 30% above the Proportion of transduced stem cells according to the invention (32.6+/−8.1%). This shows that the velocity of the epigenetic shutdown of the expression of the transgene for the vectors according to the invention is not essentially higher than for lentiviral vectors.

Example 3

Demonstration of Lower Risk by Insertional Mutagenesis of the Vectors

In an in vitro test developed by the inventors (Mol. Ther. 1919-1928 (2009)) the risk of oncogene activation in the transduction and transfection by the viral vector, respectively, was examined. An oncogene activation, e.g. by insertion of viral sequences into the genomic neighbourhood, therein leads to the transformation of primary haematopoietic cells. In short it is investigated in this test in which frequency and to which degree of distinctness the insertional activation of transformation supporting cellular proto-oncogenes like EviI occurs. In this test primary haematopoietic cells of the untreated mouse, e.g. strain C57BL6, are contacted with viral particles. After this transduction the transformation frequency is determined by cultivation under conditions which cause the myeloid differentiation, wherein the renewed seeding is carried out from such cell dilutions in which non-transformed cells do not proliferate due to the inhibition of the remaining capability of division caused by the dilution, but only transformed cells proliferate. In transformed cells e.g. the expression of proto-oncogenes is up-regulated by insertional mutagenesis. This test therefore quantifies the transformation frequency in relation to transduced cells. The viability and stability of the transformants, respectively, therefore can be determined as the result of the cultivation of transformed cells after renewed seeding and replating, respectively.

It has been found therein that γ-retroviral vectors and lentiviral vectors lead to a transformation frequency of approximately $1 \times 10^{-5}$ and $5 \times 10^{-6}$, respectively (Mol. Ther. 1919-1928 (2009)). In parallel batches a transformation frequency of approximately $3.6 \times 10^{-6}$ was determined for the vectors according to the invention which accordingly was still under the value determined for lentiviral vectors. In addition to the transformation frequency the viability and fitness of the transformed cells, respectively, is analysed in this test. The value for this fitness for 3 of 4 so far isolated cells transformed by the vector according to the invention was approximately 10-fold lower than the average value for lentivirally transformed cells. These results by way of the low transformation frequency and the low fitness of cells transformed by the α-retroviral vector according to the invention show that this vector provides a better safety against the oncogene activation than the previous γ-retroviral or lentiviral vectors. The risk of insertional transformation can be reduced further by the choice of suitable internal promoter sequences.

Example 4

Determination of Deletions of the 3' U3 Region Eliminating its Promoter and Enhancer Activities The deletion and the substitution of nucleotides of the U3 region, respectively, for the reduction and elimination of the promoter and enhancer activities, respectively, preferably is determined by means of an activity test in which the expression of a reporter gene is measured which is functionally arranged in 3' to the U3 region provided with deletions. If the expression of a reporter gene which is arranged functionally in 3' to the deleted and substituted U3 region, respectively, is determined on the level of the background activity of the promoterless expressed reporter gene, the promoter activity according to the invention is eliminated. Preferably, a polyadenylation sequence is arranged in 3' to the reporter gene. As background activity of the expressed reporter gene e.g. that activity is defined which is measured without any U3 region and without any promoter in 5' of the reporter gene, respectively.

FIG. 14 schematically sectionally shows the nucleic acid constructs with which the activity test for the promoter and enhancer activities of the U3 region as deleted and substituted according to the invention, respectively, was carried out. The construct depicted in the upper part of FIG. 13 shows the luciferase gene from Renilla (RLuc) as a reporter gene which is flanked in 3' by a polyadenylation signal sequence of SV40 (SV40 pA) and in 5' by the nucleic acid sequence to be tested for promoter sequence and enhancer sequence, presently by the wild-type LTR (U3-R-U5) of ASLV. Below that, an otherwise identical construct having a deletion (ΔLTR) is shown, the U3 region of which is partially deleted (ΔU3). In this construct the nucleotides 28-186 are deleted. Further below, an otherwise identical construct is shown in which the LTR is completely substituted by a random sequence (spacer, placeholder derived from the prokaryotic β-lactamase gene). A synthetic polyadenylation signal (syn pA) is arranged in 5' to the viral sequence section.

In FIG. 15 the luciferase activities of 293T cells are shown which are transfected by the constructs of FIG. 13 and cultivated under identical conditions. The measurement of the luciferase activity was made in cell homogenates, the depiction shows relative luminescence values which were normalized to total protein and to transfection efficiency. It becomes clear that the deletion to ΔU3 (ASLV delta U3) according to the invention causes a drastic reduction (approximately by the factor 400) of the promoter activity in comparison to the wild-type LTR (ASLV U3). The data after statistical analysis are very significant to each other (**, $P<0.01$). The substitution of the LTR by the arbitrary sequence (spacer) leads to a similar reduction of the promoter activity. Therefore, according to the invention an arbitrary sequence having no known promoter and enhancer functions can be used as a sequence having background activity. It is assumed that the background activity of the luciferase which is still measured is caused by other components of the plasmid in which the expression cassette of the reporter gene is contained. Preferably, the reporter gene is adapted to the codon usage of the transfected cell.

The invention claimed is:

1. Viral RNA having a 5'-region having an R region and a U5 region from ASLV and having arranged in 3' thereto a primer binding site (PBS), a packaging signal (Ψ), an expression cassette, a 3' U3 region and an R region, wherein the 3' U3 region has a nucleotide sequence having SEQ ID NO: 1 which has a deletion of the nucleotides No. 28 to No. 186 inclusive which essentially eliminates the promoter and enhancer activities of the 3' U3 region and wherein no nucleic acid sequences are contained which at least partially encode viral structural proteins or a splice donor site (SD).

2. Viral RNA according to claim 1, wherein the promoter and enhancer activities essentially eliminated by the deletion is the background activity which is determinable as the expression of a reporter gene in transfected human cells to which reporter gene a nucleic acid sequence without promoter or enhancer sequences is arranged in 5' and a polyadenylation sequence is arranged in 3'.

3. Viral RNA according claim 1, characterized in that the 3' U3 region has a nucleotide sequence corresponding to SEQ ID NO: 1, and the nucleotides No. 200 to No. 206 are additionally mutated to a partial sequence which is no TATA box.

4. Viral RNA according to claim 3, characterized in that the nucleotides No. 200 to No. 206 are mutated to a sequence TGTCTAA.

5. Viral RNA according to claim 1, wherein the 3' U3 region has a nucleotide sequence having SEQ ID NO: 1 which has a deletion of the nucleotides No. 28 to No. 186 inclusive, and the nucleotide No. 187 is mutated to C and nucleotide No. 189 is mutated to T.

6. Viral RNA according to claim 1, characterized in that the 3' U3 region has a nucleotide sequence corresponding to SEQ ID NO: 1 from which additionally the nucleotides No. 187 to No. 202 are deleted.

7. Viral RNA according to claim 1, wherein the 3' U3 region has or consists of a sequence corresponding to SEQ ID NO: 2, SEQ ID NO: 3 or SEQ ID NO: 4.

8. Viral RNA according to claim 1, wherein the 3' U3 region including the 3' R region has or consists of a sequence corresponding to the nucleotides No. 3282 to No. 3372 of SEQ ID NO: 5, a sequence corresponding to the nucleotides No. 3282 to No. 3356 of SEQ ID NO: 7, or a sequence corresponding to the nucleotides No. 3282 to No. 3372 of SEQ ID NO: 9.

9. Viral RNA according to claim 1, wherein the 3' U3 region has a nucleic acid sequence inserted encoding miRNA, shRNA, a polyadenylation enhancer, an insulator and/or a recognition sequence for a DNA recombinase.

10. Viral RNA according to claim 1, wherein the expression cassette from 5' to 3' has a promoter, a nucleic acid sequence encoding a transgene and a PRE.

11. Viral RNA according to claim 1, wherein the nucleic acid sequence which is arranged in 5' adjacent to the promoter from 5' to 3' encodes an R element, directly adjacent to that a U5 element and a packaging signal (Ψ).

12. Viral RNA according to claim 1, wherein the nucleic acid sequence arranged in 5' to the expression cassette has or consists of the sequence of the nucleotides No. 922 to 1292 of SEQ ID NO: 5.

13. DNA sequence having a promoter element which is arranged functionally in 5' to a nucleotide sequence encoding viral RNA, wherein the nucleotide sequence encoding the viral RNA has a sequence according to claim 1.

14. DNA sequence according to claim 13, wherein the nucleotide sequence encoding the viral RNA has a 5' R region and a 5' U5 region having a sequence corresponding to nucleotides No. 922 to 1022 of SEQ ID NO: 5 and in 3' thereto a 3' LTR having a sequence corresponding to nucleotides No. 3282 to 3452 of SEQ ID NO: 5 or having a sequence corresponding to nucleotides No. 3282 to 3436 of SEQ ID NO: 7 or having a sequence corresponding to nucleotides No. 3282 to 3452 of SEQ ID NO: 9.

15. A viral particle having an envelope protein, wherein the particle has a viral RNA according to claim 1.

16. A pharmaceutical composition for use in gene therapy, wherein a viral particle is according to claim 15.

17. A kit for the generation of retroviral particles having a DNA sequence encoding a viral RNA, having a first helper plasmid encoding a gag-pro-pol fusion protein and having a second helper plasmid encoding a viral envelope protein, characterized in that the viral RNA has a nucleotide sequence according to one of the claim 1.

18. A kit according to claim 17, characterized in that the DNA sequence encoding a viral RNA, the first helper plasmid and/or the second helper plasmid are transfected into a eukaryotic cell or are integrated into the genome of a eukaryotic cell.

19. A kit according to claim 17, characterized in that the first helper plasmid encodes the gag-pro-pol fusion protein and/or the second helper plasmid encodes the viral envelope protein by codons which are adapted to the codon usage of the eukaryotic cell containing them.

20. A kit according to claim 17, characterized in that the first helper plasmid encodes the gag-pro-pol fusion protein by a nucleotide sequence corresponding to nucleotides No. 1475 to No. 6291 of SEQ ID NO: 14.

21. A method for the production of viral particles by expression of a gag-pro-pol fusion protein and of a viral envelope protein in a packaging cell, characterized in that the viral RNA is transcribed from a DNA sequence having a nucleotide sequence according to claim 1.

22. A viral particle according to claim 15 for use as a pharmaceutical composition.

23. The viral particle according to claim 22, wherein the pharmaceutical composition is for use as a medicament for the genetic modification of somatic adult cells, of haematopoietic stem cells or of non-human embryonic stem cells.

24. Viral RNA according to claim 1, which has an integrase attachment site in nucleotides 1-25 of SEQ ID NO: 1.

25. The viral particle of claim 15, wherein said viral RNA has an integrase attachment site in nucleotides 1-25 of SEQ ID NO: 1.

26. A pharmaceutical composition for use in gene therapy and comprising the viral particle of claim 25.

27. A viral RNA having a 5'-region having an R region and a U5 region from ASLV and having arranged in 3' thereto a primer binding site (PBS), a packaging signal (Ψ), an expression cassette, a 3' U3 region and an R region, wherein the 3' U3 region has a nucleotide sequence having SEQ ID NO: 1 which has an integrase attachment site in nucleotides 1-25 of SEQ ID NO: 1 and which has a deletion of the nucleotides No. 28 to No. 186 of SEQ ID NO: 1, said deletion essentially eliminates the promoter and enhancer activities of the 3' U3 region, and wherein said viral RNA contains no nucleic acid sequences which at least partially encode viral structural proteins or a splice donor site (SD).

\* \* \* \* \*

SEQUENCE LISTING

<160> NUMBER OF SEQ ID NOS: 16

<210> SEQ ID NO 1
<211> LENGTH: 229
<212> TYPE: DNA
<213> ORGANISM: Avian sarcoma virus
<220> FEATURE:
<221> NAME/KEY: misc_feature
<222> LOCATION: (1)..(229)
<223> OTHER INFORMATION: SEQ ID NO: 1: 3?-U3-region Wild-type ASLV

<400> SEQUENCE: 1

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
ccgcattgca gagatattgt atttaagtgc ctagctcgat acaataaac                  229
```

<210> SEQ ID NO 2
<211> LENGTH: 70
<212> TYPE: DNA
<213> ORGANISM: Artificial Sequence
<220> FEATURE:
<223> OTHER INFORMATION: /note="SEQ ID NO: 2: U3-region with deletion"

<400> SEQUENCE: 2

```
aatgtagtct tatgcaatac tcttgtacgt agagatattg tatttaagtg cctagctcga    60
tacaataaac                                                            70
```

<210> SEQ ID NO 3
<211> LENGTH: 70
<212> TYPE: DNA
<213> ORGANISM: Artificial Sequence
<220> FEATURE:
<223> OTHER INFORMATION: /note="SEQ ID NO: 3: U3-Region with deletion"

<400> SEQUENCE: 3

```
aatgtagtct tatgcaatac tcttgtacgt agagatattg tgtctaagtg cctagctcga    60
tacaataaac                                                            70
```

<210> SEQ ID NO 4
<211> LENGTH: 54
<212> TYPE: DNA
<213> ORGANISM: Artificial Sequence
<220> FEATURE:
<223> OTHER INFORMATION: /note="SEQ ID NO: 4: U3-Region with deletion"

<400> SEQUENCE: 4

```
aatgtagtct tatgcaatac tcttgtacgt agtgcctagc tcgatacaat aaac          54
```

<210> SEQ ID NO 5
<211> LENGTH: 5704
<212> TYPE: DNA
<213> ORGANISM: Artificial Sequence
<220> FEATURE:
<223> OTHER INFORMATION: /note="SEQ ID NO:. 5: viral vector with
      deleted U3-Region"
<220> FEATURE:
<221> NAME/KEY: enhancer
<222> LOCATION: (452)..(684)
<223> OTHER INFORMATION: SV40 enhancer
<220> FEATURE:
<221> NAME/KEY: promoter
<222> LOCATION: (693)..(921)
<223> OTHER INFORMATION: RSV promoter
<220> FEATURE:
<221> NAME/KEY: misc_feature
<222> LOCATION: (922)..(942)
<223> OTHER INFORMATION: 5?- LTR: R-region
<220> FEATURE:
<221> NAME/KEY: misc_feature
<222> LOCATION: (943)..(1022)
<223> OTHER INFORMATION: 5?- LTR: U5-region
<220> FEATURE:
<221> NAME/KEY: PBS
<222> LOCATION: (1023)..(1041)
<223> OTHER INFORMATION: primer binding site
<220> FEATURE:
<221> NAME/KEY: promoter
<222> LOCATION: (1293)..(1684)
<223> OTHER INFORMATION: internal promoter of the expression cassette:
      SFFV
<220> FEATURE:
<221> NAME/KEY: CDS
<222> LOCATION: (1764)..(2483)
<223> OTHER INFORMATION: EGFP: coding sequence for eGFP
<220> FEATURE:
<221> NAME/KEY: misc_feature
<222> LOCATION: (2522)..(3124)
<223> OTHER INFORMATION: PRE of the expression cassette
<220> FEATURE:
<221> NAME/KEY: misc_feature
<222> LOCATION: (3282)..(3351)
<223> OTHER INFORMATION: 3?-U3: U3-region with deletion
<220> FEATURE:
<221> NAME/KEY: misc_feature
<222> LOCATION: (3352)..(3372)
<223> OTHER INFORMATION: 3?- R-region
<220> FEATURE:

<221> NAME/KEY: misc_feature
<222> LOCATION: (3373)..(3452)
<223> OTHER INFORMATION: 3?- U5-region

<400> SEQUENCE: 5

```
ctgcctcgcg cgtttcggtg atgacggtga aaacctctga cacatgcagc tcccggagac    60
ggtcacagct tgtctgtaag cggatgccgg gagcagacaa gcccgtcagg gcgcgtcagc   120
gggtgttggc gggtgtcggg gcgcagccat gacccagtca cgtagcgata gttactatgc   180
ggcatcagag cagattgtac tgagagtgca ccatatgcgg tgtgaaatac cgcacagatg   240
cgtaaggaga aaataccgca tcaggcgcca ttcgccattc aggctgcgca actgttggga   300
agggcgatcg gtgcgggcct cttcgctatt acgccagctg gcgaaagggg gatgtgctgc   360
aaggcgatta agttgggtaa cgccagggtt ttcccagtca cgacgttgta aaacgacggc   420
cagtgaatta gtactctagc ttaagacgcg tggcctgaaa taacctctga agaggaact    480 tggttaggta ccttctgagg cggaaagaac cagctgtgga atgtgtgtca gttagggtgt   540
ggaaagtccc caggctcccc agcaggcaga agtatgcaaa gcatgcatct caattagtca   600
gcaaccaggt gtggaaagtc cccaggctcc ccagcaggca gaagtatgca aagcatgcat   660
ctcaattagt cagcaaccat agtcccttaa gaatgtagtc ttatgcaata ctcttgtagt   720
cttgcaacat ggtaacgatg agttagcaac atgccttaca aggagagaaa agcaccgtg    780 catgccgatt ggtggaagta aggtggtacg atcgtgcctt attaggaagg caacagacgg   840
gtctgacatg gattggacga accactgaat tgccgcattg cagagatatt gtatttaagt   900
gcctagctcg atacaataaa cgccatttga ccattcacca cattggtgtg cacctgggtt   960
gatggccgga ccgttgattc cctgacgact acgagcacct gcatgaagca gaaggcttca  1020
tttggtgacc ccgacgtgat agttagggaa tagtggtcgg ccacagacgg cgtggcgatc  1080
ctgtctccat ccgtctcgtc tatcgggagg cgagttcgat gaccctggtg gaggggctg   1140 cggcttaggg aggcagaagc tgagtaccgt cggagggagc tccagggccc ggagcgactg  1200 accctgccg agaactcaga gggtcgtcgg aagacggaga gtgagcccga cgaccacccc  1260
aggcacgtct ttggtcggcc tgcggatcaa gcagcggccg ctagctgcag taacgccatt  1320
ttgcaaggca tggaaaaata ccaaaccaag aatagagaag ttcagatcaa gggcgggtac  1380
atgaaaatag ctaacgttgg gccaaacagg atatctgcgg tgagcagttt cggccccggc  1440
ccggggccaa gaacagatgg tcaccgcagt ttcggccccg gcccgaggcc aagaacagat  1500
ggtccccaga tatggcccaa ccctcagcag tttcttaaga cccatcagat gtttccaggc  1560
tcccccaagg acctgaaatg accctgcgcc ttatttgaat taaccaatca gcctgcttct  1620
cgcttctgtt cgcgcgcttc tgcttcccga gctctataaa agagctcaca ccccctcact  1680
cggcgcgcca gtcctccgac agactgagtc ggccggtcga atcaagctta tcgataccgt  1740
```

| | |
|---|---|
| cgacggatcc accggtcgcc acc atg gtg agc aag ggc gag gag ctg ttc acc | 1793 |
|                              Met Val Ser Lys Gly Glu Glu Leu Phe Thr | |
|                              1           5                10 | |
| ggg gtg gtg ccc atc ctg gtc gag ctg gac ggc gac gta aac ggc cac | 1841 |
| Gly Val Val Pro Ile Leu Val Glu Leu Asp Gly Asp Val Asn Gly His | |
|                15                20               25 | |
| aag ttc agc gtg tcc ggc gag ggc gag ggc gat gcc acc tac ggc aag | 1889 |
| Lys Phe Ser Val Ser Gly Glu Gly Glu Gly Asp Ala Thr Tyr Gly Lys | |
|               30                35               40 | |
| ctg acc ctg aag ttc atc tgc acc acc ggc aag ctg ccc gtg ccc tgg | 1937 |
| Leu Thr Leu Lys Phe Ile Cys Thr Thr Gly Lys Leu Pro Val Pro Trp | |
|            45                50               55 | |

```
ccc acc ctc gtg acc acc ctg acc tac ggc gtg cag tgc ttc agc cgc    1985
Pro Thr Leu Val Thr Thr Leu Thr Tyr Gly Val Gln Cys Phe Ser Arg
     60                  65                  70 tac ccc gac cac atg aag cag cac gac ttc ttc aag tcc gcc atg ccc    2033
Tyr Pro Asp His Met Lys Gln His Asp Phe Phe Lys Ser Ala Met Pro
 75                  80                  85                  90 gaa ggc tac gtc cag gag cgc acc atc ttc ttc aag gac gac ggc aac    2081
Glu Gly Tyr Val Gln Glu Arg Thr Ile Phe Phe Lys Asp Asp Gly Asn
                 95                 100                 105 tac aag acc cgc gcc gag gtg aag ttc gag ggc gac acc ctg gtg aac    2129
Tyr Lys Thr Arg Ala Glu Val Lys Phe Glu Gly Asp Thr Leu Val Asn
             110                 115                 120 cgc atc gag ctg aag ggc atc gac ttc aag gag gac ggc aac atc ctg    2177
Arg Ile Glu Leu Lys Gly Ile Asp Phe Lys Glu Asp Gly Asn Ile Leu
         125                 130                 135 ggg cac aag ctg gag tac aac tac aac agc cac aac gtc tat atc atg    2225
Gly His Lys Leu Glu Tyr Asn Tyr Asn Ser His Asn Val Tyr Ile Met
     140                 145                 150 gcc gac aag cag aag aac ggc atc aag gtg aac ttc aag atc cgc cac    2273
Ala Asp Lys Gln Lys Asn Gly Ile Lys Val Asn Phe Lys Ile Arg His
155                 160                 165                 170 aac atc gag gac ggc agc gtg cag ctc gcc gac cac tac cag cag aac    2321
Asn Ile Glu Asp Gly Ser Val Gln Leu Ala Asp His Tyr Gln Gln Asn
                175                 180                 185 acc ccc atc ggc gac ggc ccc gtg ctg ctg ccc gac aac cac tac ctg    2369
Thr Pro Ile Gly Asp Gly Pro Val Leu Leu Pro Asp Asn His Tyr Leu
            190                 195                 200 agc acc cag tcc gcc ctg agc aaa gac ccc aac gag aag cgc gat cac    2417
Ser Thr Gln Ser Ala Leu Ser Lys Asp Pro Asn Glu Lys Arg Asp His
        205                 210                 215 atg gtc ctg ctg gag ttc gtg acc gcc gcc ggg atc act ctc ggc atg    2465
Met Val Leu Leu Glu Phe Val Thr Ala Ala Gly Ile Thr Leu Gly Met
    220                 225                 230 gac gag ctg tac aag taa agcggccgcg tcgacggatc ccccgggctg           2513
Asp Glu Leu Tyr Lys
235 caggaattcg agcatcttac cgccatttat acccatattt gttctgtttt tcttgatttg  2573 ggtatacatt taaatgttaa taaaacaaaa tggtggggca atcatttaca tttttaggga  2633 tatgtaatta ctagttcagg tgtattgcca caagacaaac atgttaagaa actttcccgt  2693 tatttacgct ctgttcctgt taatcaacct ctggattaca aaatttgtga agattgact   2753 gatattctta actatgttgc tccttttacg ctgtgtggat atgctgcttt aatgcctctg  2813 tatcatgcta ttgcttcccg tacggctttc gttttctcct ccttgtataa atcctggttg  2873 ctgtctcttt atgaggagtt gtggcccgtt gtccgtcaac gtggcgtggt gtgctctgtg  2933 tttgctgacg caacccccac tggctgggc attgccacca cctgtcaact cctttctggg   2993 actttcgctt tccccctccc gatcgccacg gcagaactca tcgccgcctg ccttgcccgc  3053 tgctggacag gggctaggtt gctgggcact gataattccg tggtgttgtc ggggaagctg  3113 acgtcctttc gaattcgaaa gcttttaaat atcgatgcga tgtacgggcc agatatacgc  3173 gtatctgagg ggactagggt gtgtttaggc gaaaagcggg gcttcggttg tacgcggtta  3233 ggagtcccct taggatatag tagtttcgct tttgcatagg gagggggaaa tgtagtctta  3293 tgcaatactc ttgtacgtag agatattgta tttaagtgcc tagctcgata caataaacgc  3353 catttgacca ttcaccacat tggtgtgcac ctgggttgat ggccggaccg ttgattccct  3413 gacgactacg agcacctgca tgaagcagaa ggcttcattc tcgagagctt tggcgtaatc  3473
```

```
atggtcatag ctgtttcctg tgtgaaattg ttatccgctc acaattccac acaacatacg    3533
agccggaagc ataaagtgta aagcctgggg tgcctaatga gtgagctaac tcacattaat    3593
tgcgttgcgc tcactgcccg ctttccagtc gggaaacctg tcgtgccagc tgcattaatg    3653
aatcggccaa cgcgcgggga gaggcggttt gcgtattggg cgctcttccg cttcctcgct    3713
cactgactcg ctgcgctcgg tcgttcggct gcggcgagcg gtatcagctc actcaaaggc    3773
ggtaatacgg ttatccacag aatcagggga taacgcagga agaacatgt gagcaaaagg    3833
ccagcaaaag gccaggaacc gtaaaaaggc cgcgttgctg gcgttttttcc ataggctccg    3893
cccccctgac gagcatcaca aaaatcgacg ctcaagtcag aggtggcgaa acccgacagg    3953
actataaaga taccaggcgt ttccccctgg aagctccctc gtgcgctctc ctgttccgac    4013
cctgccgctt accggatacc tgtccgcctt tctcccttcg ggaagcgtgg cgctttctca    4073
atgctcacgc tgtaggtatc tcagttcggt gtaggtcgtt cgctccaagc tgggctgtgt    4133
gcacgaaccc cccgttcagc ccgaccgctg cgccttatcc ggtaactatc gtcttgagtc    4193
caacccggta agacacgact tatcgccact ggcagcagcc actggtaaca ggattagcag    4253
agcgaggtat gtaggcggtg ctacagagtt cttgaagtgg tggcctaact acggctacac    4313
tagaaggaca gtatttggta tctgcgctct gctgaagcca gttaccttcg gaaaaagagt    4373
tggtagctct tgatccggca aacaaaccac cgctggtagc ggtggttttt ttgtttgcaa    4433
gcagcagatt acgcgcagaa aaaaaggatc tcaagaagat cctttgatct tttctacggg    4493
gtctgacgct cagtggaacg aaaactcacg ttaagggatt ttggtcatga gattatcaaa    4553
aaggatcttc acctagatcc ttttaaatta aaaatgaagt tttaaatcaa tctaaagtat    4613
atatgagtaa acttggtctg acagttacca atgcttaatc agtgaggcac ctatctcagc    4673
gatctgtcta tttcgttcat ccatagttgc ctgactcccc gtcgtgtaga taactacgat    4733
acgggagggc ttaccatctg gccccagtgc tgcaatgata ccgcgagacc cacgctcacc    4793
ggctccagat ttatcagcaa taaaccagcc agccggaagg gccgagcgca gaagtggtcc    4853
tgcaacttta tccgcctcca tccagtctat taattgttgc cgggaagcta gagtaagtag    4913
ttcgccagtt aatagtttgc gcaacgttgt tgccattgct gctggcatcg tggtgtcacg    4973
ctcgtcgttt ggtatggctt cattcagctc cggttcccaa cgatcaaggc gagttacatg    5033
atcccccatg ttgtgcaaaa aagcggttag ctccttcggt cctccgatcg ttgtcagaag    5093
taagttggcc gcagtgttat cactcatggt tatggcagca ctgcataatt ctcttactgt    5153
catgccatcc gtaagatgct tttctgtgac tggtgagtac tcaaccaagt cattctgaga    5213
atagtgtatg cggcgaccga gttgctcttg cccggcgtca atacgggata ataccgcgcc    5273
acatagcaga actttaaaag tgctcatcat tggaaaacgt tcttcgggc gaaaactctc    5333
aaggatctta ccgctgttga tccagttc gatgtaaccc actcgtgcac ccaactgatc    5393
ttcagcatct tttactttca ccagcgtttc tgggtgagca aaaacaggaa ggcaaaatgc    5453
cgcaaaaaag ggaataaggg cgacacggaa atgttgaata ctcatactct tcctttttca    5513
atattattga agcatttatc agggttattg tctcatgagc ggatacatat ttgaatgtat    5573
ttagaaaaat aaacaaatag gggttccgcg cacatttccc cgaaaagtgc cacctgacgt    5633
ctaagaaacc attattatca tgacattaac ctataaaaat aggcgtatca cgaggccctt    5693
tcgtcttcaa g                                                        5704
```

<210> SEQ ID NO 6
<211> LENGTH: 239
<212> TYPE: PRT

-continued

```
<213> ORGANISM: Artificial Sequence
<220> FEATURE:
<223> OTHER INFORMATION: Synthetic Construct

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 7
<211> LENGTH: 5688
<212> TYPE: DNA
<213> ORGANISM: Artificial Sequence
<220> FEATURE:
<223> OTHER INFORMATION: /note="SEQ ID NO: 7: viral vector with U3-
      region deleted"
<220> FEATURE:
<221> NAME/KEY: enhancer
<222> LOCATION: (452)..(684)
<223> OTHER INFORMATION: SV40 enhancer
<220> FEATURE:
<221> NAME/KEY: promoter
<222> LOCATION: (693)..(921)
<223> OTHER INFORMATION: RSV promoter
<220> FEATURE:
<221> NAME/KEY: misc_feature
<222> LOCATION: (922)..(942)
<223> OTHER INFORMATION: 5?- R-region
<220> FEATURE:
<221> NAME/KEY: misc_feature
<222> LOCATION: (943)..(1022)
<223> OTHER INFORMATION: 5?- U5-region
<220> FEATURE:
<221> NAME/KEY: PBS
<222> LOCATION: (1023)..(1041)
<223> OTHER INFORMATION: primer bindin site
<220> FEATURE:
```

```
<221> NAME/KEY: promoter
<222> LOCATION: (1293)..(1684)
<223> OTHER INFORMATION: internal promoter of the expression cassette:
      SFFV
<220> FEATURE:
<221> NAME/KEY: CDS
<222> LOCATION: (1764)..(2483)
<223> OTHER INFORMATION: EGFP: coding sequence for eGFP
<220> FEATURE:
<221> NAME/KEY: misc_feature
<222> LOCATION: (2522)..(3124)
<223> OTHER INFORMATION: PRE of the expression cassette
<220> FEATURE:
<221> NAME/KEY: misc_feature
<222> LOCATION: (3282)..(3335)
<223> OTHER INFORMATION: 3?- U3-Region with deletion
<220> FEATURE:
<221> NAME/KEY: misc_feature
<222> LOCATION: (3336)..(3356)
<223> OTHER INFORMATION: 3?-R-region
<220> FEATURE:
<221> NAME/KEY: misc_feature
<222> LOCATION: (3357)..(3436)
<223> OTHER INFORMATION: 3?- U5-region

<400> SEQUENCE: 7
ctgcctcgcg cgtttcggtg atgacggtga aaacctctga cacatgcagc tcccggagac      60
ggtcacagct tgtctgtaag cggatgccgg gagcagacaa gcccgtcagg gcgcgtcagc     120
gggtgttggc gggtgtcggg gcgcagccat gacccagtca cgtagcgata gttactatgc     180
ggcatcagag cagattgtac tgagagtgca ccatatgcgg tgtgaaatac cgcacagatg     240
cgtaaggaga aaataccgca tcaggcgcca ttcgccattc aggctgcgca actgttggga     300
agggcgatcg gtgcgggcct cttcgctatt acgccagctg gcgaaagggg gatgtgctgc     360
aaggcgatta agttgggtaa cgccagggtt ttcccagtca cgacgttgta aaacgacggc     420
cagtgaatta gtactctagc ttaagacgcg tggcctgaaa taacctctga agaggaact     480 tggttaggta ccttctgagg cggaaagaac cagctgtgga atgtgtgtca gttagggtgt     540
ggaaagtccc caggctcccc agcaggcaga agtatgcaaa gcatgcatct caattagtca     600
gcaaccaggt gtggaaagtc cccaggctcc ccagcaggca gaagtatgca aagcatgcat     660
ctcaattagt cagcaaccat agtcccttaa gaatgtagtc ttatgcaata ctcttgtagt     720
cttgcaacat ggtaacgatg agttagcaac atgccttaca aggagagaaa aagcaccgtg     780
catgccgatt ggtggaagta aggtggtacg atcgtgcctt attaggaagg caacagacgg     840
gtctgacatg gattggacga accactgaat tgccgcattg cagagatatt gtatttaagt     900
gcctagctcg atacaataaa cgccatttga ccattcacca cattggtgtg cacctgggtt     960
gatggccgga ccgttgattc cctgacgact acgagcacct gcatgaagca gaaggcttca    1020
tttggtgacc ccgacgtgat agttagggaa tagtggtcgg ccacagacgg cgtggcgatc    1080
ctgtctccat ccgtctcgtc tatcgggagg cgagttcgat gacccctggtg gaggggctg     1140 cggcttaggg aggcagaagc tgagtaccgt cggagggagc tccagggccc ggagcgactg    1200 accccctgccg agaactcaga gggtcgtcgg aagacggaga gtgagcccga cgaccacccc    1260
aggcacgtct ttggtcggcc tgcggatcaa gcagcggccg ctagctgcag taacgccatt    1320
ttgcaaggca tggaaaaata ccaaaccaag aatagagaag ttcagatcaa gggcgggtac    1380
atgaaaatag ctaacgttgg gccaaacagg atatctgcgg tgagcagttt cggccccggc    1440
ccggggccaa gaacagatgg tcaccgcagt ttcggccccg gcccgaggcc aagaacagat    1500
ggtccccaga tatggcccaa ccctcagcag tttcttaaga cccatcagat gtttccaggc    1560
tcccccaagg acctgaaatg accctgcgcc ttatttgaat taaccaatca gcctgcttct    1620
```

```
cgcttctgtt cgcgcgcttc tgcttcccga gctctataaa agagctcaca acccctcact    1680
cggcgcgcca gtcctccgac agactgagtc ggccggtcga atcaagctta tcgataccgt    1740
cgacggatcc accggtcgcc acc atg gtg agc aag ggc gag gag ctg ttc acc    1793
                         Met Val Ser Lys Gly Glu Glu Leu Phe Thr
                           1               5                  10 ggg gtg gtg ccc atc ctg gtc gag ctg gac ggc gac gta aac ggc cac      1841
Gly Val Val Pro Ile Leu Val Glu Leu Asp Gly Asp Val Asn Gly His
                 15                  20                  25 aag ttc agc gtg tcc ggc gag ggc gag ggc gat gcc acc tac ggc aag      1889
Lys Phe Ser Val Ser Gly Glu Gly Glu Gly Asp Ala Thr Tyr Gly Lys
             30                  35                  40 ctg acc ctg aag ttc atc tgc acc acc ggc aag ctg ccc gtg ccc tgg      1937
Leu Thr Leu Lys Phe Ile Cys Thr Thr Gly Lys Leu Pro Val Pro Trp
         45                  50                  55 ccc acc ctc gtg acc acc ctg acc tac ggc gtg cag tgc ttc agc cgc      1985
Pro Thr Leu Val Thr Thr Leu Thr Tyr Gly Val Gln Cys Phe Ser Arg
     60                  65                  70 tac ccc gac cac atg aag cag cac gac ttc ttc aag tcc gcc atg ccc      2033
Tyr Pro Asp His Met Lys Gln His Asp Phe Phe Lys Ser Ala Met Pro
 75                  80                  85                  90 gaa ggc tac gtc cag gag cgc acc atc ttc ttc aag gac gac ggc aac      2081
Glu Gly Tyr Val Gln Glu Arg Thr Ile Phe Phe Lys Asp Asp Gly Asn
                 95                 100                 105 tac aag acc cgc gcc gag gtg aag ttc gag ggc gac acc ctg gtg aac      2129
Tyr Lys Thr Arg Ala Glu Val Lys Phe Glu Gly Asp Thr Leu Val Asn
            110                 115                 120 cgc atc gag ctg aag ggc atc gac ttc aag gag gac ggc aac atc ctg      2177
Arg Ile Glu Leu Lys Gly Ile Asp Phe Lys Glu Asp Gly Asn Ile Leu
        125                 130                 135 ggg cac aag ctg gag tac aac tac aac agc cac aac gtc tat atc atg      2225
Gly His Lys Leu Glu Tyr Asn Tyr Asn Ser His Asn Val Tyr Ile Met
    140                 145                 150 gcc gac aag cag aag aac ggc atc aag gtg aac ttc aag atc cgc cac      2273
Ala Asp Lys Gln Lys Asn Gly Ile Lys Val Asn Phe Lys Ile Arg His
155                 160                 165                 170 aac atc gag gac ggc agc gtg cag ctc gcc gac cac tac cag cag aac      2321
Asn Ile Glu Asp Gly Ser Val Gln Leu Ala Asp His Tyr Gln Gln Asn
                175                 180                 185 acc ccc atc ggc gac ggc ccc gtg ctg ctg ccc gac aac cac tac ctg      2369
Thr Pro Ile Gly Asp Gly Pro Val Leu Leu Pro Asp Asn His Tyr Leu
            190                 195                 200 agc acc cag tcc gcc ctg agc aaa gac ccc aac gag aag cgc gat cac      2417
Ser Thr Gln Ser Ala Leu Ser Lys Asp Pro Asn Glu Lys Arg Asp His
        205                 210                 215 atg gtc ctg ctg gag ttc gtg acc gcc gcc ggg atc act ctc ggc atg      2465
Met Val Leu Leu Glu Phe Val Thr Ala Ala Gly Ile Thr Leu Gly Met
    220                 225                 230 gac gag ctg tac aag taa agcggccgcg tcgacggatc ccccgggctg             2513
Asp Glu Leu Tyr Lys
235 caggaattcg agcatcttac cgccatttat acccatattt gttctgtttt tcttgatttg    2573 ggtatacatt taaatgttaa taaaacaaaa tggtggggca atcatttaca tttttaggga    2633 tatgtaatta ctagttcagg tgtattgcca caagacaaac atgttaagaa actttcccgt    2693 tatttacgct ctgttcctgt taatcaacct ctggattaca aaatttgtga agattgact     2753 gatattctta actatgttgc tccttttacg ctgtgtggat atgctgcttt aatgcctctg    2813 tatcatgcta ttgcttcccg tacggctttc gttttctcct ccttgtataa atcctggttg    2873
```

```
ctgtctcttt atgaggagtt gtggcccgtt gtccgtcaac gtggcgtggt gtgctctgtg    2933
tttgctgacg caaccccccac tggctggggc attgccacca cctgtcaact cctttctggg    2993
actttcgctt tccccctccc gatcgccacg gcagaactca tcgccgcctg ccttgcccgc    3053
tgctggacag gggctaggtt gctgggcact gataattccg tggtgttgtc ggggaagctg    3113
acgtcctttc gaattcgaaa gcttttaaat atcgatgcga tgtacgggcc agatatacgc    3173
gtatctgagg ggactagggt gtgtttaggc gaaaagcggg gcttcggttg tacgcggtta    3233
ggagtcccct taggatatag tagtttcgct tttgcatagg gagggggaaa tgtagtctta    3293
tgcaatactc ttgtacgtag tgcctagctc gatacaataa acgccatttg accattcacc    3353
acattggtgt gcacctgggt tgatggccgg accgttgatt ccctgacgac tacgagcacc    3413
tgcatgaagc agaaggcttc attctcgaga gctttggcgt aatcatggtc atagctgttt    3473
cctgtgtgaa attgttatcc gctcacaatt ccacacaaca tacgagccgg aagcataaag    3533
tgtaaagcct ggggtgccta atgagtgagc taactcacat taattgcgtt gcgctcactg    3593
cccgctttcc agtcgggaaa cctgtcgtgc cagctgcatt aatgaatcgg ccaacgcgcg    3653
gggagaggcg gtttgcgtat tgggcgctct tccgcttcct cgctcactga ctcgctgcgc    3713
tcggtcgttc ggctgcggcg agcggtatca gctcactcaa aggcggtaat acggttatcc    3773
acagaatcag gggataacgc aggaaagaac atgtgagcaa aaggccagca aaaggccagg    3833
aaccgtaaaa aggccgcgtt gctggcgttt ttccataggc tccgcccccc tgacgagcat    3893
cacaaaaatc gacgctcaag tcagaggtgg cgaaacccga caggactata aagataccag    3953
gcgtttcccc ctggaagctc cctcgtgcgc tctcctgttc cgaccctgcc gcttaccgga    4013
tacctgtccg cctttctccc ttcgggaagc gtggcgcttt ctcaatgctc acgctgtagg    4073
tatctcagtt cggtgtaggt cgttcgctcc aagctgggct gtgtgcacga accccccgtt    4133
cagcccgacc gctgcgcctt atccggtaac tatcgtcttg agtccaaccc ggtaagacac    4193
gacttatcgc cactggcagc agccactggt aacaggatta gcagagcgag gtatgtaggc    4253
ggtgctacag agttcttgaa gtggtggcct aactacggct acactagaag gacagtattt    4313
ggtatctgcg ctctgctgaa gccagttacc ttcggaaaaa gagttggtag ctcttgatcc    4373
ggcaaacaaa ccaccgctgg tagcggtggt ttttttgttt gcaagcagca gattacgcgc    4433
agaaaaaaag gatctcaaga agatcctttg atcttttcta cggggtctga cgctcagtgg    4493
aacgaaaact cacgttaagg gattttggtc atgagattat caaaaaggat cttcacctag    4553
atccttttaa attaaaaatg aagttttaaa tcaatctaaa gtatatatga gtaaacttgg    4613
tctgacagtt accaatgctt aatcagtgag gcacctatct cagcgatctg tctatttcgt    4673
tcatccatag ttgcctgact ccccgtcgtg tagataacta cgatacggga gggcttacca    4733
tctggcccca gtgctgcaat gataccgcga gacccacgct caccggctcc agatttatca    4793
gcaataaacc agccagccgg aagggccgag cgcagaagtg gtcctgcaac tttatccgcc    4853
tccatccagt ctattaattg ttgccgggaa gctagagtaa gtagttcgcc agttaatagt    4913
ttgcgcaacg ttgttgccat tgctgctggc atcgtggtgt cacgctcgtc gtttggtatg    4973
gcttcattca gctccggttc ccaacgatca aggcgagtta catgatcccc catgttgtgc    5033
aaaaaagcgg ttagctcctt cggtcctccg atcgttgtca gaagtaagtt ggccgcagtg    5093
ttatcactca tggttatggc agcactgcat aattctctta ctgtcatgcc atccgtaaga    5153
tgcttttctg tgactggtga gtactcaacc aagtcattct gagaatagtg tatgcggcga    5213
ccgagttgct cttgcccggc gtcaatacgg gataataccg cgccacatag cagaacttta    5273
```

```
aaagtgctca tcattggaaa acgttcttcg gggcgaaaac tctcaaggat cttaccgctg    5333
ttgagatcca gttcgatgta acccactcgt gcacccaact gatcttcagc atcttttact    5393
ttcaccagcg tttctgggtg agcaaaaaca ggaaggcaaa atgccgcaaa aaagggaata    5453
agggcgacac ggaaatgttg aatactcata ctcttccttt ttcaatatta ttgaagcatt    5513
tatcagggtt attgtctcat gagcggatac atatttgaat gtatttagaa aaataaacaa    5573
ataggggttc cgcgcacatt tccccgaaaa gtgccacctg acgtctaaga aaccattatt    5633
atcatgacat taacctataa aaataggcgt atcacgaggc cctttcgtct tcaag         5688
```

<210> SEQ ID NO 8
<211> LENGTH: 239
<212> TYPE: PRT
<213> ORGANISM: Artificial Sequence
<220> FEATURE:
<223> OTHER INFORMATION: Synthetic Construct

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 9
<211> LENGTH: 5704
<212> TYPE: DNA
<213> ORGANISM: Artificial Sequence
<220> FEATURE:
<223> OTHER INFORMATION: /note="SEQ ID NO: 9: viral vector with deletion
      and mutated TATA-box in 3?-U3-region"
<220> FEATURE:
<221> NAME/KEY: enhancer

```
<222> LOCATION: (452)..(684)
<223> OTHER INFORMATION: SV40 enhancer
<220> FEATURE:
<221> NAME/KEY: promoter
<222> LOCATION: (693)..(921)
<223> OTHER INFORMATION: RSV promoter
<220> FEATURE:
<221> NAME/KEY: misc_feature
<222> LOCATION: (922)..(942)
<223> OTHER INFORMATION: 5?- R-region
<220> FEATURE:
<221> NAME/KEY: misc_feature
<222> LOCATION: (943)..(1022)
<223> OTHER INFORMATION: 5?- U5-region
<220> FEATURE:
<221> NAME/KEY: PBS
<222> LOCATION: (1023)..(1041)
<220> FEATURE:
<221> NAME/KEY: promoter
<222> LOCATION: (1293)..(1684)
<223> OTHER INFORMATION: SFFV promotor
<220> FEATURE:
<221> NAME/KEY: CDS
<222> LOCATION: (1764)..(2483)
<223> OTHER INFORMATION: EGFP: coding sequence for eGFP
<220> FEATURE:
<221> NAME/KEY: misc_signal
<222> LOCATION: (2522)..(3124)
<223> OTHER INFORMATION: PRE
<220> FEATURE:
<221> NAME/KEY: misc_feature
<222> LOCATION: (3282)..(3351)
<223> OTHER INFORMATION: deleted 3?- U3
<220> FEATURE:
<221> NAME/KEY: misc_feature
<222> LOCATION: (3322)..(3328)
<223> OTHER INFORMATION: mutated TATA box in deleted 3?- U3
<220> FEATURE:
<221> NAME/KEY: misc_feature
<222> LOCATION: (3352)..(3372)
<223> OTHER INFORMATION: 3?- R-region
<220> FEATURE:
<221> NAME/KEY: misc_feature
<222> LOCATION: (3373)..(3452)
<223> OTHER INFORMATION: 3?-U5-region

<400> SEQUENCE: 9
ctgcctcgcg cgtttcggtg atgacggtga aaacctctga cacatgcagc tcccggagac      60
ggtcacagct tgtctgtaag cggatgccgg gagcagacaa gcccgtcagg gcgcgtcagc     120
gggtgttggc gggtgtcggg gcgcagccat gacccagtca cgtagcgata gttactatgc     180
ggcatcagag cagattgtac tgagagtgca ccatatgcgg tgtgaaatac cgcacagatg     240
cgtaaggaga aaataccgca tcaggcgcca ttcgccattc aggctgcgca actgttggga     300
agggcgatcg gtgcgggcct cttcgctatt acgccagctg gcgaaagggg gatgtgctgc     360
aaggcgatta agttgggtaa cgccagggtt ttcccagtca cgacgttgta aaacgacggc     420
cagtgaatta gtactctagc ttaagacgcg tggcctgaaa taacctctga agaggaact      480 tggttaggta ccttctgagg cggaaagaac cagctgtgga atgtgtgtca gttagggtgt     540
ggaaagtccc caggctcccc agcaggcaga agtatgcaaa gcatgcatct caattagtca     600
gcaaccaggt gtggaaagtc cccaggctcc ccagcaggca gaagtatgca aagcatgcat     660
ctcaattagt cagcaaccat agtcccttaa gaatgtagtc ttatgcaata ctcttgtagt     720
cttgcaacat ggtaacgatg agttagcaac atgccttaca aggagagaaa aagcaccgtg     780
catgccgatt ggtggaagta aggtggtacg atcgtgcctt attaggaagg caacagacgg     840
gtctgacatg gattggacga accactgaat tgccgcattg cagagatatt gtatttaagt     900
gcctagctcg atacaataaa cgccatttga ccattcacca cattggtgtg cacctgggtt     960
```

-continued

```
gatggccgga ccgttgattc cctgacgact acgagcacct gcatgaagca gaaggcttca   1020
tttggtgacc ccgacgtgat agttaggaa tagtggtcgg ccacagacgg cgtggcgatc    1080
ctgtctccat ccgtctcgtc tatcgggagg cgagttcgat gaccctggtg gagggggctg   1140
cggcttaggg aggcagaagc tgagtaccgt cggagggagc tccagggccc ggagcgactg   1200
accccctgccg agaactcaga gggtcgtcgg aagacggaga gtgagcccga cgaccacccc  1260
aggcacgtct ttggtcggcc tgcggatcaa gcagcggccg ctagctgcag taacgccatt   1320
ttgcaaggca tggaaaaata ccaaaccaag aatagagaag ttcagatcaa gggcgggtac   1380
atgaaaatag ctaacgttgg gccaaacagg atatctgcgg tgagcagttt cggcccggc    1440
ccggggccaa gaacagatgg tcaccgcagt ttcggccccg gcccgaggcc aagaacagat   1500
ggtccccaga tatggcccaa ccctcagcag tttcttaaga cccatcagat gtttccaggc   1560
tcccccaagg acctgaaatg accctgcgcc ttatttgaat taaccaatca gcctgcttct   1620
cgcttctgtt cgcgcgcttc tgcttcccga gctctataaa agagctcaca cccctcact   1680
cggcgcgcca gtcctccgac agactgagtc ggccggtcga atcaagctta tcgataccgt   1740
cgacggatcc accggtcgcc acc atg gtg agc aag ggc gag gag ctg ttc acc   1793
                            Met Val Ser Lys Gly Glu Glu Leu Phe Thr
                             1               5                  10 ggg gtg gtg ccc atc ctg gtc gag ctg gac ggc gac gta aac ggc cac     1841
Gly Val Val Pro Ile Leu Val Glu Leu Asp Gly Asp Val Asn Gly His
                15                  20                  25 aag ttc agc gtg tcc ggc gag ggc gag ggc gat gcc acc tac ggc aag     1889
Lys Phe Ser Val Ser Gly Glu Gly Glu Gly Asp Ala Thr Tyr Gly Lys
            30                  35                  40 ctg acc ctg aag ttc atc tgc acc acc ggc aag ctg ccc gtg ccc tgg     1937
Leu Thr Leu Lys Phe Ile Cys Thr Thr Gly Lys Leu Pro Val Pro Trp
        45                  50                  55 ccc acc ctc gtg acc acc ctg acc tac ggc gtg cag tgc ttc agc cgc     1985
Pro Thr Leu Val Thr Thr Leu Thr Tyr Gly Val Gln Cys Phe Ser Arg
    60                  65                  70 tac ccc gac cac atg aag cag cac gac ttc ttc aag tcc gcc atg ccc     2033
Tyr Pro Asp His Met Lys Gln His Asp Phe Phe Lys Ser Ala Met Pro
75                  80                  85                  90 gaa ggc tac gtc cag gag cgc acc atc ttc ttc aag gac gac ggc aac     2081
Glu Gly Tyr Val Gln Glu Arg Thr Ile Phe Phe Lys Asp Asp Gly Asn
                95                  100                 105 tac aag acc cgc gcc gag gtg aag ttc gag ggc gac acc ctg gtg aac     2129
Tyr Lys Thr Arg Ala Glu Val Lys Phe Glu Gly Asp Thr Leu Val Asn
            110                 115                 120 cgc atc gag ctg aag ggc atc gac ttc aag gag gac ggc aac atc ctg     2177
Arg Ile Glu Leu Lys Gly Ile Asp Phe Lys Glu Asp Gly Asn Ile Leu
        125                 130                 135 ggg cac aag ctg gag tac aac tac aac agc cac aac gtc tat atc atg     2225
Gly His Lys Leu Glu Tyr Asn Tyr Asn Ser His Asn Val Tyr Ile Met
    140                 145                 150 gcc gac aag cag aag aac ggc atc aag gtg aac ttc aag atc cgc cac     2273
Ala Asp Lys Gln Lys Asn Gly Ile Lys Val Asn Phe Lys Ile Arg His
155                 160                 165                 170 aac atc gag gac ggc agc gtg cag ctc gcc gac cac tac cag cag aac     2321
Asn Ile Glu Asp Gly Ser Val Gln Leu Ala Asp His Tyr Gln Gln Asn
                175                 180                 185 acc ccc atc ggc gac ggc ccc gtg ctg ctg ccc gac aac cac tac ctg     2369
Thr Pro Ile Gly Asp Gly Pro Val Leu Leu Pro Asp Asn His Tyr Leu
            190                 195                 200 agc acc cag tcc gcc ctg agc aaa gac ccc aac gag aag cgc gat cac     2417
Ser Thr Gln Ser Ala Leu Ser Lys Asp Pro Asn Glu Lys Arg Asp His
```

```
              205                 210                 215
atg gtc ctg ctg gag ttc gtg acc gcc gcc ggg atc act ctc ggc atg    2465
Met Val Leu Leu Glu Phe Val Thr Ala Ala Gly Ile Thr Leu Gly Met
    220                 225                 230 gac gag ctg tac aag taa agcggccgcg tcgacggatc ccccgggctg           2513
Asp Glu Leu Tyr Lys
235 caggaattcg agcatcttac cgccatttat acccatattt gttctgtttt tcttgatttg  2573
ggtatacatt taaatgttaa taaaacaaaa tggtggggca atcatttaca ttttaggga   2633
tatgtaatta ctagttcagg tgtattgcca caagacaaac atgttaagaa actttcccgt  2693
tatttacgct ctgttcctgt taatcaacct ctggattaca aaatttgtga agattgact   2753
gatattctta actatgttgc tccttttacg ctgtgtggat atgctgcttt aatgcctctg  2813
tatcatgcta ttgcttcccg tacggctttc gttttctcct ccttgtataa atcctggttg  2873
ctgtctcttt atgaggagtt gtgggcccgtt gtccgtcaac gtggcgtggt gtgctctgtg 2933
tttgctgacg caaccccccac tggctggggc attgccacca cctgtcaact cctttctggg 2993
actttcgctt tccccctccc gatcgccacg gcagaactca tcgccgcctg ccttgcccgc  3053
tgctggacag gggctaggtt gctgggcact gataattccg tggtgttgtc ggggaagctg  3113
acgtccttc gaattcgaaa gcttttaaat atcgatgcga tgtacgggcc agatatacgc   3173
gtatctgagg ggactagggt gtgtttaggc gaaaagcggg gcttcggttg tacgcggtta  3233
ggagtccct taggatatag tagtttcgct tttgcatagg gagggggaaa tgtagtctta   3293
tgcaatactc ttgtacgtag agatattgtg tctaagtgcc tagctcgata caataaacgc  3353
catttgacca ttcaccacat tggtgtgcac ctgggttgat ggccggaccg ttgattccct  3413
gacgactacg agcacctgca tgaagcagaa ggcttcattc tcgagagctt tggcgtaatc  3473
atggtcatag ctgttttcctg tgtgaaattg ttatccgctc acaattccac acaacatacg  3533
agccggaagc ataaagtgta aagcctgggg tgcctaatga gtgagctaac tcacattaat  3593
tgcgttgcgc tcactgcccg cttccagtc gggaaacctg tcgtgccagc tgcattaatg   3653
aatcggccaa cgcgcgggga gaggcggttt gcgtattggg cgctcttccg cttcctcgct  3713
cactgactcg ctgcgctcgg tcgttcggct gcggcgagcg tatcagctc actcaaaggc   3773
ggtaatacgg ttatccacag aatcagggga taacgcagga agaacatgt gagcaaaagg   3833
ccagcaaaag gccaggaacc gtaaaaaggc cgcgttgctg gcgttttttcc ataggctccg  3893
cccccctgac gagcatcaca aaaatcgacg ctcaagtcag aggtggcgaa acccgacagg  3953
actataaaga taccaggcgt ttccccctgg aagctccctc gtgcgctctc ctgttccgac  4013
cctgccgctt accggatacc tgtccgcctt tctcccttcg ggaagcgtgg cgctttctca  4073
atgctcacgc tgtaggtatc tcagttcggt gtaggtcgtt cgctccaagc tgggctgtgt  4133
gcacgaaccc cccgttcagc ccgaccgctg cgccttatcc ggtaactatc gtcttgagtc  4193
caacccggta agacacgact tatcgccact ggcagcagcc actggtaaca ggattagcag  4253
agcgaggtat gtaggcggtg ctacagagtt cttgaagtgg tggcctaact acggctacac  4313
tagaaggaca gtatttggta tctgcgctct gctgaagcca gttaccttcg gaaaaagagt  4373
tggtagctct tgatccggca aacaaaccac cgctggtagc ggtggttttt tgtttgcaa   4433
gcagcagatt acgcgcagaa aaaaaggatc tcaagaagat cctttgatct tttctacggg  4493
gtctgacgct cagtggaacg aaaactcacg ttaagggatt ttggtcatga gattatcaaa  4553
aaggatcttc acctagatcc ttttaaatta aaaatgaagt tttaaatcaa tctaaagtat  4613
```

-continued

```
atatgagtaa acttggtctg acagttacca atgcttaatc agtgaggcac ctatctcagc    4673
gatctgtcta tttcgttcat ccatagttgc ctgactcccc gtcgtgtaga taactacgat    4733
acgggagggc ttaccatctg gccccagtgc tgcaatgata ccgcgagacc cacgctcacc    4793
ggctccagat ttatcagcaa taaaccagcc agcggaagg gccgagcgca gaagtggtcc     4853
tgcaacttta ccgcctcca tccagtctat taattgttgc cgggaagcta gagtaagtag     4913
ttcgccagtt aatagtttgc gcaacgttgt tgccattgct gctggcatcg tggtgtcacg    4973
ctcgtcgttt ggtatggctt cattcagctc cggttcccaa cgatcaaggc gagttacatg    5033
atcccccatg ttgtgcaaaa aagcggttag ctccttcggt cctccgatcg ttgtcagaag    5093
taagttggcc gcagtgttat cactcatggt tatggcagca ctgcataatt ctcttactgt    5153
catgccatcc gtaagatgct tttctgtgac tggtgagtac tcaaccaagt cattctgaga    5213
atagtgtatg cggcgaccga gttgctcttg cccggcgtca atacgggata taccgcgcc    5273
acatagcaga actttaaaag tgctcatcat tggaaaacgt tcttcgggc gaaaactctc     5333
aaggatctta ccgctgttga gatccagttc gatgtaaccc actcgtgcac ccaactgatc    5393
ttcagcatct tttactttca ccagcgtttc tgggtgagca aaaacaggaa ggcaaaatgc    5453
cgcaaaaaag ggaataaggg cgacacggaa atgttgaata ctcatactct ccttttttca    5513
atattattga agcatttatc agggttattg tctcatgagc ggatacatat ttgaatgtat    5573
ttagaaaaat aaacaaatag gggttccgcg cacatttccc cgaaaagtgc cacctgacgt    5633
ctaagaaacc attattatca tgacattaac ctataaaaat aggcgtatca cgaggccctt    5693
tcgtcttcaa g                                                         5704
```

<210> SEQ ID NO 10
<211> LENGTH: 239
<212> TYPE: PRT
<213> ORGANISM: Artificial Sequence
<220> FEATURE:
<223> OTHER INFORMATION: Synthetic Construct

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
<211> LENGTH: 10768
<212> TYPE: DNA
<213> ORGANISM: Artificial Sequence
<220> FEATURE:
<223> OTHER INFORMATION: /note="SEQ ID NO: 11: 1. helper plasmid gag-pol
      (wild-type)"
<220> FEATURE:
<221> NAME/KEY: promoter
<222> LOCATION: (232)..(819)
<223> OTHER INFORMATION: CMV promoter
<220> FEATURE:
<221> NAME/KEY: Intron
<222> LOCATION: (907)..(1463)
<223> OTHER INFORMATION: beta-globin intron
<220> FEATURE:
<221> NAME/KEY: CDS
<222> LOCATION: (1475)..(3586)
<223> OTHER INFORMATION: gag: coding sequence for Gag, wild-type
<220> FEATURE:
<221> NAME/KEY: CDS
<222> LOCATION: (3604)..(6291)
<223> OTHER INFORMATION: pol: coding sequence for Pol, wild-type
<220> FEATURE:
<221> NAME/KEY: polyA_signal
<222> LOCATION: (6368)..(6588)
<223> OTHER INFORMATION: poly-adenylation element of bGH

<400> SEQUENCE: 11
gacggatcgg gagatctccc gatcccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag cttgaccga caattgcatg aagaatctgc       180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gcttggtacc     900
gagctcggat cctgagaact tcagggtgag tctatggac ccttgatgtt tctttcccc      960 ttcttttcta tggttaagtt catgtcatag gaagggaga agtaacaggg tacacatatt     1020
gaccaaatca gggtaattt gcatttgtaa ttttaaaaaa tgctttcttc ttttaatata     1080

-continued

```
cttttttgtt tatcttattt ctaatacttt ccctaatctc tttctttcag ggcaataatg      1140
atacaatgta tcatgcctct ttgcaccatt ctaaagaata acagtgataa tttctgggtt      1200
aaggcaatag caatatttct gcatataaat atttctgcat ataaattgta actgatgtaa      1260
gaggtttcat attgctaata gcagctacaa tccagctacc attctgcttt tattttatgg      1320
ttgggataag gctggattat tctgagtcca agctaggccc ttttgctaat catgttcata      1380
cctcttatct tcctcccaca gctcctgggc aacgtgctgg tctgtgtgct ggcccatcac      1440
tttggcaaag cacgtgagat ctgaattcgc cacc atg gaa gcc gtc att aag gtg      1495
                                    Met Glu Ala Val Ile Lys Val
                                    1               5
```

| | | | | | | | | | | | | | | | | |
|---|---|---|---|---|---|---|---|---|---|---|---|---|---|---|---|---|
| att | tcg | tcc | gcg | tgt | aaa | acc | tat | tgc | ggg | aaa | atc | tct | cct | tct | aag | 1543 |
| Ile | Ser | Ser | Ala | Cys | Lys | Thr | Tyr | Cys | Gly | Lys | Ile | Ser | Pro | Ser | Lys | |
| | 10 | | | | 15 | | | | | 20 | | | | | | |

| | | | | | | | | | | | | | | | | |
|---|---|---|---|---|---|---|---|---|---|---|---|---|---|---|---|---|
| aag | gaa | ata | ggg | gcc | atg | ttg | tcc | ctg | tta | caa | aag | gaa | ggg | ttg | ctt | 1591 |
| Lys | Glu | Ile | Gly | Ala | Met | Leu | Ser | Leu | Leu | Gln | Lys | Glu | Gly | Leu | Leu | |
| 25 | | | | | 30 | | | | | 35 | | | | | | |

| | | | | | | | | | | | | | | | | |
|---|---|---|---|---|---|---|---|---|---|---|---|---|---|---|---|---|
| atg | tct | ccc | tca | gat | tta | tat | tct | ccg | ggg | tcc | tgg | gat | ccc | atc | act | 1639 |
| Met | Ser | Pro | Ser | Asp | Leu | Tyr | Ser | Pro | Gly | Ser | Trp | Asp | Pro | Ile | Thr | |
| 40 | | | | 45 | | | | | 50 | | | | | 55 | | |

| | | | | | | | | | | | | | | | | |
|---|---|---|---|---|---|---|---|---|---|---|---|---|---|---|---|---|
| gcg | gcg | ctc | tcc | cag | cgg | gca | atg | gta | ctt | gga | aaa | tcg | gga | gag | tta | 1687 |
| Ala | Ala | Leu | Ser | Gln | Arg | Ala | Met | Val | Leu | Gly | Lys | Ser | Gly | Glu | Leu | |
| | | | 60 | | | | | 65 | | | | | 70 | | | |

| | | | | | | | | | | | | | | | | |
|---|---|---|---|---|---|---|---|---|---|---|---|---|---|---|---|---|
| aaa | acc | tgg | gga | ttg | gtt | ttg | ggg | gca | ttg | aag | gcg | gct | cga | gag | gaa | 1735 |
| Lys | Thr | Trp | Gly | Leu | Val | Leu | Gly | Ala | Leu | Lys | Ala | Ala | Arg | Glu | Glu | |
| | | 75 | | | | | 80 | | | | | 85 | | | | |

| | | | | | | | | | | | | | | | | |
|---|---|---|---|---|---|---|---|---|---|---|---|---|---|---|---|---|
| cag | gtt | aca | tct | gag | caa | gca | aag | ttt | tgg | tta | gga | tta | ggg | gga | ggg | 1783 |
| Gln | Val | Thr | Ser | Glu | Gln | Ala | Lys | Phe | Trp | Leu | Gly | Leu | Gly | Gly | Gly | |
| | | | 90 | | | | | 95 | | | | | 100 | | | |

| | | | | | | | | | | | | | | | | |
|---|---|---|---|---|---|---|---|---|---|---|---|---|---|---|---|---|
| agg | gtc | tct | ccc | cca | ggt | ccg | gag | tgc | atc | gag | aaa | cca | gct | acg | gag | 1831 |
| Arg | Val | Ser | Pro | Pro | Gly | Pro | Glu | Cys | Ile | Glu | Lys | Pro | Ala | Thr | Glu | |
| | 105 | | | | | 110 | | | | | 115 | | | | | |

| | | | | | | | | | | | | | | | | |
|---|---|---|---|---|---|---|---|---|---|---|---|---|---|---|---|---|
| cgg | cga | atc | gac | aaa | ggg | gag | gag | gtg | gga | gaa | aca | act | gtg | cag | cga | 1879 |
| Arg | Arg | Ile | Asp | Lys | Gly | Glu | Glu | Val | Gly | Glu | Thr | Thr | Val | Gln | Arg | |
| 120 | | | | | 125 | | | | | 130 | | | | | 135 | |

| | | | | | | | | | | | | | | | | |
|---|---|---|---|---|---|---|---|---|---|---|---|---|---|---|---|---|
| gat | gcg | aag | atg | gcg | cca | gag | gaa | gcg | gcc | aca | cct | aaa | acc | gtt | ggc | 1927 |
| Asp | Ala | Lys | Met | Ala | Pro | Glu | Glu | Ala | Ala | Thr | Pro | Lys | Thr | Val | Gly | |
| | | | | 140 | | | | | 145 | | | | | 150 | | |

| | | | | | | | | | | | | | | | | |
|---|---|---|---|---|---|---|---|---|---|---|---|---|---|---|---|---|
| aca | tcc | tgc | tat | cat | tgc | gga | aca | gct | gtt | ggc | tgc | aat | tgc | gcc | acc | 1975 |
| Thr | Ser | Cys | Tyr | His | Cys | Gly | Thr | Ala | Val | Gly | Cys | Asn | Cys | Ala | Thr | |
| | | | | 155 | | | | | 160 | | | | | 165 | | |

| | | | | | | | | | | | | | | | | |
|---|---|---|---|---|---|---|---|---|---|---|---|---|---|---|---|---|
| gcc | aca | gcc | tcg | gcc | cct | cct | ccc | cct | tat | gtg | ggg | agt | ggt | ttg | tat | 2023 |
| Ala | Thr | Ala | Ser | Ala | Pro | Pro | Pro | Pro | Tyr | Val | Gly | Ser | Gly | Leu | Tyr | |
| | | | 170 | | | | | 175 | | | | | 180 | | | |

| | | | | | | | | | | | | | | | | |
|---|---|---|---|---|---|---|---|---|---|---|---|---|---|---|---|---|
| cct | tcc | ctg | gcg | ggg | gtg | gga | gag | cag | cag | ggc | cag | gga | gat | aac | acg | 2071 |
| Pro | Ser | Leu | Ala | Gly | Val | Gly | Glu | Gln | Gln | Gly | Gln | Gly | Asp | Asn | Thr | |
| | | 185 | | | | | 190 | | | | | 195 | | | | |

| | | | | | | | | | | | | | | | | |
|---|---|---|---|---|---|---|---|---|---|---|---|---|---|---|---|---|
| tct | cgg | ggg | gcg | gag | cag | cca | agg | gag | gag | cca | ggg | cac | gcg | ggt | cag | 2119 |
| Ser | Arg | Gly | Ala | Glu | Gln | Pro | Arg | Glu | Glu | Pro | Gly | His | Ala | Gly | Gln | |
| 200 | | | | | 205 | | | | | 210 | | | | | 215 | |

| | | | | | | | | | | | | | | | | |
|---|---|---|---|---|---|---|---|---|---|---|---|---|---|---|---|---|
| gcc | cct | ggg | ccg | gcc | ctg | act | gac | tgg | gca | agg | gta | agg | gag | gag | ctt | 2167 |
| Ala | Pro | Gly | Pro | Ala | Leu | Thr | Asp | Trp | Ala | Arg | Val | Arg | Glu | Glu | Leu | |
| | | | | 220 | | | | | 225 | | | | | 230 | | |

| | | | | | | | | | | | | | | | | |
|---|---|---|---|---|---|---|---|---|---|---|---|---|---|---|---|---|
| gcg | agt | act | ggt | ccg | ccc | gtg | gtg | gcc | atg | cct | gta | gtg | att | aag | aca | 2215 |
| Ala | Ser | Thr | Gly | Pro | Pro | Val | Val | Ala | Met | Pro | Val | Val | Ile | Lys | Thr | |
| | | | 235 | | | | | 240 | | | | | 245 | | | |

| | | | | | | | | | | | | | | | | |
|---|---|---|---|---|---|---|---|---|---|---|---|---|---|---|---|---|
| gag | gga | ccc | gcc | tgg | acc | cct | ctg | gag | cca | aaa | ttg | atc | aca | aga | ctg | 2263 |
| Glu | Gly | Pro | Ala | Trp | Thr | Pro | Leu | Glu | Pro | Lys | Leu | Ile | Thr | Arg | Leu | |
| | | 250 | | | | | 255 | | | | | 260 | | | | |

```
gct gat acg gtc agg acc aag ggc tta cga tcc ccg atc act atg gca       2311
Ala Asp Thr Val Arg Thr Lys Gly Leu Arg Ser Pro Ile Thr Met Ala
    265                 270                 275 gaa gtg gaa gcg ctc atg tcc tcc ccg ttg ctg cca cat gac gtc acg       2359
Glu Val Glu Ala Leu Met Ser Ser Pro Leu Leu Pro His Asp Val Thr
280                 285                 290                 295 aat cta atg aga gtg att tta gga cct gcc cca tat gcc tta tgg atg       2407
Asn Leu Met Arg Val Ile Leu Gly Pro Ala Pro Tyr Ala Leu Trp Met
                300                 305                 310 gac gct tgg gga gtc caa ctc cag acg gtt ata gcg gca gcc act cgc       2455
Asp Ala Trp Gly Val Gln Leu Gln Thr Val Ile Ala Ala Ala Thr Arg
            315                 320                 325 gac ccc cga cac cca gcg aac ggt caa ggg cgg ggg gaa cgg act aac       2503
Asp Pro Arg His Pro Ala Asn Gly Gln Gly Arg Gly Glu Arg Thr Asn
        330                 335                 340 ttg gat cga tta aag ggc tta gct gat ggg atg gtg ggc aac cca cag       2551
Leu Asp Arg Leu Lys Gly Leu Ala Asp Gly Met Val Gly Asn Pro Gln
    345                 350                 355 ggt cag gcc gca tta tta aga ccg ggg gaa ttg gtt gct att acg gcg       2599
Gly Gln Ala Ala Leu Leu Arg Pro Gly Glu Leu Val Ala Ile Thr Ala
360                 365                 370                 375 tcg gct ctc cag gcg ttt aga gaa gtt gcc cgg ctg gcg gaa cct gca       2647
Ser Ala Leu Gln Ala Phe Arg Glu Val Ala Arg Leu Ala Glu Pro Ala
                380                 385                 390 ggt cca tgg gcg gac atc acg cag gga cca tct gag tcc ttt gtt gat       2695
Gly Pro Trp Ala Asp Ile Thr Gln Gly Pro Ser Glu Ser Phe Val Asp
            395                 400                 405 ttt gcc aat cgg ctt ata aag gcg gtt gag ggg tca gat ctc ccg cct       2743
Phe Ala Asn Arg Leu Ile Lys Ala Val Glu Gly Ser Asp Leu Pro Pro
        410                 415                 420 tcc gcg cgg gct ccg gtg atc att gac tgc ttt agg cag aag tca cag       2791
Ser Ala Arg Ala Pro Val Ile Ile Asp Cys Phe Arg Gln Lys Ser Gln
    425                 430                 435 cca gat att cag cag ctt ata cgg gca gca ccc tcc acg ctg acc acc       2839
Pro Asp Ile Gln Gln Leu Ile Arg Ala Ala Pro Ser Thr Leu Thr Thr
440                 445                 450                 455 cca gga gag ata atc aaa tat gtg cta gac agg cag aag att gcc cct       2887
Pro Gly Glu Ile Ile Lys Tyr Val Leu Asp Arg Gln Lys Ile Ala Pro
                460                 465                 470 ctt acg gat caa ggc ata gcc gcg gcc atg tcg tct gct atc cag ccc       2935
Leu Thr Asp Gln Gly Ile Ala Ala Ala Met Ser Ser Ala Ile Gln Pro
            475                 480                 485 tta gtt atg gca gta gtc aat aga gag agg gat gga caa act ggg tcg       2983
Leu Val Met Ala Val Val Asn Arg Glu Arg Asp Gly Gln Thr Gly Ser
        490                 495                 500 ggt ggt cgt gcc cga ggg ctc tgc tac act tgt gga tcc ccg gga cat       3031
Gly Gly Arg Ala Arg Gly Leu Cys Tyr Thr Cys Gly Ser Pro Gly His
    505                 510                 515 tat cag gca cag tgc ccg aaa aaa cga aag tca gga aac agc cgt gag       3079
Tyr Gln Ala Gln Cys Pro Lys Lys Arg Lys Ser Gly Asn Ser Arg Glu
520                 525                 530                 535 cga tgt cag ctg tgt gac ggg atg gga cac aac gct aaa cag tgt agg       3127
Arg Cys Gln Leu Cys Asp Gly Met Gly His Asn Ala Lys Gln Cys Arg
                540                 545                 550 aag cgg gat ggc aac cag ggc caa cgc cca gga aga ggt ctc tct tcg       3175
Lys Arg Asp Gly Asn Gln Gly Gln Arg Pro Gly Arg Gly Leu Ser Ser
            555                 560                 565 ggg ccg tgg ccc ggc cct gag cag cct gcc gtc tcg tta gcg atg aca       3223
Gly Pro Trp Pro Gly Pro Glu Gln Pro Ala Val Ser Leu Ala Met Thr
        570                 575                 580
```

```
atg gaa cat aaa gat cgc ccc ttg gtt agg gtc att ctg act aac act    3271
Met Glu His Lys Asp Arg Pro Leu Val Arg Val Ile Leu Thr Asn Thr
585                 590                 595 ggg agt cat cca gtc aaa caa cgt tcg gtg tat atc acc gcg ctg ttg    3319
Gly Ser His Pro Val Lys Gln Arg Ser Val Tyr Ile Thr Ala Leu Leu
600                 605                 610                 615 gac tcc gga gcg gac atc act att att tcg gag gag gat tgg cct act    3367
Asp Ser Gly Ala Asp Ile Thr Ile Ile Ser Glu Glu Asp Trp Pro Thr
                620                 625                 630 gat tgg ccg gtg gtg gac acc gcg aac cca cag atc cat ggc ata gga    3415
Asp Trp Pro Val Val Asp Thr Ala Asn Pro Gln Ile His Gly Ile Gly
            635                 640                 645 ggg gga att ccc atg cga aaa tcc cgg gat atg ata gag gtg ggg gtt    3463
Gly Gly Ile Pro Met Arg Lys Ser Arg Asp Met Ile Glu Val Gly Val
        650                 655                 660 att aac cga gac ggg tcg ttg gag cga ccc ctg ctc ctc ttc ccc gca    3511
Ile Asn Arg Asp Gly Ser Leu Glu Arg Pro Leu Leu Leu Phe Pro Ala
665                 670                 675 gtc gct atg gtt aga ggg agt atc cta gga aga gat tgt ctg cag ggc    3559
Val Ala Met Val Arg Gly Ser Ile Leu Gly Arg Asp Cys Leu Gln Gly
680                 685                 690                 695 cta ggg ctc cgc ttg aca aat tta tag ggagggccac tgttctt act gtt    3609
Leu Gly Leu Arg Leu Thr Asn Leu                        Thr Val
                700                                        705 gcg cta cat ctg gct att ccg ctc aaa tgg aag tca gac cgc acg cct    3657
Ala Leu His Leu Ala Ile Pro Leu Lys Trp Lys Ser Asp Arg Thr Pro
            710                 715                 720 gtg tgg att gac cag tgg ccc ctt cct gaa ggt aaa ctt gta gcg cta    3705
Val Trp Ile Asp Gln Trp Pro Leu Pro Glu Gly Lys Leu Val Ala Leu
        725                 730                 735 acg caa tta gtg gaa aaa gaa tta cag tta gga cat ata gag ccc tca    3753
Thr Gln Leu Val Glu Lys Glu Leu Gln Leu Gly His Ile Glu Pro Ser
                740                 745                 750 ctt agt tgt tgg aac aca cct gtt ttt gtg atc cgg aag gct tcc ggg    3801
Leu Ser Cys Trp Asn Thr Pro Val Phe Val Ile Arg Lys Ala Ser Gly
755                 760                 765 tct tat cgc tta ttg cat gat ttg cgc gct gtt aac gcc aag ctt gtc    3849
Ser Tyr Arg Leu Leu His Asp Leu Arg Ala Val Asn Ala Lys Leu Val
770                 775                 780                 785 cct ttt ggg gcc gtc caa cag ggg gcg cca gtt ctc tcc gcg ctc ccg    3897
Pro Phe Gly Ala Val Gln Gln Gly Ala Pro Val Leu Ser Ala Leu Pro
            790                 795                 800 cgt ggc tgg ccc ctg atg gtc cta gac ctc aag gat tgc ttc ttt tct    3945
Arg Gly Trp Pro Leu Met Val Leu Asp Leu Lys Asp Cys Phe Phe Ser
        805                 810                 815 atc cct ctt gcg gaa caa gat cgc gaa gct ttt gca ttt acg ctc ccc    3993
Ile Pro Leu Ala Glu Gln Asp Arg Glu Ala Phe Ala Phe Thr Leu Pro
                820                 825                 830 tct gtg aat aac cag gcc ccc gct cga aga ttc caa tgg aag gtc ttg    4041
Ser Val Asn Asn Gln Ala Pro Ala Arg Arg Phe Gln Trp Lys Val Leu
835                 840                 845 ccc caa ggg atg acc tgt tct ccc act atc tgt cag ttg gta gtg ggt    4089
Pro Gln Gly Met Thr Cys Ser Pro Thr Ile Cys Gln Leu Val Val Gly
850                 855                 860                 865 cag gtg ctc gag ccc ttg cga ctc aag cac cca gct ctg cgc atg ttg    4137
Gln Val Leu Glu Pro Leu Arg Leu Lys His Pro Ala Leu Arg Met Leu
            870                 875                 880 cat tat atg gac gat ctt ttg cta gcc gcc tca agt cat gat ggg ttg    4185
His Tyr Met Asp Asp Leu Leu Leu Ala Ala Ser Ser His Asp Gly Leu
        885                 890                 895
```

| | | |
|---|---|---|
| gaa gcg gca ggg aag gag gtt atc ggt aca ttg gaa aga gcc ggg ttc<br>Glu Ala Ala Gly Lys Glu Val Ile Gly Thr Leu Glu Arg Ala Gly Phe<br>900 905 910 | | 4233 |
| act att tcg ccg gat aag atc cag agg gag ccc gga gta caa tat ctt<br>Thr Ile Ser Pro Asp Lys Ile Gln Arg Glu Pro Gly Val Gln Tyr Leu<br>915 920 925 | | 4281 |
| ggg tac aag tta ggc agt acg tat gta gca ccc gta ggc ttg gta gca<br>Gly Tyr Lys Leu Gly Ser Thr Tyr Val Ala Pro Val Gly Leu Val Ala<br>930 935 940 945 | | 4329 |
| gaa ccc agg ata gcc acc ttg tgg gat gtt caa aag ctg gtg ggg tca<br>Glu Pro Arg Ile Ala Thr Leu Trp Asp Val Gln Lys Leu Val Gly Ser<br>950 955 960 | | 4377 |
| ctt cag tgg ctt cgc cca gcg tta ggg atc ccg cca cga ctg atg ggt<br>Leu Gln Trp Leu Arg Pro Ala Leu Gly Ile Pro Pro Arg Leu Met Gly<br>965 970 975 | | 4425 |
| ccc ttt tat gag cag tta cga ggg tca gat cct aac gag gcg agg gaa<br>Pro Phe Tyr Glu Gln Leu Arg Gly Ser Asp Pro Asn Glu Ala Arg Glu<br>980 985 990 | | 4473 |
| tgg aat cta gac atg aaa atg gcc tgg aga gag atc gta cag ctt agc<br>Trp Asn Leu Asp Met Lys Met Ala Trp Arg Glu Ile Val Gln Leu Ser<br>995 1000 1005 | | 4521 |
| act act gct gcc ttg gaa cga tgg gac cct gcc cag cct ctg gaa<br>Thr Thr Ala Ala Leu Glu Arg Trp Asp Pro Ala Gln Pro Leu Glu<br>1010 1015 1020 | | 4566 |
| gga gcg gtc gct aga tgt gaa cag ggg gca ata ggg gtc ctg gga<br>Gly Ala Val Ala Arg Cys Glu Gln Gly Ala Ile Gly Val Leu Gly<br>1025 1030 1035 | | 4611 |
| cag gga ctg tcc aca cac cca agg cca tgt ttg tgg tta ttc tcc<br>Gln Gly Leu Ser Thr His Pro Arg Pro Cys Leu Trp Leu Phe Ser<br>1040 1045 1050 | | 4656 |
| acc caa ccc acc aag gcg ttt act gct tgg tta gaa gtg ctc acc<br>Thr Gln Pro Thr Lys Ala Phe Thr Ala Trp Leu Glu Val Leu Thr<br>1055 1060 1065 | | 4701 |
| ctt ttg att act aag cta cgc gct tcg gca gtg cga acc ttt ggc<br>Leu Leu Ile Thr Lys Leu Arg Ala Ser Ala Val Arg Thr Phe Gly<br>1070 1075 1080 | | 4746 |
| aag gag gtt gat atc ctc ctg ttg cct gca tgc ttc cgg gag gac<br>Lys Glu Val Asp Ile Leu Leu Leu Pro Ala Cys Phe Arg Glu Asp<br>1085 1090 1095 | | 4791 |
| ctt ccg ctc ccg gag ggg atc ctg tta gca ctt agg ggg ttt gca<br>Leu Pro Leu Pro Glu Gly Ile Leu Leu Ala Leu Arg Gly Phe Ala<br>1100 1105 1110 | | 4836 |
| gga aaa atc agg agt agt gac acg cca tct att ttt gac att gcg<br>Gly Lys Ile Arg Ser Ser Asp Thr Pro Ser Ile Phe Asp Ile Ala<br>1115 1120 1125 | | 4881 |
| cgt cca ctg cat gtt tct ctg aaa gtg agg gtt acc gac cac cct<br>Arg Pro Leu His Val Ser Leu Lys Val Arg Val Thr Asp His Pro<br>1130 1135 1140 | | 4926 |
| gtg ccg gga ccc act gtc ttt acc gac gcc tcc tca agc acc cat<br>Val Pro Gly Pro Thr Val Phe Thr Asp Ala Ser Ser Ser Thr His<br>1145 1150 1155 | | 4971 |
| aaa ggg gtg gta gtc tgg agg gag ggc cca agg tgg gag ata aaa<br>Lys Gly Val Val Val Trp Arg Glu Gly Pro Arg Trp Glu Ile Lys<br>1160 1165 1170 | | 5016 |
| gaa ata gtt gat ttg ggg gca agt gta caa caa ctg gag gca cgc<br>Glu Ile Val Asp Leu Gly Ala Ser Val Gln Gln Leu Glu Ala Arg<br>1175 1180 1185 | | 5061 |
| gct gtg gcc atg gca ctt ctg ctg tgg ccg aca acg ccc act aat<br>Ala Val Ala Met Ala Leu Leu Leu Trp Pro Thr Thr Pro Thr Asn<br>1190 1195 1200 | | 5106 |

| | | | | | | | | | | | | |
|---|---|---|---|---|---|---|---|---|---|---|---|---|
| gta | gtg | act | gac | tct | gcg | ttt | gtt | gcg | aaa | atg | tta | ctc | aag | atg | 5151 |
| Val | Val | Thr | Asp | Ser | Ala | Phe | Val | Ala | Lys | Met | Leu | Leu | Lys | Met | |
| 1205 | | | | 1210 | | | | | 1215 | | | | | | |

| gga | cag | gag | gga | gtc | ccg | tct | aca | gcg | gca | gct | ttt | att | tta | gag | 5196 |
|---|---|---|---|---|---|---|---|---|---|---|---|---|---|---|---|
| Gly | Gln | Glu | Gly | Val | Pro | Ser | Thr | Ala | Ala | Ala | Phe | Ile | Leu | Glu | |
| 1220 | | | | 1225 | | | | | 1230 | | | | | | |

| gat | gcg | tta | agc | caa | agg | tca | gcc | atg | gcc | gcc | gtt | ctc | cac | gtg | 5241 |
|---|---|---|---|---|---|---|---|---|---|---|---|---|---|---|---|
| Asp | Ala | Leu | Ser | Gln | Arg | Ser | Ala | Met | Ala | Ala | Val | Leu | His | Val | |
| 1235 | | | | 1240 | | | | | 1245 | | | | | | |

| cgg | agt | cat | tct | gaa | gtg | cca | ggg | ttt | ttc | aca | gaa | gga | aat | gac | 5286 |
|---|---|---|---|---|---|---|---|---|---|---|---|---|---|---|---|
| Arg | Ser | His | Ser | Glu | Val | Pro | Gly | Phe | Phe | Thr | Glu | Gly | Asn | Asp | |
| 1250 | | | | 1255 | | | | | 1260 | | | | | | |

| gtg | gca | gat | agc | caa | gcc | acc | ttt | caa | gcg | tat | ccc | ttg | aga | gag | 5331 |
|---|---|---|---|---|---|---|---|---|---|---|---|---|---|---|---|
| Val | Ala | Asp | Ser | Gln | Ala | Thr | Phe | Gln | Ala | Tyr | Pro | Leu | Arg | Glu | |
| 1265 | | | | 1270 | | | | | 1275 | | | | | | |

| gct | aaa | gat | ctt | cat | acc | gct | ctc | cat | att | gga | ccc | cgc | gcg | cta | 5376 |
|---|---|---|---|---|---|---|---|---|---|---|---|---|---|---|---|
| Ala | Lys | Asp | Leu | His | Thr | Ala | Leu | His | Ile | Gly | Pro | Arg | Ala | Leu | |
| 1280 | | | | 1285 | | | | | 1290 | | | | | | |

| tcc | aaa | gcg | tgt | aat | ata | tct | atg | cag | cag | gct | agg | gag | gtt | gtt | 5421 |
|---|---|---|---|---|---|---|---|---|---|---|---|---|---|---|---|
| Ser | Lys | Ala | Cys | Asn | Ile | Ser | Met | Gln | Gln | Ala | Arg | Glu | Val | Val | |
| 1295 | | | | 1300 | | | | | 1305 | | | | | | |

| cag | acc | tgc | ccg | cat | tgt | aat | tca | gcc | cct | gcg | ttg | gag | gcc | ggg | 5466 |
|---|---|---|---|---|---|---|---|---|---|---|---|---|---|---|---|
| Gln | Thr | Cys | Pro | His | Cys | Asn | Ser | Ala | Pro | Ala | Leu | Glu | Ala | Gly | |
| 1310 | | | | 1315 | | | | | 1320 | | | | | | |

| gta | aac | cct | agg | ggt | ttg | gga | ccc | cta | cag | ata | tgg | cag | aca | gac | 5511 |
|---|---|---|---|---|---|---|---|---|---|---|---|---|---|---|---|
| Val | Asn | Pro | Arg | Gly | Leu | Gly | Pro | Leu | Gln | Ile | Trp | Gln | Thr | Asp | |
| 1325 | | | | 1330 | | | | | 1335 | | | | | | |

| ttt | acg | ctt | gag | cct | aga | atg | gct | ccc | cgt | tcc | tgg | ctc | gct | gtt | 5556 |
|---|---|---|---|---|---|---|---|---|---|---|---|---|---|---|---|
| Phe | Thr | Leu | Glu | Pro | Arg | Met | Ala | Pro | Arg | Ser | Trp | Leu | Ala | Val | |
| 1340 | | | | 1345 | | | | | 1350 | | | | | | |

| act | gtg | gac | acc | gcc | tca | tca | gcg | ata | gtc | gta | act | cag | cat | ggc | 5601 |
|---|---|---|---|---|---|---|---|---|---|---|---|---|---|---|---|
| Thr | Val | Asp | Thr | Ala | Ser | Ser | Ala | Ile | Val | Val | Thr | Gln | His | Gly | |
| 1355 | | | | 1360 | | | | | 1365 | | | | | | |

| cgt | gtt | aca | tcg | gtt | gct | gca | caa | cat | cat | tgg | gcc | acg | gct | atc | 5646 |
|---|---|---|---|---|---|---|---|---|---|---|---|---|---|---|---|
| Arg | Val | Thr | Ser | Val | Ala | Ala | Gln | His | His | Trp | Ala | Thr | Ala | Ile | |
| 1370 | | | | 1375 | | | | | 1380 | | | | | | |

| gcc | gtt | ttg | gga | aga | cca | aag | gcc | ata | aaa | aca | gat | aac | ggg | tcc | 5691 |
|---|---|---|---|---|---|---|---|---|---|---|---|---|---|---|---|
| Ala | Val | Leu | Gly | Arg | Pro | Lys | Ala | Ile | Lys | Thr | Asp | Asn | Gly | Ser | |
| 1385 | | | | 1390 | | | | | 1395 | | | | | | |

| tgc | ttc | acg | tct | aga | tcc | acg | cgg | gag | tgg | ctc | gcg | aga | tgg | ggg | 5736 |
|---|---|---|---|---|---|---|---|---|---|---|---|---|---|---|---|
| Cys | Phe | Thr | Ser | Arg | Ser | Thr | Arg | Glu | Trp | Leu | Ala | Arg | Trp | Gly | |
| 1400 | | | | 1405 | | | | | 1410 | | | | | | |

| ata | gca | cac | acc | acc | ggg | att | ccg | gga | aat | tcc | cag | ggt | caa | gct | 5781 |
|---|---|---|---|---|---|---|---|---|---|---|---|---|---|---|---|
| Ile | Ala | His | Thr | Thr | Gly | Ile | Pro | Gly | Asn | Ser | Gln | Gly | Gln | Ala | |
| 1415 | | | | 1420 | | | | | 1425 | | | | | | |

| atg | gta | gag | cgg | gcc | aac | cgg | ctc | ctg | aaa | gat | aag | atc | cgt | gtg | 5826 |
|---|---|---|---|---|---|---|---|---|---|---|---|---|---|---|---|
| Met | Val | Glu | Arg | Ala | Asn | Arg | Leu | Leu | Lys | Asp | Lys | Ile | Arg | Val | |
| 1430 | | | | 1435 | | | | | 1440 | | | | | | |

| ctt | gcg | gag | ggg | gac | ggc | ttt | atg | aaa | aga | atc | ccc | gcc | agc | aaa | 5871 |
|---|---|---|---|---|---|---|---|---|---|---|---|---|---|---|---|
| Leu | Ala | Glu | Gly | Asp | Gly | Phe | Met | Lys | Arg | Ile | Pro | Ala | Ser | Lys | |
| 1445 | | | | 1450 | | | | | 1455 | | | | | | |

| cag | ggg | gaa | cta | cta | gcc | aag | gca | atg | tat | gcc | ctc | aat | cac | ttt | 5916 |
|---|---|---|---|---|---|---|---|---|---|---|---|---|---|---|---|
| Gln | Gly | Glu | Leu | Leu | Ala | Lys | Ala | Met | Tyr | Ala | Leu | Asn | His | Phe | |
| 1460 | | | | 1465 | | | | | 1470 | | | | | | |

| gag | cgt | ggt | gaa | aac | aca | aaa | aca | ccg | gta | caa | aaa | cac | tgg | aga | 5961 |
|---|---|---|---|---|---|---|---|---|---|---|---|---|---|---|---|
| Glu | Arg | Gly | Glu | Asn | Thr | Lys | Thr | Pro | Val | Gln | Lys | His | Trp | Arg | |
| 1475 | | | | 1480 | | | | | 1485 | | | | | | |

| cct | acc | gtt | ctt | aca | gaa | gga | ccc | ccg | gtt | aaa | ata | cga | ata | gag | 6006 |
|---|---|---|---|---|---|---|---|---|---|---|---|---|---|---|---|
| Pro | Thr | Val | Leu | Thr | Glu | Gly | Pro | Pro | Val | Lys | Ile | Arg | Ile | Glu | |
| 1490 | | | | 1495 | | | | | 1500 | | | | | | |

-continued

| aca | ggg | gag | tgg | gaa | aaa | gga | tgg | aac | gtg | ctg | gtc | tgg | gga | cga | 6051 |
| Thr | Gly | Glu | Trp | Glu | Lys | Gly | Trp | Asn | Val | Leu | Val | Trp | Gly | Arg | |
| 1505 | | | | 1510 | | | | | 1515 | | | | | | |

| ggt | tat | gcc | gct | gtg | aaa | aac | agg | gac | act | gat | aag | gtt | att | tgg | 6096 |
| Gly | Tyr | Ala | Ala | Val | Lys | Asn | Arg | Asp | Thr | Asp | Lys | Val | Ile | Trp | |
| 1520 | | | | | 1525 | | | | | 1530 | | | | | |

| gta | ccc | tct | cgg | aaa | gtt | aaa | ccg | gat | gtc | acc | caa | aag | gat | gag | 6141 |
| Val | Pro | Ser | Arg | Lys | Val | Lys | Pro | Asp | Val | Thr | Gln | Lys | Asp | Glu | |
| 1535 | | | | | 1540 | | | | | 1545 | | | | | |

| gtg | act | aag | aaa | gat | gag | gcg | agc | cct | ctt | ttt | gca | ggc | att | tct | 6186 |
| Val | Thr | Lys | Lys | Asp | Glu | Ala | Ser | Pro | Leu | Phe | Ala | Gly | Ile | Ser | |
| 1550 | | | | | 1555 | | | | | 1560 | | | | | |

| gac | tgg | ata | ccc | tgg | gaa | gac | gag | caa | gaa | gga | ctc | caa | gga | gaa | 6231 |
| Asp | Trp | Ile | Pro | Trp | Glu | Asp | Glu | Gln | Glu | Gly | Leu | Gln | Gly | Glu | |
| 1565 | | | | | 1570 | | | | | 1575 | | | | | |

| acc | gct | agc | aac | aag | caa | gaa | aga | ccc | gga | gaa | gac | acc | ctt | gct | 6276 |
| Thr | Ala | Ser | Asn | Lys | Gln | Glu | Arg | Pro | Gly | Glu | Asp | Thr | Leu | Ala | |
| 1580 | | | | | 1585 | | | | | 1590 | | | | | |

| gcc | aac | gag | agt | taa | gaattctgca | gatatccagc | acagtggcgg | ccgctcgagt | 6331 |
| Ala | Asn | Glu | Ser | | | | | | |
| 1595 | | | | | | | | | |

| ctagagggcc | cgtttaaacc | cgctgatcag | cctcgactgt | gccttctagt | tgccagccat | 6391 |
| ctgttgtttg | cccctccccc | gtgccttcct | gacccctgga | aggtgccact | cccactgtcc | 6451 |
| tttcctaata | aaatgaggaa | attgcatcgc | attgtctgag | taggtgtcat | tctattctgg | 6511 |
| ggggtggggt | ggggcaggac | agcaagggg | aggattggga | agacaatagc | aggcatgctg | 6571 |
| gggatgcggt | gggctctatg | gcttctgagg | cggaaagaac | cagctggggc | tctagggggt | 6631 |
| atccccacgc | gccctgtagc | ggcgcattaa | gcgcggcggg | tgtggtggtt | acgcgcagcg | 6691 |
| tgaccgctac | acttgccagc | gccctagcgc | ccgctccttt | cgctttcttc | ccttcctttc | 6751 |
| tcgccacgtt | cgccggcttt | ccccgtcaag | ctctaaatcg | ggggctccct | ttagggttcc | 6811 |
| gatttagtgc | tttacggcac | ctcgacccca | aaaaacttga | ttagggtgat | ggttcacgta | 6871 |
| gtgggccatc | gccctgatag | acggtttttc | gccctttgac | gttggagtcc | acgttcttta | 6931 |
| atagtggact | cttgttccaa | actggaacaa | cactcaaccc | tatctcggtc | tattcttttg | 6991 |
| atttataagg | gattttgccg | atttcggcct | attggttaaa | aaatgagctg | atttaacaaa | 7051 |
| aatttaacgc | gaattaattc | tgtggaatgt | gtgtcagtta | gggtgtggaa | agtccccagg | 7111 |
| ctccccagca | ggcagaagta | tgcaaagcat | gcatctcaat | tagtcagcaa | ccaggtgtgg | 7171 |
| aaagtcccca | ggctccccag | caggcagaag | tatgcaaagc | atgcatctca | attagtcagc | 7231 |
| aaccatagtc | ccgcccctaa | ctccgcccat | cccgccccta | actccgccca | gttccgccca | 7291 |
| ttctccgccc | catggctgac | taatttttt | tatttatgca | gaggccgagg | ccgcctctgc | 7351 |
| ctctgagcta | ttccagaagt | agtgaggagg | cttttttgga | ggcctaggct | tttgcaaaaa | 7411 |
| gctcccggga | gcttgtatat | ccattttcgg | atctgatcaa | gagacaggat | gaggatcgtt | 7471 |
| tcgcatgatt | gaacaagatg | gattgcacgc | aggttctccg | gccgcttggg | tggagaggct | 7531 |
| attcggctat | gactgggcac | aacagacaat | cggctgctct | gatgccgccg | tgttccggct | 7591 |
| gtcagcgcag | gggcgcccgg | ttctttttgt | caagaccgac | ctgtccggtg | ccctgaatga | 7651 |
| actgcaggac | gaggcagcgc | ggctatcgtg | gctggccacg | acgggcgttc | cttgcgcagc | 7711 |
| tgtgctcgac | gttgtcactg | aagcgggaag | ggactggctg | ctattgggcg | aagtgccggg | 7771 |
| gcaggatctc | ctgtcatctc | accttgctcc | tgccgagaaa | gtatccatca | tggctgatgc | 7831 |
| aatgcggcgg | ctgcatacgc | ttgatccggc | tacctgccca | ttcgaccacc | aagcgaaaca | 7891 |

```
tcgcatcgag cgagcacgta ctcggatgga agccggtctt gtcgatcagg atgatctgga   7951
cgaagagcat caggggctcg cgccagccga actgttcgcc aggctcaagg cgcgcatgcc   8011
cgacggcgag gatctcgtcg tgacccatgg cgatgcctgc ttgccgaata tcatggtgga   8071
aaatggccgc ttttctggat tcatcgactg tggccggctg ggtgtggcgg accgctatca   8131
ggacatagcg ttggctaccc gtgatattgc tgaagagctt ggcggcgaat gggctgaccg   8191
cttcctcgtg ctttacggta tcgccgctcc cgattcgcag cgcatcgcct tctatcgcct   8251
tcttgacgag ttcttctgag cgggactctg gggttcgaaa tgaccgacca agcgacgccc   8311
aacctgccat cacgagattt cgattccacc gccgccttct atgaaaggtt gggcttcgga   8371
atcgttttcc gggacgccgg ctggatgatc ctccagcgcg gggatctcat gctggagttc   8431
ttcgcccacc ccaacttgtt tattgcagct tataatggtt acaaataaag caatagcatc   8491
acaaatttca caaataaagc attttttttca ctgcattcta gttgtggttt gtccaaactc   8551
atcaatgtat cttatcatgt ctgtataccg tcgacctcta gctagagctt ggcgtaatca   8611
tggtcatagc tgtttcctgt gtgaaattgt tatccgctca caattccaca acatacga    8671 gccggaagca taaagtgtaa agcctggggt gcctaatgag tgagctaact cacattaatt   8731
gcgttgcgct cactgcccgc tttccagtcg ggaaacctgt cgtgccagct gcattaatga   8791
atcggccaac gcgcggggag aggcggtttg cgtattgggc gctcttccgc ttcctcgctc   8851
actgactcgc tgcgctcggt cgttcggctg cggcgagcgg tatcagctca ctcaaaggcg   8911
gtaatacggt tatccacaga atcagggggat aacgcaggaa agaacatgtg agcaaaaggc   8971
cagcaaaagg ccaggaaccg taaaaaggcc gcgttgctgg cgtttttcca taggctccgc   9031 cccctgacg agcatcacaa aaatcgacgc tcaagtcaga ggtggcgaaa cccgacagga   9091
ctataaagat accaggcgtt tccccctgga agctccctcg tgcgctctcc tgttccgacc   9151
ctgccgctta ccggatacct gtccgccttt ctcccttcgg gaagcgtggc gctttctcat   9211
agctcacgct gtaggtatct cagttcggtg taggtcgttc gctccaagct gggctgtgtg   9271
cacgaacccc ccgttcagcc cgaccgctgc gccttatccg gtaactatcg tcttgagtcc   9331
aacccggtaa gacacgactt atcgccactg gcagcagcca ctggtaacag gattagcaga   9391
gcgaggtatg taggcggtgc tacagagttc ttgaagtggt ggcctaacta cggctacact   9451
agaagaacag tatttggtat ctgcgctctg ctgaagccag ttaccttcgg aaaaagagtt   9511
ggtagctctt gatccggcaa acaaaccacc gctggtagcg gtttttttgt ttgcaagcag   9571
cagattacgc gcagaaaaaa aggatctcaa gaagatcctt tgatcttttc tacgggtct   9631 gacgctcagt ggaacgaaaa ctcacgttaa gggattttgg tcatgagatt atcaaaaagg   9691
atcttcacct agatcctttt aaattaaaaa tgaagtttta aatcaatcta agtatatat   9751 gagtaaactt ggtctgacag ttaccaatgc ttaatcagtg aggcacctat ctcagcgatc   9811
tgtctatttc gttcatccat agttgcctga ctccccgtcg tgtagataac tacgatacgg   9871
gagggcttac catctggccc cagtgctgca atgataccgc gagacccacg ctcaccggct   9931
ccagatttat cagcaataaa ccagccagcc ggaagggccg agcgcagaag tggtcctgca   9991
actttatccg cctccatcca gtctattaat tgttgccggg aagctagagt aagtagttcg  10051
ccagttaata gtttgcgcaa cgttgttgcc attgctacag gcatcgtggt gtcacgctcg  10111
tcgtttggta tggcttcatt cagctccggt tcccaacgat caaggcgagt tacatgatcc  10171
cccatgttgt gcaaaaaagc ggttagctcc ttcggtcctc cgatcgttgt cagaagtaag  10231
ttggccgcag tgttatcact catggttatg gcagcactgc ataattctct tactgtcatg  10291
```

-continued

```
ccatccgtaa gatgcttttc tgtgactggt gagtactcaa ccaagtcatt ctgagaatag    10351
tgtatgcggc gaccgagttg ctcttgcccg gcgtcaatac gggataatac cgcgccacat    10411
agcagaactt taaaagtgct catcattgga aaacgttctt cggggcgaaa actctcaagg    10471
atcttaccgc tgttgagatc cagttcgatg taacccactc gtgcacccaa ctgatcttca    10531
gcatctttta ctttcaccag cgtttctggg tgagcaaaaa caggaaggca aaatgccgca    10591
aaaaagggaa taagggcgac acggaaatgt tgaatactca tactcttcct ttttcaatat    10651
tattgaagca tttatcaggg ttattgtctc atgagcggat acatatttga atgtatttag    10711
aaaaataaac aaatagggggt tccgcgcaca tttccccgaa aagtgccacc tgacgtc      10768
```

<210> SEQ ID NO 12
<211> LENGTH: 703
<212> TYPE: PRT
<213> ORGANISM: Artificial Sequence
<220> FEATURE:
<223> OTHER INFORMATION: Synthetic Construct

<400> SEQUENCE: 12

```
Met Glu Ala Val Ile Lys Val Ile Ser Ser Ala Cys Lys Thr Tyr Cys
1               5                   10                  15

Gly Lys Ile Ser Pro Ser Lys Lys Glu Ile Gly Ala Met Leu Ser Leu
            20                  25                  30

Leu Gln Lys Glu Gly Leu Leu Met Ser Pro Ser Asp Leu Tyr Ser Pro
        35                  40                  45

Gly Ser Trp Asp Pro Ile Thr Ala Ala Leu Ser Gln Arg Ala Met Val
    50                  55                  60

Leu Gly Lys Ser Gly Glu Leu Lys Thr Trp Gly Leu Val Leu Gly Ala
65                  70                  75                  80

Leu Lys Ala Ala Arg Glu Gln Val Thr Ser Glu Gln Ala Lys Phe
                85                  90                  95

Trp Leu Gly Leu Gly Gly Arg Val Ser Pro Gly Pro Glu Cys
            100                 105                 110

Ile Glu Lys Pro Ala Thr Glu Arg Arg Ile Asp Lys Gly Glu Glu Val
        115                 120                 125

Gly Glu Thr Thr Val Gln Arg Asp Ala Lys Met Ala Pro Glu Glu Ala
    130                 135                 140

Ala Thr Pro Lys Thr Val Gly Thr Ser Cys Tyr His Cys Gly Thr Ala
145                 150                 155                 160

Val Gly Cys Asn Cys Ala Thr Ala Thr Ala Ser Ala Pro Pro Pro
                165                 170                 175

Tyr Val Gly Ser Gly Leu Tyr Pro Ser Leu Ala Gly Val Gly Glu Gln
            180                 185                 190

Gln Gly Gln Gly Asp Asn Thr Ser Arg Gly Ala Glu Gln Pro Arg Glu
        195                 200                 205

Glu Pro Gly His Ala Gly Gln Ala Pro Gly Pro Ala Leu Thr Asp Trp
    210                 215                 220

Ala Arg Val Arg Glu Glu Leu Ala Ser Thr Gly Pro Pro Val Val Ala
225                 230                 235                 240

Met Pro Val Val Ile Lys Thr Glu Gly Pro Ala Trp Thr Pro Leu Glu
                245                 250                 255

Pro Lys Leu Ile Thr Arg Leu Ala Asp Thr Val Arg Thr Lys Gly Leu
            260                 265                 270

Arg Ser Pro Ile Thr Met Ala Glu Val Glu Ala Leu Met Ser Ser Pro
        275                 280                 285
```

```
Leu Leu Pro His Asp Val Thr Asn Leu Met Arg Val Ile Leu Gly Pro
            290                 295                 300

Ala Pro Tyr Ala Leu Trp Met Asp Ala Trp Gly Val Gln Leu Gln Thr
305                 310                 315                 320

Val Ile Ala Ala Ala Thr Arg Asp Pro Arg His Pro Ala Asn Gly Gln
                325                 330                 335

Gly Arg Gly Glu Arg Thr Asn Leu Asp Arg Leu Lys Gly Leu Ala Asp
            340                 345                 350

Gly Met Val Gly Asn Pro Gln Gly Gln Ala Ala Leu Leu Arg Pro Gly
                355                 360                 365

Glu Leu Val Ala Ile Thr Ala Ser Ala Leu Gln Ala Phe Arg Glu Val
            370                 375                 380

Ala Arg Leu Ala Glu Pro Ala Gly Pro Trp Ala Asp Ile Thr Gln Gly
385                 390                 395                 400

Pro Ser Glu Ser Phe Val Asp Phe Ala Asn Arg Leu Ile Lys Ala Val
                405                 410                 415

Glu Gly Ser Asp Leu Pro Pro Ser Ala Arg Ala Pro Val Ile Ile Asp
            420                 425                 430

Cys Phe Arg Gln Lys Ser Gln Pro Asp Ile Gln Gln Leu Ile Arg Ala
                435                 440                 445

Ala Pro Ser Thr Leu Thr Thr Pro Gly Glu Ile Ile Lys Tyr Val Leu
450                 455                 460

Asp Arg Gln Lys Ile Ala Pro Leu Thr Asp Gln Gly Ile Ala Ala Ala
465                 470                 475                 480

Met Ser Ser Ala Ile Gln Pro Leu Val Met Ala Val Val Asn Arg Glu
                485                 490                 495

Arg Asp Gly Gln Thr Gly Ser Gly Gly Arg Ala Arg Gly Leu Cys Tyr
            500                 505                 510

Thr Cys Gly Ser Pro Gly His Tyr Gln Ala Gln Cys Pro Lys Lys Arg
            515                 520                 525

Lys Ser Gly Asn Ser Arg Glu Arg Cys Gln Leu Cys Asp Gly Met Gly
            530                 535                 540

His Asn Ala Lys Gln Cys Arg Lys Arg Asp Gly Asn Gln Gly Gln Arg
545                 550                 555                 560

Pro Gly Arg Gly Leu Ser Ser Gly Pro Trp Pro Gly Pro Glu Gln Pro
                565                 570                 575

Ala Val Ser Leu Ala Met Thr Met Glu His Lys Asp Arg Pro Leu Val
            580                 585                 590

Arg Val Ile Leu Thr Asn Thr Gly Ser His Pro Val Lys Gln Arg Ser
            595                 600                 605

Val Tyr Ile Thr Ala Leu Leu Asp Ser Gly Ala Asp Ile Thr Ile Ile
            610                 615                 620

Ser Glu Glu Asp Trp Pro Thr Asp Trp Pro Val Val Asp Thr Ala Asn
625                 630                 635                 640

Pro Gln Ile His Gly Ile Gly Gly Gly Ile Pro Met Arg Lys Ser Arg
                645                 650                 655

Asp Met Ile Glu Val Gly Val Ile Asn Arg Asp Gly Ser Leu Glu Arg
                660                 665                 670

Pro Leu Leu Leu Phe Pro Ala Val Ala Met Val Arg Gly Ser Ile Leu
            675                 680                 685

Gly Arg Asp Cys Leu Gln Gly Leu Gly Leu Arg Leu Thr Asn Leu
            690                 695                 700
```

<210> SEQ ID NO 13

```
<211> LENGTH: 895
<212> TYPE: PRT
<213> ORGANISM: Artificial Sequence
<220> FEATURE:
<223> OTHER INFORMATION: Synthetic Construct

<400> SEQUENCE: 13
```

| | | | | | | | | | | | | | | |
|---|---|---|---|---|---|---|---|---|---|---|---|---|---|---|
| Thr | Val | Ala | Leu | His | Leu | Ala | Ile | Pro | Leu | Lys | Trp | Lys | Ser | Asp | Arg |
| 1 | | | | 5 | | | | | 10 | | | | | 15 | |
| Thr | Pro | Val | Trp | Ile | Asp | Gln | Trp | Pro | Leu | Pro | Glu | Gly | Lys | Leu | Val |
| | | | 20 | | | | | 25 | | | | | 30 | | |
| Ala | Leu | Thr | Gln | Leu | Val | Glu | Lys | Glu | Leu | Gln | Leu | Gly | His | Ile | Glu |
| | | 35 | | | | | 40 | | | | | 45 | | | |
| Pro | Ser | Leu | Ser | Cys | Trp | Asn | Thr | Pro | Val | Phe | Val | Ile | Arg | Lys | Ala |
| 50 | | | | | 55 | | | | | 60 | | | | | |
| Ser | Gly | Ser | Tyr | Arg | Leu | Leu | His | Asp | Leu | Arg | Ala | Val | Asn | Ala | Lys |
| 65 | | | | | 70 | | | | | 75 | | | | | 80 |
| Leu | Val | Pro | Phe | Gly | Ala | Val | Gln | Gln | Gly | Ala | Pro | Val | Leu | Ser | Ala |
| | | | | 85 | | | | | 90 | | | | | 95 | |
| Leu | Pro | Arg | Gly | Trp | Pro | Leu | Met | Val | Leu | Asp | Leu | Lys | Asp | Cys | Phe |
| | | | 100 | | | | | 105 | | | | | 110 | | |
| Phe | Ser | Ile | Pro | Leu | Ala | Glu | Gln | Asp | Arg | Glu | Ala | Phe | Ala | Phe | Thr |
| | | 115 | | | | | 120 | | | | | 125 | | | |
| Leu | Pro | Ser | Val | Asn | Asn | Gln | Ala | Pro | Ala | Arg | Arg | Phe | Gln | Trp | Lys |
| | 130 | | | | | 135 | | | | | 140 | | | | |
| Val | Leu | Pro | Gln | Gly | Met | Thr | Cys | Ser | Pro | Thr | Ile | Cys | Gln | Leu | Val |
| 145 | | | | | 150 | | | | | 155 | | | | | 160 |
| Val | Gly | Gln | Val | Leu | Glu | Pro | Leu | Arg | Leu | Lys | His | Pro | Ala | Leu | Arg |
| | | | | 165 | | | | | 170 | | | | | 175 | |
| Met | Leu | His | Tyr | Met | Asp | Asp | Leu | Leu | Leu | Ala | Ala | Ser | Ser | His | Asp |
| | | | | 180 | | | | | 185 | | | | | 190 | |
| Gly | Leu | Glu | Ala | Ala | Gly | Lys | Glu | Val | Ile | Gly | Thr | Leu | Glu | Arg | Ala |
| | | 195 | | | | | 200 | | | | | 205 | | | |
| Gly | Phe | Thr | Ile | Ser | Pro | Asp | Lys | Ile | Gln | Arg | Glu | Pro | Gly | Val | Gln |
| | 210 | | | | | 215 | | | | | 220 | | | | |
| Tyr | Leu | Gly | Tyr | Lys | Leu | Gly | Ser | Thr | Tyr | Val | Ala | Pro | Val | Gly | Leu |
| 225 | | | | | 230 | | | | | 235 | | | | | 240 |
| Val | Ala | Glu | Pro | Arg | Ile | Ala | Thr | Leu | Trp | Asp | Val | Gln | Lys | Leu | Val |
| | | | | 245 | | | | | 250 | | | | | 255 | |
| Gly | Ser | Leu | Gln | Trp | Leu | Arg | Pro | Ala | Leu | Gly | Ile | Pro | Pro | Arg | Leu |
| | | | 260 | | | | | 265 | | | | | 270 | | |
| Met | Gly | Pro | Phe | Tyr | Glu | Gln | Leu | Arg | Gly | Ser | Asp | Pro | Asn | Glu | Ala |
| | | 275 | | | | | 280 | | | | | 285 | | | |
| Arg | Glu | Trp | Asn | Leu | Asp | Met | Lys | Met | Ala | Trp | Arg | Glu | Ile | Val | Gln |
| | 290 | | | | | 295 | | | | | 300 | | | | |
| Leu | Ser | Thr | Thr | Ala | Ala | Leu | Glu | Arg | Trp | Asp | Pro | Ala | Gln | Pro | Leu |
| 305 | | | | | 310 | | | | | 315 | | | | | 320 |
| Glu | Gly | Ala | Val | Ala | Arg | Cys | Glu | Gln | Gly | Ala | Ile | Gly | Val | Leu | Gly |
| | | | | 325 | | | | | 330 | | | | | 335 | |
| Gln | Gly | Leu | Ser | Thr | His | Pro | Arg | Pro | Cys | Leu | Trp | Leu | Phe | Ser | Thr |
| | | | | 340 | | | | | 345 | | | | | 350 | |
| Gln | Pro | Thr | Lys | Ala | Phe | Thr | Ala | Trp | Leu | Glu | Val | Leu | Thr | Leu | Leu |
| | | 355 | | | | | 360 | | | | | 365 | | | |
| Ile | Thr | Lys | Leu | Arg | Ala | Ser | Ala | Val | Arg | Thr | Phe | Gly | Lys | Glu | Val |
| | 370 | | | | | 375 | | | | | 380 | | | | |

```
Asp Ile Leu Leu Leu Pro Ala Cys Phe Arg Glu Asp Leu Pro Leu Pro
385                 390                 395                 400
Glu Gly Ile Leu Leu Ala Leu Arg Gly Phe Ala Gly Lys Ile Arg Ser
            405                 410                 415
Ser Asp Thr Pro Ser Ile Phe Asp Ile Ala Arg Pro Leu His Val Ser
        420                 425                 430
Leu Lys Val Arg Val Thr Asp His Pro Val Pro Gly Pro Thr Val Phe
    435                 440                 445
Thr Asp Ala Ser Ser Ser Thr His Lys Gly Val Val Trp Arg Glu
450                 455                 460
Gly Pro Arg Trp Glu Ile Lys Glu Ile Val Asp Leu Gly Ala Ser Val
465                 470                 475                 480
Gln Gln Leu Glu Ala Arg Ala Val Ala Met Ala Leu Leu Leu Trp Pro
                485                 490                 495
Thr Thr Pro Thr Asn Val Val Thr Asp Ser Ala Phe Val Ala Lys Met
            500                 505                 510
Leu Leu Lys Met Gly Gln Glu Gly Val Pro Ser Thr Ala Ala Ala Phe
    515                 520                 525
Ile Leu Glu Asp Ala Leu Ser Gln Arg Ser Ala Met Ala Ala Val Leu
530                 535                 540
His Val Arg Ser His Ser Glu Val Pro Gly Phe Phe Thr Glu Gly Asn
545                 550                 555                 560
Asp Val Ala Asp Ser Gln Ala Thr Phe Gln Ala Tyr Pro Leu Arg Glu
                565                 570                 575
Ala Lys Asp Leu His Thr Ala Leu His Ile Gly Pro Arg Ala Leu Ser
            580                 585                 590
Lys Ala Cys Asn Ile Ser Met Gln Gln Ala Arg Glu Val Val Gln Thr
        595                 600                 605
Cys Pro His Cys Asn Ser Ala Pro Ala Leu Glu Ala Gly Val Asn Pro
    610                 615                 620
Arg Gly Leu Gly Pro Leu Gln Ile Trp Gln Thr Asp Phe Thr Leu Glu
625                 630                 635                 640
Pro Arg Met Ala Pro Arg Ser Trp Leu Ala Val Thr Val Asp Thr Ala
                645                 650                 655
Ser Ser Ala Ile Val Val Thr Gln His Gly Arg Val Thr Ser Val Ala
            660                 665                 670
Ala Gln His His Trp Ala Thr Ala Ile Ala Val Leu Gly Arg Pro Lys
        675                 680                 685
Ala Ile Lys Thr Asp Asn Gly Ser Cys Phe Thr Ser Arg Ser Thr Arg
    690                 695                 700
Glu Trp Leu Ala Arg Trp Gly Ile Ala His Thr Thr Gly Ile Pro Gly
705                 710                 715                 720
Asn Ser Gln Gly Gln Ala Met Val Glu Arg Ala Asn Arg Leu Leu Lys
                725                 730                 735
Asp Lys Ile Arg Val Leu Ala Glu Gly Asp Gly Phe Met Lys Arg Ile
            740                 745                 750
Pro Ala Ser Lys Gln Gly Glu Leu Leu Ala Lys Ala Met Tyr Ala Leu
        755                 760                 765
Asn His Phe Glu Arg Gly Glu Asn Thr Lys Thr Pro Val Gln Lys His
    770                 775                 780
Trp Arg Pro Thr Val Leu Thr Glu Gly Pro Pro Val Lys Ile Arg Ile
785                 790                 795                 800
Glu Thr Gly Glu Trp Glu Lys Gly Trp Asn Val Leu Val Trp Gly Arg
                805                 810                 815
```

```
Gly Tyr Ala Ala Val Lys Asn Arg Asp Thr Asp Lys Val Ile Trp Val
            820                 825                 830

Pro Ser Arg Lys Val Lys Pro Asp Val Thr Gln Lys Asp Glu Val Thr
        835                 840                 845

Lys Lys Asp Glu Ala Ser Pro Leu Phe Ala Gly Ile Ser Asp Trp Ile
    850                 855                 860

Pro Trp Glu Asp Glu Gln Glu Gly Leu Gln Gly Glu Thr Ala Ser Asn
865                 870                 875                 880

Lys Gln Glu Arg Pro Gly Glu Asp Thr Leu Ala Ala Asn Glu Ser
                885                 890                 895

<210> SEQ ID NO 14
<211> LENGTH: 10768
<212> TYPE: DNA
<213> ORGANISM: Artificial Sequence
<220> FEATURE:
<223> OTHER INFORMATION: /note="SEQ ID NO: 14: 1. helper plasmid for
      codon optimized gag-pol"
<220> FEATURE:
<221> NAME/KEY: promoter
<222> LOCATION: (232)..(819)
<223> OTHER INFORMATION: promoter of CMV
<220> FEATURE:
<221> NAME/KEY: Intron
<222> LOCATION: (907)..(1463)
<223> OTHER INFORMATION: intron of beta-globin
<220> FEATURE:
<221> NAME/KEY: CDS
<222> LOCATION: (1475)..(3586)
<223> OTHER INFORMATION: gal: coding sequence for Gal, codon optimized
<220> FEATURE:
<221> NAME/KEY: misc_feature
<222> LOCATION: (3437)..(3737)
<223> OTHER INFORMATION: transition region between regions coding for
      gag and pol (wild-type)
<220> FEATURE:
<221> NAME/KEY: misc_feature
<222> LOCATION: (3574)..(3723)
<223> OTHER INFORMATION: signal for change of reading frame (frameshift
      signal)
<220> FEATURE:
<221> NAME/KEY: CDS
<222> LOCATION: (3604)..(6291)
<223> OTHER INFORMATION: pol: coding sequence for Pol, codon optimized
<220> FEATURE:
<221> NAME/KEY: polyA_signal
<222> LOCATION: (6368)..(6588)
<223> OTHER INFORMATION: poly adenylation signal of bGH

<400> SEQUENCE: 14
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat cctgagaact tcagggtgag tctatgggac ccttgatgtt ttcttttccc    960
ttcttttcta tggttaagtt catgtcatag gaagggagaa agtaacaggg tacacatatt   1020
gaccaaatca gggtaatttt gcatttgtaa tttaaaaaa tgctttcttc ttttaatata   1080
cttttttgtt tatcttattt ctaatacttt ccctaatctc tttctttcag gcaataatg   1140 atacaatgta tcatgcctct ttgcaccatt ctaaagaata acagtgataa tttctgggtt   1200
aaggcaatag caatatttct gcatataaat atttctgcat ataaattgta actgatgtaa   1260
gaggtttcat attgctaata gcagctacaa tccagctacc attctgcttt tattttatgg   1320
ttgggataag gctggattat tctgagtcca agctaggccc ttttgctaat catgttcata   1380
cctcttatct tcctcccaca gctcctgggc aacgtgctgg tctgtgtgct ggcccatcac   1440
tttggcaaag cacgtgagat ctgaattcgc cacc atg gaa gcc gtg atc aaa gtg   1495
                                    Met Glu Ala Val Ile Lys Val
                                    1               5
```

| | | | | | | | | | | | | | | | | |
|---|---|---|---|---|---|---|---|---|---|---|---|---|---|---|---|---|
| atc | agc | agc | gcc | tgc | aag | acc | tac | tgc | ggc | aag | atc | agc | ccc | agc | aag | 1543 |
| Ile | Ser | Ser | Ala | Cys | Lys | Thr | Tyr | Cys | Gly | Lys | Ile | Ser | Pro | Ser | Lys | |
| | | 10 | | | | 15 | | | | | 20 | | | | | |

| | | | | | | | | | | | | | | | | |
|---|---|---|---|---|---|---|---|---|---|---|---|---|---|---|---|---|
| aaa | gaa | atc | ggc | gct | atg | ctg | tct | ctc | ctg | caa | aag | gaa | ggc | ctg | ctg | 1591 |
| Lys | Glu | Ile | Gly | Ala | Met | Leu | Ser | Leu | Leu | Gln | Lys | Glu | Gly | Leu | Leu | |
| | 25 | | | | | 30 | | | | | 35 | | | | | |

| | | | | | | | | | | | | | | | | |
|---|---|---|---|---|---|---|---|---|---|---|---|---|---|---|---|---|
| atg | agc | ccc | agc | gac | ctg | tac | agc | ccc | ggc | agc | tgg | gat | cct | atc | aca | 1639 |
| Met | Ser | Pro | Ser | Asp | Leu | Tyr | Ser | Pro | Gly | Ser | Trp | Asp | Pro | Ile | Thr | |
| 40 | | | | 45 | | | | | 50 | | | | | 55 | | |

| | | | | | | | | | | | | | | | | |
|---|---|---|---|---|---|---|---|---|---|---|---|---|---|---|---|---|
| gcc | gcc | ctg | agc | cag | agg | gcc | atg | gtg | ctg | ggc | aag | agc | ggc | gag | ctg | 1687 |
| Ala | Ala | Leu | Ser | Gln | Arg | Ala | Met | Val | Leu | Gly | Lys | Ser | Gly | Glu | Leu | |
| | | | | 60 | | | | | 65 | | | | | 70 | | |

| | | | | | | | | | | | | | | | | |
|---|---|---|---|---|---|---|---|---|---|---|---|---|---|---|---|---|
| aaa | acc | tgg | ggg | ctg | gtg | ctg | gga | gcc | ctg | aag | gcc | gcc | aga | gaa | gaa | 1735 |
| Lys | Thr | Trp | Gly | Leu | Val | Leu | Gly | Ala | Leu | Lys | Ala | Ala | Arg | Glu | Glu | |
| | | | 75 | | | | | 80 | | | | | 85 | | | |

| | | | | | | | | | | | | | | | | |
|---|---|---|---|---|---|---|---|---|---|---|---|---|---|---|---|---|
| cag | gtg | acc | agc | gag | cag | gcc | aag | ttt | tgg | ctg | ggc | ctg | ggc | gga | gga | 1783 |
| Gln | Val | Thr | Ser | Glu | Gln | Ala | Lys | Phe | Trp | Leu | Gly | Leu | Gly | Gly | Gly | |
| | | | 90 | | | | | 95 | | | | | 100 | | | |

| | | | | | | | | | | | | | | | | |
|---|---|---|---|---|---|---|---|---|---|---|---|---|---|---|---|---|
| aga | gtg | tct | ccc | cct | ggc | ccc | gag | tgt | atc | gag | aag | ccc | gcc | acc | gag | 1831 |
| Arg | Val | Ser | Pro | Pro | Gly | Pro | Glu | Cys | Ile | Glu | Lys | Pro | Ala | Thr | Glu | |
| | | 105 | | | | | 110 | | | | | 115 | | | | |

| | | | | | | | | | | | | | | | | |
|---|---|---|---|---|---|---|---|---|---|---|---|---|---|---|---|---|
| cgg | aga | atc | gac | aag | ggc | gag | gaa | gtg | ggc | gag | aca | acc | gtg | cag | cgg | 1879 |
| Arg | Arg | Ile | Asp | Lys | Gly | Glu | Glu | Val | Gly | Glu | Thr | Thr | Val | Gln | Arg | |
| 120 | | | | 125 | | | | | 130 | | | | | 135 | | |

| | | | | | | | | | | | | | | | | |
|---|---|---|---|---|---|---|---|---|---|---|---|---|---|---|---|---|
| gac | gcc | aag | atg | gcc | cct | gag | gaa | gcc | gcc | acc | cct | aag | acc | gtg | ggc | 1927 |
| Asp | Ala | Lys | Met | Ala | Pro | Glu | Glu | Ala | Ala | Thr | Pro | Lys | Thr | Val | Gly | |
| | | | | 140 | | | | | 145 | | | | | 150 | | |

| | | | | | | | | | | | | | | | | |
|---|---|---|---|---|---|---|---|---|---|---|---|---|---|---|---|---|
| acc | agc | tgc | tac | cac | tgt | ggc | acc | gcc | gtg | ggc | tgt | aat | tgt | gcc | acc | 1975 |
| Thr | Ser | Cys | Tyr | His | Cys | Gly | Thr | Ala | Val | Gly | Cys | Asn | Cys | Ala | Thr | |
| | | | | 155 | | | | | 160 | | | | | 165 | | |

| | | | | | | | | | | | | | | | | |
|---|---|---|---|---|---|---|---|---|---|---|---|---|---|---|---|---|
| gcc | acc | gcc | tct | gcc | cct | cct | cct | cct | tac | gtg | ggc | agc | ggc | ctg | tat | 2023 |
| Ala | Thr | Ala | Ser | Ala | Pro | Pro | Pro | Pro | Tyr | Val | Gly | Ser | Gly | Leu | Tyr | |
| | | 170 | | | | | 175 | | | | | 180 | | | | |

| | | | | | | | | | | | | | | | | |
|---|---|---|---|---|---|---|---|---|---|---|---|---|---|---|---|---|
| cct | tct | ctg | gcc | ggc | gtg | ggc | gag | cag | cag | gga | cag | ggc | gac | aat | acc | 2071 |
| Pro | Ser | Leu | Ala | Gly | Val | Gly | Glu | Gln | Gln | Gly | Gln | Gly | Asp | Asn | Thr | |
| | | | 185 | | | | | 190 | | | | | 195 | | | |

| | | | | | | | | | | | | | | | | |
|---|---|---|---|---|---|---|---|---|---|---|---|---|---|---|---|---|
| agc | aga | ggc | gcc | gag | cag | cct | aga | gag | gaa | cct | gga | cac | gct | ggc | cag | 2119 |
| Ser | Arg | Gly | Ala | Glu | Gln | Pro | Arg | Glu | Glu | Pro | Gly | His | Ala | Gly | Gln | |
| 200 | | | | 205 | | | | | 210 | | | | | 215 | | |

| | |
|---|---|
| gcc cca gga cct gcc ctg aca gat tgg gcc aga gtg cgg gag gaa ctg<br>Ala Pro Gly Pro Ala Leu Thr Asp Trp Ala Arg Val Arg Glu Glu Leu<br>220 225 230 | 2167 |
| gcc tct acc gga ccc cct gtg gtg gcc atg ccc gtg gtg atc aag aca<br>Ala Ser Thr Gly Pro Pro Val Val Ala Met Pro Val Val Ile Lys Thr<br>235 240 245 | 2215 |
| gag ggc cct gcc tgg acc cct ctg gaa ccc aag ctg atc acc cgg ctg<br>Glu Gly Pro Ala Trp Thr Pro Leu Glu Pro Lys Leu Ile Thr Arg Leu<br>250 255 260 | 2263 |
| gcc gat aca gtg cgg acc aag ggc ctg aga agc ccc atc acc atg gcc<br>Ala Asp Thr Val Arg Thr Lys Gly Leu Arg Ser Pro Ile Thr Met Ala<br>265 270 275 | 2311 |
| gag gtg gag gcc ctg atg agc agc ccc ctg ctg ccc cac gac gtg acc<br>Glu Val Glu Ala Leu Met Ser Ser Pro Leu Leu Pro His Asp Val Thr<br>280 285 290 295 | 2359 |
| aac ctg atg aga gtg atc ctg ggc cct gct ccc tac gcc ctg tgg atg<br>Asn Leu Met Arg Val Ile Leu Gly Pro Ala Pro Tyr Ala Leu Trp Met<br>300 305 310 | 2407 |
| gat gcc tgg ggc gtg cag ctg cag aca gtg atc gcc gct gcc acc aga<br>Asp Ala Trp Gly Val Gln Leu Gln Thr Val Ile Ala Ala Ala Thr Arg<br>315 320 325 | 2455 |
| gat ccc aga cac ccc gcc aat ggc cag ggc aga ggc gag cgg acc aac<br>Asp Pro Arg His Pro Ala Asn Gly Gln Gly Arg Gly Glu Arg Thr Asn<br>330 335 340 | 2503 |
| ctg gac aga ctg aag ggc ctg gcc gac ggc atg gtg ggc aat cct cag<br>Leu Asp Arg Leu Lys Gly Leu Ala Asp Gly Met Val Gly Asn Pro Gln<br>345 350 355 | 2551 |
| gga cag gcc gct ctg ctg agg cct ggc gaa ctg gtg gcc atc aca gcc<br>Gly Gln Ala Ala Leu Leu Arg Pro Gly Glu Leu Val Ala Ile Thr Ala<br>360 365 370 375 | 2599 |
| agc gcc ctg cag gcc ttc aga gag gtg gcc aga ctg gcc gag cct gcc<br>Ser Ala Leu Gln Ala Phe Arg Glu Val Ala Arg Leu Ala Glu Pro Ala<br>380 385 390 | 2647 |
| ggc cct tgg gcc gat atc acc cag ggc ccc agc gag agc ttc gtg gac<br>Gly Pro Trp Ala Asp Ile Thr Gln Gly Pro Ser Glu Ser Phe Val Asp<br>395 400 405 | 2695 |
| ttc gcc aac cgg ctg atc aag gcc gtg gag ggc agc gat ctg cct cct<br>Phe Ala Asn Arg Leu Ile Lys Ala Val Glu Gly Ser Asp Leu Pro Pro<br>410 415 420 | 2743 |
| agc gcc aga gcc ccc gtg atc atc gac tgc ttc cgg cag aag tcc cag<br>Ser Ala Arg Ala Pro Val Ile Ile Asp Cys Phe Arg Gln Lys Ser Gln<br>425 430 435 | 2791 |
| ccc gac atc cag cag ctg atc aga gcc gcc cct agc acc ctg acc acc<br>Pro Asp Ile Gln Gln Leu Ile Arg Ala Ala Pro Ser Thr Leu Thr Thr<br>440 445 450 455 | 2839 |
| cct ggc gag atc atc aaa tac gtg ctg gac cgg cag aag atc gcc cct<br>Pro Gly Glu Ile Ile Lys Tyr Val Leu Asp Arg Gln Lys Ile Ala Pro<br>460 465 470 | 2887 |
| ctg acc gat cag ggc att gcc gcc gct atg agc agc gcc atc cag cct<br>Leu Thr Asp Gln Gly Ile Ala Ala Ala Met Ser Ser Ala Ile Gln Pro<br>475 480 485 | 2935 |
| ctg gtg atg gcc gtg gtg aac aga gag agg gac ggc cag aca gga tct<br>Leu Val Met Ala Val Val Asn Arg Glu Arg Asp Gly Gln Thr Gly Ser<br>490 495 500 | 2983 |
| ggc ggc aga gcc aga ggc ctg tgc tac acc tgt ggc agc cct ggc cac<br>Gly Gly Arg Ala Arg Gly Leu Cys Tyr Thr Cys Gly Ser Pro Gly His<br>505 510 515 | 3031 |
| tac cag gcc cag tgc ccc aag aag cgg aag tcc ggc aac agc cgg gag<br>Tyr Gln Ala Gln Cys Pro Lys Lys Arg Lys Ser Gly Asn Ser Arg Glu<br>520 525 530 535 | 3079 |

```
aga tgc cag ctg tgt gac ggc atg ggc cac aac gcc aag cag tgc cgg       3127
Arg Cys Gln Leu Cys Asp Gly Met Gly His Asn Ala Lys Gln Cys Arg
            540                 545                 550 aag cgg gat ggc aat cag ggc cag agg ccc ggc aga gga ctg tct agc       3175
Lys Arg Asp Gly Asn Gln Gly Gln Arg Pro Gly Arg Gly Leu Ser Ser
            555                 560                 565 ggc cct tgg cct gga cct gag cag cct gcc gtg agc ctg gcc atg acc       3223
Gly Pro Trp Pro Gly Pro Glu Gln Pro Ala Val Ser Leu Ala Met Thr
            570                 575                 580 atg gaa cac aag gac cgg ccc ctg gtg cgc gtg atc ctg acc aac acc       3271
Met Glu His Lys Asp Arg Pro Leu Val Arg Val Ile Leu Thr Asn Thr
            585                 590                 595 ggc agc cac ccc gtg aag cag cgg agc gtg tac atc acc gcc ctg ctg       3319
Gly Ser His Pro Val Lys Gln Arg Ser Val Tyr Ile Thr Ala Leu Leu
600                 605                 610                 615 gac agc gga gcc gac atc acc atc atc agc gaa gag gac tgg ccc acc       3367
Asp Ser Gly Ala Asp Ile Thr Ile Ile Ser Glu Glu Asp Trp Pro Thr
                    620                 625                 630 gac tgg cct gtg gtg gac acc gcc aac ccc cag atc cac ggc atc ggc       3415
Asp Trp Pro Val Val Asp Thr Ala Asn Pro Gln Ile His Gly Ile Gly
                635                 640                 645 gga gga atc ccc atg cgg aag tcc cgg gat atg ata gag gtg ggg gtt       3463
Gly Gly Ile Pro Met Arg Lys Ser Arg Asp Met Ile Glu Val Gly Val
            650                 655                 660 att aac cga gac ggg tcg ttg gag cga ccc ctg ctc ctc ttc ccc gca       3511
Ile Asn Arg Asp Gly Ser Leu Glu Arg Pro Leu Leu Leu Phe Pro Ala
            665                 670                 675 gtc gct atg gtt aga ggg agt atc cta gga aga gat tgt ctg cag ggc       3559
Val Ala Met Val Arg Gly Ser Ile Leu Gly Arg Asp Cys Leu Gln Gly
680                 685                 690                 695 cta ggg ctc cgc ttg aca aat tta tag ggagggccac tgttctt act gtt       3609
Leu Gly Leu Arg Leu Thr Asn Leu                         Thr Val
            700                                             705 gcg cta cat ctg gct att ccg ctc aaa tgg aag tca gac cgc acg cct       3657
Ala Leu His Leu Ala Ile Pro Leu Lys Trp Lys Ser Asp Arg Thr Pro
            710                 715                 720 gtg tgg att gac cag tgg ccc ctt cct gaa ggt aaa ctt gta gcg cta       3705
Val Trp Ile Asp Gln Trp Pro Leu Pro Glu Gly Lys Leu Val Ala Leu
            725                 730                 735 acg caa tta gtg gaa aaa gaa tta cag tta ggc cac atc gag ccc agc       3753
Thr Gln Leu Val Glu Lys Glu Leu Gln Leu Gly His Ile Glu Pro Ser
            740                 745                 750 ctg agc tgc tgg aac acc ccc gtg ttc gtg atc aga aag gcc agc ggc       3801
Leu Ser Cys Trp Asn Thr Pro Val Phe Val Ile Arg Lys Ala Ser Gly
    755                 760                 765 agc tac aga ctg ctg cac gac ctg cgg gcc gtg aat gcc aag ctg gtg       3849
Ser Tyr Arg Leu Leu His Asp Leu Arg Ala Val Asn Ala Lys Leu Val
770                 775                 780                 785 ccc ttt ggc gcc gtg cag cag ggc gct cct gtg ctg tct gcc ctg cca       3897
Pro Phe Gly Ala Val Gln Gln Gly Ala Pro Val Leu Ser Ala Leu Pro
                    790                 795                 800 aga gga tgg ccc ctg atg gtg ctg gac ctg aag gac tgc ttc ttc agc       3945
Arg Gly Trp Pro Leu Met Val Leu Asp Leu Lys Asp Cys Phe Phe Ser
                805                 810                 815 atc cct ctg gcc gag cag gac aga gag gcc ttc gcc ttc acc ctg cct       3993
Ile Pro Leu Ala Glu Gln Asp Arg Glu Ala Phe Ala Phe Thr Leu Pro
            820                 825                 830 agc gtg aac aac cag gcc cca gcc aga cgg ttc cag tgg aag gtg ctg       4041
Ser Val Asn Asn Gln Ala Pro Ala Arg Arg Phe Gln Trp Lys Val Leu
            835                 840                 845
```

```
ccc cag ggc atg acc tgc agc ccc acc atc tgt cag ctg gtc gtg gga    4089
Pro Gln Gly Met Thr Cys Ser Pro Thr Ile Cys Gln Leu Val Val Gly
850                 855                 860                 865 cag gtg ctg gaa ccc ctg aga ctg aag cac ccc gcc ctg cgg atg ctg    4137
Gln Val Leu Glu Pro Leu Arg Leu Lys His Pro Ala Leu Arg Met Leu
                870                 875                 880 cac tac atg gac gac ctg ctc ctc gcc gct tct agc cac gac ggc ctg    4185
His Tyr Met Asp Asp Leu Leu Leu Ala Ala Ser Ser His Asp Gly Leu
            885                 890                 895 gaa gcc gcc gga aaa gaa gtg atc ggc acc ctg gaa aga gcc ggc ttc    4233
Glu Ala Ala Gly Lys Glu Val Ile Gly Thr Leu Glu Arg Ala Gly Phe
        900                 905                 910 acc atc agc ccc gac aag atc cag agg gaa ccc ggc gtg cag tac ctg    4281
Thr Ile Ser Pro Asp Lys Ile Gln Arg Glu Pro Gly Val Gln Tyr Leu
    915                 920                 925 ggc tac aag ctg ggc agc acc tat gtg gcc cct gtg ggc ctg gtg gcc    4329
Gly Tyr Lys Leu Gly Ser Thr Tyr Val Ala Pro Val Gly Leu Val Ala
930                 935                 940                 945 gag cca aga atc gcc acc ctg tgg gac gtg cag aaa ctg gtg ggc agc    4377
Glu Pro Arg Ile Ala Thr Leu Trp Asp Val Gln Lys Leu Val Gly Ser
                950                 955                 960 ctg cag tgg ctg agg cca gcc ctg ggc atc cct ccc aga ctg atg ggc    4425
Leu Gln Trp Leu Arg Pro Ala Leu Gly Ile Pro Pro Arg Leu Met Gly
            965                 970                 975 ccc ttc tac gag cag ctg cgg ggc tcc gac cct aat gag gcc cgg gag    4473
Pro Phe Tyr Glu Gln Leu Arg Gly Ser Asp Pro Asn Glu Ala Arg Glu
        980                 985                 990 tgg aac ctg gat atg aag atg gcc tgg cgg gag atc gtg cag ctg tcc    4521
Trp Asn Leu Asp Met Lys Met Ala Trp Arg Glu Ile Val Gln Leu Ser
    995                 1000                1005 acc act gcc gcc ctg gaa cgc tgg gat cca gca cag cca ctc gaa        4566
Thr Thr Ala Ala Leu Glu Arg Trp Asp Pro Ala Gln Pro Leu Glu
1010                1015                1020 ggt gcc gtg gcc aga tgt gaa cag ggc gcc atc ggc gtg ctg ggc        4611
Gly Ala Val Ala Arg Cys Glu Gln Gly Ala Ile Gly Val Leu Gly
1025                1030                1035 cag gga ctg agc acc cac ccc aga ccc tgc ctg tgg ctg ttc agc        4656
Gln Gly Leu Ser Thr His Pro Arg Pro Cys Leu Trp Leu Phe Ser
1040                1045                1050 acc cag ccc acc aag gcc ttc acc gcc tgg ctg gaa gtg ctg acc        4701
Thr Gln Pro Thr Lys Ala Phe Thr Ala Trp Leu Glu Val Leu Thr
1055                1060                1065 ctg ctg atc acc aag ctg cgg gcc agc gcc gtg aga acc ttc ggc        4746
Leu Leu Ile Thr Lys Leu Arg Ala Ser Ala Val Arg Thr Phe Gly
1070                1075                1080 aaa gag gtg gac atc ctg ctg cta cca gcc tgc ttt aga gag gac        4791
Lys Glu Val Asp Ile Leu Leu Leu Pro Ala Cys Phe Arg Glu Asp
1085                1090                1095 ctg ccc ctg cct gag gga atc ctg ctg gcc ctg aga ggc ttt gcc        4836
Leu Pro Leu Pro Glu Gly Ile Leu Leu Ala Leu Arg Gly Phe Ala
1100                1105                1110 ggc aag atc cgg tcc agc gac acc ccc agc atc ttc gat atc gcc        4881
Gly Lys Ile Arg Ser Ser Asp Thr Pro Ser Ile Phe Asp Ile Ala
1115                1120                1125 aga ccc ctg cac gtg tcc ctg aaa gtg cgc gtg acc gat cac cct        4926
Arg Pro Leu His Val Ser Leu Lys Val Arg Val Thr Asp His Pro
1130                1135                1140 gtg cct ggc ccc acc gtg ttt acc gac gcc agc agc agc acc cac        4971
Val Pro Gly Pro Thr Val Phe Thr Asp Ala Ser Ser Ser Thr His
1145                1150                1155
```

```
aag ggc gtg gtg gtg tgg aga gaa ggc ccc aga tgg gag atc aaa      5016
Lys Gly Val Val Val Trp Arg Glu Gly Pro Arg Trp Glu Ile Lys
1160                1165                1170 gaa atc gtg gac ctg ggc gcc tct gtg cag cag ctg gaa gcc aga      5061
Glu Ile Val Asp Leu Gly Ala Ser Val Gln Gln Leu Glu Ala Arg
1175                1180                1185 gcc gtg gcc atg gct ctg ctg ctg tgg ccc acc acc ccc acc aac      5106
Ala Val Ala Met Ala Leu Leu Leu Trp Pro Thr Thr Pro Thr Asn
1190                1195                1200 gtg gtg acc gac agc gcc ttc gtg gcc aag atg ctg ctg aag atg      5151
Val Val Thr Asp Ser Ala Phe Val Ala Lys Met Leu Leu Lys Met
1205                1210                1215 ggc cag gaa ggc gtc cct agc acc gcc gct gcc ttc atc ctg gaa      5196
Gly Gln Glu Gly Val Pro Ser Thr Ala Ala Ala Phe Ile Leu Glu
1220                1225                1230 gat gcc ctg tcc cag cgg agc gct atg gct gct gtg ctg cac gtg      5241
Asp Ala Leu Ser Gln Arg Ser Ala Met Ala Ala Val Leu His Val
1235                1240                1245 cgg agc cac agc gag gtg ccc ggc ttc ttc acc gag ggc aac gac      5286
Arg Ser His Ser Glu Val Pro Gly Phe Phe Thr Glu Gly Asn Asp
1250                1255                1260 gtg gcc gac agc cag gcc acc ttc cag gcc tac ccc ctg aga gag      5331
Val Ala Asp Ser Gln Ala Thr Phe Gln Ala Tyr Pro Leu Arg Glu
1265                1270                1275 gcc aag gac ctg cac aca gcc ctg cac atc ggc ccc aga gcc ctg      5376
Ala Lys Asp Leu His Thr Ala Leu His Ile Gly Pro Arg Ala Leu
1280                1285                1290 agc aag gcc tgc aac atc agc atg cag cag gcc aga gaa gtg gtg      5421
Ser Lys Ala Cys Asn Ile Ser Met Gln Gln Ala Arg Glu Val Val
1295                1300                1305 cag acc tgt ccc cac tgt aat agc gcc cct gct ctg gaa gcc ggc      5466
Gln Thr Cys Pro His Cys Asn Ser Ala Pro Ala Leu Glu Ala Gly
1310                1315                1320 gtg aac cct aga ggc ctc ggc cct ctg cag atc tgg cag acc gac      5511
Val Asn Pro Arg Gly Leu Gly Pro Leu Gln Ile Trp Gln Thr Asp
1325                1330                1335 ttc acc ctg gaa ccc cgg atg gcc cct aga agc tgg ctg gcc gtg      5556
Phe Thr Leu Glu Pro Arg Met Ala Pro Arg Ser Trp Leu Ala Val
1340                1345                1350 acc gtg gat acc gcc agc tcc gcc atc gtg gtg acc cag cac ggc      5601
Thr Val Asp Thr Ala Ser Ser Ala Ile Val Val Thr Gln His Gly
1355                1360                1365 aga gtg aca tct gtg gcc gcc cag cac cac tgg gcc aca gcc att      5646
Arg Val Thr Ser Val Ala Ala Gln His His Trp Ala Thr Ala Ile
1370                1375                1380 gcc gtg ctg ggc aga ccc aag gcc atc aag acc gac aac ggc agc      5691
Ala Val Leu Gly Arg Pro Lys Ala Ile Lys Thr Asp Asn Gly Ser
1385                1390                1395 tgc ttc acc agc cgg tcc acc aga gaa tgg ctg gcc aga tgg ggc      5736
Cys Phe Thr Ser Arg Ser Thr Arg Glu Trp Leu Ala Arg Trp Gly
1400                1405                1410 att gct cac acc acc ggc atc cca ggc aat agt cag ggc cag gcc      5781
Ile Ala His Thr Thr Gly Ile Pro Gly Asn Ser Gln Gly Gln Ala
1415                1420                1425 atg gtg gag aga gcc aac agg ctg ctg aag gac aag atc cgg gtg      5826
Met Val Glu Arg Ala Asn Arg Leu Leu Lys Asp Lys Ile Arg Val
1430                1435                1440 ctg gcc gag ggc gac ggc ttc atg aag cgg atc ccc gcc agc aaa      5871
Leu Ala Glu Gly Asp Gly Phe Met Lys Arg Ile Pro Ala Ser Lys
1445                1450                1455
```

| | | | | | | | | | | | | | | |
|---|---|---|---|---|---|---|---|---|---|---|---|---|---|---|
| cag | ggc | gag | ctg | ctg | gcc | aag | gcc | atg | tac | gcc | ctg | aac | cac | ttc | 5916 |
| Gln | Gly | Glu | Leu | Leu | Ala | Lys | Ala | Met | Tyr | Ala | Leu | Asn | His | Phe | |
| 1460 | | | | 1465 | | | | | 1470 | | | | | | |
| gag | cgg | ggc | gag | aac | acc | aag | acc | ccc | gtg | cag | aag | cac | tgg | cgg | 5961 |
| Glu | Arg | Gly | Glu | Asn | Thr | Lys | Thr | Pro | Val | Gln | Lys | His | Trp | Arg | |
| 1475 | | | | 1480 | | | | | 1485 | | | | | | |
| cct | acc | gtg | ctg | aca | gag | gga | ccc | ccc | gtg | aag | atc | cgg | atc | gag | 6006 |
| Pro | Thr | Val | Leu | Thr | Glu | Gly | Pro | Pro | Val | Lys | Ile | Arg | Ile | Glu | |
| 1490 | | | | 1495 | | | | | 1500 | | | | | | |
| aca | ggc | gag | tgg | gag | aag | ggg | tgg | aac | gtg | ctg | gtg | tgg | ggc | aga | 6051 |
| Thr | Gly | Glu | Trp | Glu | Lys | Gly | Trp | Asn | Val | Leu | Val | Trp | Gly | Arg | |
| 1505 | | | | 1510 | | | | | 1515 | | | | | | |
| ggc | tac | gcc | gct | gtc | aag | aac | cgg | gac | acc | gac | aaa | gtg | atc | tgg | 6096 |
| Gly | Tyr | Ala | Ala | Val | Lys | Asn | Arg | Asp | Thr | Asp | Lys | Val | Ile | Trp | |
| 1520 | | | | 1525 | | | | | 1530 | | | | | | |
| gtg | ccc | agc | cgg | aaa | gtg | aag | ccc | gac | gtg | acc | cag | aaa | gac | gaa | 6141 |
| Val | Pro | Ser | Arg | Lys | Val | Lys | Pro | Asp | Val | Thr | Gln | Lys | Asp | Glu | |
| 1535 | | | | 1540 | | | | | 1545 | | | | | | |
| gtg | acc | aag | aag | gac | gag | gcc | tcc | ccc | ctc | ttt | gcc | ggc | atc | agc | 6186 |
| Val | Thr | Lys | Lys | Asp | Glu | Ala | Ser | Pro | Leu | Phe | Ala | Gly | Ile | Ser | |
| 1550 | | | | 1555 | | | | | 1560 | | | | | | |
| gac | tgg | atc | cct | tgg | gag | gac | gag | cag | gaa | ggc | ctg | cag | ggc | gag | 6231 |
| Asp | Trp | Ile | Pro | Trp | Glu | Asp | Glu | Gln | Glu | Gly | Leu | Gln | Gly | Glu | |
| 1565 | | | | 1570 | | | | | 1575 | | | | | | |
| aca | gcc | agc | aac | aag | cag | gaa | aga | ccc | ggc | gag | gac | acc | ctg | gcc | 6276 |
| Thr | Ala | Ser | Asn | Lys | Gln | Glu | Arg | Pro | Gly | Glu | Asp | Thr | Leu | Ala | |
| 1580 | | | | 1585 | | | | | 1590 | | | | | | |
| gcc | aat | gag | agc | tga | gaattctgca | gatatccagc | acagtggcgg | ccgctcgagt | | | | | | | 6331 |
| Ala | Asn | Glu | Ser | | | | | | | | | | | | |
| 1595 | | | | | | | | | | | | | | | |

| | | | |
|---|---|---|---|
| ctagagggcc | cgtttaaacc | cgctgatcag | cctcgactgt gccttctagt tgccagccat | 6391 |
| ctgttgtttg | cccctccccc | gtgccttcct | gaccctgga aggtgccact cccactgtcc | 6451 |
| tttcctaata | aaatgaggaa | attgcatcgc | attgtctgag taggtgtcat tctattctgg | 6511 |
| ggggtggggt | ggggcaggac | agcaagggg | aggattggga agacaatagc aggcatgctg | 6571 |
| gggatgcggt | gggctctatg | gcttctgagg | cggaaagaac cagctggggc tctagggggt | 6631 |
| atccccacgc | gccctgtagc | ggcgcattaa | gcgcggcggg tgtggtggtt acgcgcagcg | 6691 |
| tgaccgctac | acttgccagc | gccctagcgc | ccgctccttt cgctttcttc ccttcctttc | 6751 |
| tcgccacgtt | cgccggcttt | ccccgtcaag | ctctaaatcg gggctccct ttagggttcc | 6811 |
| gatttagtgc | tttacggcac | ctcgacccca | aaaaacttga ttagggtgat ggttcacgta | 6871 |
| gtgggccatc | gccctgatag | acggtttttc | gccctttgac gttggagtcc acgttcttta | 6931 |
| atagtggact | cttgttccaa | actggaacaa | cactcaaccc tatctcggtc tattcttttg | 6991 |
| atttataagg | gattttgccg | atttcggcct | attggttaaa aaatgagctg atttaacaaa | 7051 |
| aatttaacgc | gaattaattc | tgtggaatgt | gtgtcagtta gggtgtggaa agtccccagg | 7111 |
| ctccccagca | ggcagaagta | tgcaaagcat | gcatctcaat tagtcagcaa ccaggtgtgg | 7171 |
| aaagtcccca | ggctccccag | caggcagaag | tatgcaaagc atgcatctca attagtcagc | 7231 |
| aaccatagtc | ccgcccctaa | ctccgcccat | cccgccccta actccgccca gttccgccca | 7291 |
| ttctccgccc | catggctgac | taattttttt | tatttatgca gaggccgagg ccgcctctgc | 7351 |
| ctctgagcta | ttccagaagt | agtgaggagg | cttttttgga ggcctaggct tttgcaaaaa | 7411 |
| gctcccggga | gcttgtatat | ccattttcgg | atctgatcaa gagacaggat gaggatcgtt | 7471 |
| tcgcatgatt | gaacaagatg | gattgcacgc | aggttctccg gccgcttggg tggagaggct | 7531 |

```
attcggctat gactgggcac aacagacaat cggctgctct gatgccgccg tgttccggct    7591
gtcagcgcag gggcgcccgg ttcttttgt caagaccgac ctgtccggtg ccctgaatga    7651
actgcaggac gaggcagcgc ggctatcgtg gctggccacg acgggcgttc cttgcgcagc    7711
tgtgctcgac gttgtcactg aagcgggaag ggactggctg ctattgggcg aagtgccggg    7771
gcaggatctc ctgtcatctc accttgctcc tgccgagaaa gtatccatca tggctgatgc    7831
aatgcggcgg ctgcatacgc ttgatccggc tacctgccca ttcgaccacc aagcgaaaca    7891
tcgcatcgag cgagcacgta ctcggatgga agccggtctt gtcgatcagg atgatctgga    7951
cgaagagcat caggggctcg cgccagccga actgttcgcc aggctcaagg cgcgcatgcc    8011
cgacggcgag gatctcgtcg tgacccatgg cgatgcctgc ttgccgaata tcatggtgga    8071
aaatggccgc ttttctggat tcatcgactg tggccggctg ggtgtggcgg accgctatca    8131
ggacatagcg ttggctaccc gtgatattgc tgaagagctt ggcggcgaat gggctgaccg    8191
cttcctcgtg ctttacggta tcgccgctcc cgattcgcag cgcatcgcct tctatcgcct    8251
tcttgacgag ttcttctgag cgggactctg gggttcgaaa tgaccgacca agcgacgccc    8311
aacctgccat cacgagattt cgattccacc gccgccttct atgaaaggtt gggcttcgga    8371
atcgttttcc gggacgccgg ctggatgatc ctccagcgcg gggatctcat gctggagttc    8431
ttcgcccacc ccaacttgtt tattgcagct tataatggtt acaaataaag caatagcatc    8491
acaaatttca caaataaagc attttttca ctgcattcta gttgtggttt gtccaaactc    8551
atcaatgtat cttatcatgt ctgtataccg tcgacctcta gctagagctt ggcgtaatca    8611
tggtcatagc tgtttcctgt gtgaaattgt tatccgctca caattccaca acatacga     8671 gccggaagca taaagtgtaa agcctggggt gcctaatgag tgagctaact cacattaatt    8731
gcgttgcgct cactgcccgc tttccagtcg ggaaacctgt cgtgccagct gcattaatga    8791
atcggccaac gcgcgggag aggcggtttg cgtattgggc gctcttccgc ttcctcgctc    8851
actgactcgc tgcgctcggt cgttcggctg cggcgagcgg tatcagctca ctcaaaggcg    8911
gtaatacggt tatccacaga atcaggggat aacgcaggaa agaacatgtg agcaaaaggc    8971
cagcaaaagg ccaggaaccg taaaaaggcc gcgttgctgg cgttttcca taggctccgc    9031 cccctgacg agcatcacaa aaatcgacgc tcaagtcaga ggtggcgaaa cccgacagga    9091
ctataaagat accaggcgtt tccccctgga agctccctcg tgcgctctcc tgttccgacc    9151
ctgccgctta ccggatacct gtccgccttt ctcccttcgg gaagcgtggc gctttctcat    9211
agctcacgct gtaggtatct cagttcggtg taggtcgttc gctccaagct gggctgtgtg    9271
cacgaacccc ccgttcagcc cgaccgctgc gccttatccg gtaactatcg tcttgagtcc    9331
aacccggtaa gacacgactt atcgccactg gcagcagcca ctggtaacag gattagcaga    9391
gcgaggtatg taggcggtgc tacagagttc ttgaagtggt ggcctaacta cggctacact    9451
agaagaacag tatttggtat ctgcgctctg ctgaagccag ttaccttcgg aaaaagagtt    9511
ggtagctctt gatccggcaa acaaaccacc gctggtagcg gttttttgt ttgcaagcag    9571 cagattacgc gcagaaaaaa aggatctcaa gaagatcctt tgatcttttc tacgggtct    9631 gacgctcagt ggaacgaaaa ctcacgttaa gggattttgg tcatgagatt atcaaaaagg    9691
atcttcacct agatcctttt aaattaaaaa tgaagtttta atcaatcta aagtatatat    9751 gagtaaactt ggtctgacag ttaccaatgc ttaatcagtg aggcacctat ctcagcgatc    9811
tgtctatttc gttcatccat agttgcctga ctccccgtcg tgtagataac tacgatacgg    9871
gagggcttac catctggccc cagtgctgca atgataccgc gagacccacg ctcaccggct    9931
```

```
ccagatttat cagcaataaa ccagccagcc ggaagggccg agcgcagaag tggtcctgca   9991
actttatccg cctccatcca gtctattaat tgttgccggg aagctagagt aagtagttcg  10051
ccagttaata gtttgcgcaa cgttgttgcc attgctacag gcatcgtggt gtcacgctcg  10111
tcgtttggta tggcttcatt cagctccggt tcccaacgat caaggcgagt tacatgatcc  10171
cccatgttgt gcaaaaaagc ggttagctcc ttcggtcctc cgatcgttgt cagaagtaag  10231
ttggccgcag tgttatcact catggttatg gcagcactgc ataattctct tactgtcatg  10291
ccatccgtaa gatgcttttc tgtgactggt gagtactcaa ccaagtcatt ctgagaatag  10351
tgtatgcggc gaccgagttg ctcttgcccg gcgtcaatac gggataatac cgcgccacat  10411
agcagaactt taaaagtgct catcattgga aaacgttctt cggggcgaaa actctcaagg  10471
atcttaccgc tgttgagatc cagttcgatg taacccactc gtgcacccaa ctgatcttca  10531
gcatctttta ctttcaccag cgtttctggg tgagcaaaaa caggaaggca aaatgccgca  10591
aaaaagggaa taagggcgac acggaaatgt tgaatactca tactcttcct ttttcaatat  10651
tattgaagca tttatcaggg ttattgtctc atgagcggat acatatttga atgtatttag  10711
aaaaataaac aaatagggt  tccgcgcaca tttccccgaa aagtgccacc tgacgtc     10768
```

```
<210> SEQ ID NO 15
<211> LENGTH: 703
<212> TYPE: PRT
<213> ORGANISM: Artificial Sequence
<220> FEATURE:
<223> OTHER INFORMATION: Synthetic Construct

<400> SEQUENCE: 15
```

Met Glu Ala Val Ile Lys Val Ile Ser Ser Ala Cys Lys Thr Tyr Cys
1               5                   10                  15

Gly Lys Ile Ser Pro Ser Lys Lys Glu Ile Gly Ala Met Leu Ser Leu
            20                  25                  30

Leu Gln Lys Glu Gly Leu Leu Met Ser Pro Ser Asp Leu Tyr Ser Pro
        35                  40                  45

Gly Ser Trp Asp Pro Ile Thr Ala Ala Leu Ser Gln Arg Ala Met Val
    50                  55                  60

Leu Gly Lys Ser Gly Glu Leu Lys Thr Trp Gly Leu Val Leu Gly Ala
65                  70                  75                  80

Leu Lys Ala Ala Arg Glu Glu Gln Val Thr Ser Glu Gln Ala Lys Phe
                85                  90                  95

Trp Leu Gly Leu Gly Gly Arg Val Ser Pro Gly Pro Glu Cys
            100                 105                 110

Ile Glu Lys Pro Ala Thr Glu Arg Arg Ile Asp Lys Gly Glu Glu Val
        115                 120                 125

Gly Glu Thr Thr Val Gln Arg Asp Ala Lys Met Ala Pro Glu Glu Ala
    130                 135                 140

Ala Thr Pro Lys Thr Val Gly Thr Ser Cys Tyr His Cys Gly Thr Ala
145                 150                 155                 160

Val Gly Cys Asn Cys Ala Thr Thr Ala Ser Ala Pro Pro Pro
                165                 170                 175

Tyr Val Gly Ser Gly Leu Tyr Pro Ser Leu Ala Gly Val Gly Glu Gln
            180                 185                 190

Gln Gly Gln Gly Asp Asn Thr Ser Arg Gly Ala Glu Gln Pro Arg Glu
        195                 200                 205

Glu Pro Gly His Ala Gly Gln Ala Pro Gly Pro Ala Leu Thr Asp Trp
    210                 215                 220

```
Ala Arg Val Arg Glu Glu Leu Ala Ser Thr Gly Pro Pro Val Val Ala
225                 230                 235                 240

Met Pro Val Val Ile Lys Thr Glu Gly Pro Ala Trp Thr Pro Leu Glu
            245                 250                 255

Pro Lys Leu Ile Thr Arg Leu Ala Asp Thr Val Arg Thr Lys Gly Leu
            260                 265                 270

Arg Ser Pro Ile Thr Met Ala Glu Val Glu Ala Leu Met Ser Ser Pro
        275                 280                 285

Leu Leu Pro His Asp Val Thr Asn Leu Met Arg Val Ile Leu Gly Pro
    290                 295                 300

Ala Pro Tyr Ala Leu Trp Met Asp Ala Trp Gly Val Gln Leu Gln Thr
305                 310                 315                 320

Val Ile Ala Ala Thr Arg Asp Pro Arg His Pro Ala Asn Gly Gln
                325                 330                 335

Gly Arg Gly Glu Arg Thr Asn Leu Asp Arg Leu Lys Gly Leu Ala Asp
                340                 345                 350

Gly Met Val Gly Asn Pro Gln Gly Gln Ala Ala Leu Leu Arg Pro Gly
            355                 360                 365

Glu Leu Val Ala Ile Thr Ala Ser Ala Leu Gln Ala Phe Arg Glu Val
    370                 375                 380

Ala Arg Leu Ala Glu Pro Ala Gly Pro Trp Ala Asp Ile Thr Gln Gly
385                 390                 395                 400

Pro Ser Glu Ser Phe Val Asp Phe Ala Asn Arg Leu Ile Lys Ala Val
                405                 410                 415

Glu Gly Ser Asp Leu Pro Pro Ser Ala Arg Ala Pro Val Ile Ile Asp
                420                 425                 430

Cys Phe Arg Gln Lys Ser Gln Pro Asp Ile Gln Leu Ile Arg Ala
            435                 440                 445

Ala Pro Ser Thr Leu Thr Thr Pro Gly Glu Ile Ile Lys Tyr Val Leu
450                 455                 460

Asp Arg Gln Lys Ile Ala Pro Leu Thr Asp Gln Gly Ile Ala Ala Ala
465                 470                 475                 480

Met Ser Ser Ala Ile Gln Pro Leu Val Met Ala Val Asn Arg Glu
            485                 490                 495

Arg Asp Gly Gln Thr Gly Ser Gly Gly Arg Ala Arg Gly Leu Cys Tyr
            500                 505                 510

Thr Cys Gly Ser Pro Gly His Tyr Gln Ala Gln Cys Pro Lys Lys Arg
        515                 520                 525

Lys Ser Gly Asn Ser Arg Glu Arg Cys Gln Leu Cys Asp Gly Met Gly
        530                 535                 540

His Asn Ala Lys Gln Cys Arg Lys Arg Asp Gly Asn Gln Gly Gln Arg
545                 550                 555                 560

Pro Gly Arg Gly Leu Ser Ser Gly Pro Trp Pro Gly Pro Glu Gln Pro
                565                 570                 575

Ala Val Ser Leu Ala Met Thr Met Glu His Lys Asp Arg Pro Leu Val
            580                 585                 590

Arg Val Ile Leu Thr Asn Thr Gly Ser His Pro Val Lys Gln Arg Ser
        595                 600                 605

Val Tyr Ile Thr Ala Leu Leu Asp Ser Gly Ala Asp Ile Thr Ile Ile
        610                 615                 620

Ser Glu Glu Asp Trp Pro Thr Asp Trp Pro Val Val Asp Thr Ala Asn
625                 630                 635                 640

Pro Gln Ile His Gly Ile Gly Gly Gly Ile Pro Met Arg Lys Ser Arg
```

```
                    645                 650                 655
Asp Met Ile Glu Val Gly Val Ile Asn Arg Asp Gly Ser Leu Glu Arg
        660                 665                 670

Pro Leu Leu Leu Phe Pro Ala Val Ala Met Val Arg Gly Ser Ile Leu
        675                 680                 685

Gly Arg Asp Cys Leu Gln Gly Leu Gly Leu Arg Leu Thr Asn Leu
        690                 695                 700

<210> SEQ ID NO 16
<211> LENGTH: 895
<212> TYPE: PRT
<213> ORGANISM: Artificial Sequence
<220> FEATURE:
<223> OTHER INFORMATION: Synthetic Construct

<400> SEQUENCE: 16

Thr Val Ala Leu His Leu Ala Ile Pro Leu Lys Trp Lys Ser Asp Arg
1               5                   10                  15

Thr Pro Val Trp Ile Asp Gln Trp Pro Leu Pro Glu Gly Lys Leu Val
            20                  25                  30

Ala Leu Thr Gln Leu Val Glu Lys Glu Leu Gln Leu Gly His Ile Glu
        35                  40                  45

Pro Ser Leu Ser Cys Trp Asn Thr Pro Val Phe Val Ile Arg Lys Ala
    50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
            100                 105                 110

Phe Ser Ile Pro Leu Ala Glu Gln Asp Arg Glu Ala Phe Ala Phe Thr
        115                 120                 125

Leu Pro Ser Val Asn Asn Gln Ala Pro Ala Arg Arg Phe Gln Trp Lys
    130                 135                 140

Val Leu Pro Gln Gly Met Thr Cys Ser Pro Thr Ile Cys Gln Leu Val
145                 150                 155                 160

Val Gly Gln Val Leu Glu Pro Leu Arg Leu Lys His Pro Ala Leu Arg
                165                 170                 175

Met Leu His Tyr Met Asp Asp Leu Leu Leu Ala Ala Ser Ser His Asp
            180                 185                 190

Gly Leu Glu Ala Ala Gly Lys Glu Val Ile Gly Thr Leu Glu Arg Ala
        195                 200                 205

Gly Phe Thr Ile Ser Pro Asp Lys Ile Gln Arg Glu Pro Gly Val Gln
    210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
            260                 265                 270

Met Gly Pro Phe Tyr Glu Gln Leu Arg Gly Ser Asp Pro Asn Glu Ala
        275                 280                 285

Arg Glu Trp Asn Leu Asp Met Lys Met Ala Trp Arg Glu Ile Val Gln
    290                 295                 300

Leu Ser Thr Thr Ala Ala Leu Glu Arg Trp Asp Pro Ala Gln Pro Leu
305                 310                 315                 320
```

```
Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
                340                 345                 350

Gln Pro Thr Lys Ala Phe Thr Ala Trp Leu Glu Val Leu Thr Leu Leu
                355                 360                 365

Ile Thr Lys Leu Arg Ala Ser Ala Val Arg Thr Phe Gly Lys Glu Val
            370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Arg Gly Phe Ala Gly Lys Ile Arg Ser
                405                 410                 415

Ser Asp Thr Pro Ser Ile Phe Asp Ile Ala Arg Pro Leu His Val Ser
                420                 425                 430

Leu Lys Val Arg Val Thr Asp His Pro Val Pro Gly Pro Thr Val Phe
            435                 440                 445

Thr Asp Ala Ser Ser Ser Thr His Lys Gly Val Val Val Trp Arg Glu
    450                 455                 460

Gly Pro Arg Trp Glu Ile Lys Glu Ile Val Asp Leu Gly Ala Ser Val
465                 470                 475                 480

Gln Gln Leu Glu Ala Arg Ala Val Ala Met Ala Leu Leu Leu Trp Pro
                485                 490                 495

Thr Thr Pro Thr Asn Val Val Thr Asp Ser Ala Phe Val Ala Lys Met
                500                 505                 510

Leu Leu Lys Met Gly Gln Glu Gly Val Pro Ser Thr Ala Ala Ala Phe
            515                 520                 525

Ile Leu Glu Asp Ala Leu Ser Gln Arg Ser Ala Met Ala Ala Val Leu
    530                 535                 540

His Val Arg Ser His Ser Glu Val Pro Gly Phe Phe Thr Glu Gly Asn
545                 550                 555                 560

Asp Val Ala Asp Ser Gln Ala Thr Phe Gln Ala Tyr Pro Leu Arg Glu
                565                 570                 575

Ala Lys Asp Leu His Thr Ala Leu His Ile Gly Pro Arg Ala Leu Ser
                580                 585                 590

Lys Ala Cys Asn Ile Ser Met Gln Gln Ala Arg Glu Val Val Gln Thr
            595                 600                 605

Cys Pro His Cys Asn Ser Ala Pro Ala Leu Glu Ala Gly Val Asn Pro
    610                 615                 620

Arg Gly Leu Gly Pro Leu Gln Ile Trp Gln Thr Asp Phe Thr Leu Glu
625                 630                 635                 640

Pro Arg Met Ala Pro Arg Ser Trp Leu Ala Val Thr Val Asp Thr Ala
                645                 650                 655

Ser Ser Ala Ile Val Val Thr Gln His Gly Arg Val Thr Ser Val Ala
                660                 665                 670

Ala Gln His His Trp Ala Thr Ala Ile Ala Val Leu Gly Arg Pro Lys
            675                 680                 685

Ala Ile Lys Thr Asp Asn Gly Ser Cys Phe Thr Ser Arg Ser Thr Arg
    690                 695                 700

Glu Trp Leu Ala Arg Trp Gly Ile Ala His Thr Thr Gly Ile Pro Gly
705                 710                 715                 720

Asn Ser Gln Gly Gln Ala Met Val Glu Arg Ala Asn Arg Leu Leu Lys
                725                 730                 735

Asp Lys Ile Arg Val Leu Ala Glu Gly Asp Gly Phe Met Lys Arg Ile
```

-continued

```
                    740                     745                     750
Pro Ala Ser Lys Gln Gly Glu Leu Leu Ala Lys Ala Met Tyr Ala Leu
            755                     760                 765

Asn His Phe Glu Arg Gly Glu Asn Thr Lys Thr Pro Val Gln Lys His
        770                     775              780

Trp Arg Pro Thr Val Leu Thr Glu Gly Pro Pro Val Lys Ile Arg Ile
785                     790             795                     800

Glu Thr Gly Glu Trp Glu Lys Gly Trp Asn Val Leu Val Trp Gly Arg
                805                 810                 815

Gly Tyr Ala Ala Val Lys Asn Arg Asp Thr Asp Lys Val Ile Trp Val
            820                 825             830

Pro Ser Arg Lys Val Lys Pro Asp Val Thr Gln Lys Asp Glu Val Thr
            835             840                 845

Lys Lys Asp Glu Ala Ser Pro Leu Phe Ala Gly Ile Ser Asp Trp Ile
        850             855                 860

Pro Trp Glu Asp Glu Gln Glu Gly Leu Gln Gly Glu Thr Ala Ser Asn
865                 870                 875                 880

Lys Gln Glu Arg Pro Gly Glu Asp Thr Leu Ala Ala Asn Glu Ser
                885             890                 895
```